US007501559B2

(12) United States Patent
Van Mellaert et al.

(10) Patent No.: US 7,501,559 B2
(45) Date of Patent: *Mar. 10, 2009

(54) PREVENTION OF BT RESISTANCE DEVELOPMENT

(75) Inventors: Herman Van Mellaert, Leuven (BE); Johan Botterman, Zevergem-de Pinte (BE); Jeroen Van Rie, Eeklo (BE); Henk Joos, Aalter (BE)

(73) Assignee: Bayer BioScience N.V., Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/594,824

(22) Filed: Nov. 9, 2006

(65) Prior Publication Data

US 2007/0150983 A1 Jun. 28, 2007

Related U.S. Application Data

(60) Division of application No. 10/809,953, filed on Mar. 26, 2004, now abandoned, which is a division of application No. 09/661,016, filed on Sep. 13, 2000, now Pat. No. 6,855,873, which is a division of application No. 09/176,320, filed on Oct. 22, 1998, now Pat. No. 6,172,281, which is a division of application No. 08/465,609, filed on Jun. 5, 1995, now Pat. No. 5,866,784, which is a continuation of application No. 08/173,274, filed on Dec. 23, 1993, now abandoned, which is a continuation of application No. 07/640,400, filed on Jan. 22, 1991, now abandoned, which is a continuation of application No. PCT/EP90/00905, filed on May 30, 1990.

(30) Foreign Application Priority Data

May 31, 1989 (GB) .............................. 89401499.2

(51) Int. Cl.
*A01H 5/00* (2006.01)
*C12N 15/82* (2006.01)
*C12N 15/32* (2006.01)

(52) U.S. Cl. .................... 800/302; 800/279; 536/23.71

(58) Field of Classification Search ...................... None
See application file for complete search history.

(56) References Cited

U.S. PATENT DOCUMENTS

| | | | |
|---|---|---|---|
| 5,126,133 | A | 6/1992 | Payne et al. |
| 5,188,960 | A | 2/1993 | Payne et al. |
| 5,244,802 | A | 9/1993 | Rangan |
| 5,246,852 | A | 9/1993 | Payne et al. |
| 5,500,365 | A | 3/1996 | Fischhoff et al. |
| 5,691,308 | A | 11/1997 | Payne et al. |
| 5,792,928 | A | 8/1998 | Sanchis et al. |
| 5,866,784 | A | 2/1999 | Van Mellaert et al. |
| 5,908,970 | A | 6/1999 | Van Mellaert et al. |
| 6,096,708 | A | 8/2000 | Payne et al. |
| 6,110,734 | A | 8/2000 | Sanchis et al. |
| 6,172,281 | B1 | 1/2001 | Van Mellaert et al. |
| 6,310,035 | B1 | 10/2001 | Sanchis et al. |
| 6,573,240 | B1 | 6/2003 | Payne et al. |
| 6,686,149 | B1 | 2/2004 | Sanchis et al. |
| 6,737,273 | B2 | 5/2004 | Payne et al. |
| 6,855,873 | B1 | 2/2005 | Van Mellaert et al. |
| 6,942,991 | B2 | 9/2005 | Sanchis et al. |
| 7,138,568 | B2 | 11/2006 | Payne et al. |
| 2003/0115628 | A1 | 6/2003 | Vincent et al. |
| 2004/0058860 | A1 | 3/2004 | Payne et al. |
| 2004/0194165 | A1 | 9/2004 | Payne et al. |
| 2005/0091714 | A1 | 4/2005 | Sanchis et al. |

FOREIGN PATENT DOCUMENTS

| | | |
|---|---|---|
| EP | 0 192 319 | 8/1986 |
| EP | 0 193 259 | 9/1986 |
| EP | 0 221 024 | 5/1987 |
| EP | 0 228 838 | 7/1987 |
| EP | 0 295 156 | 12/1988 |
| EP | 0 305 275 | 3/1989 |
| EP | 0 405 810 | 1/1991 |
| WO | 88/08880 | 11/1988 |

OTHER PUBLICATIONS

A. Devonshire et al., "A Carboxylesterase with Broad Substrate Specificity Causes Organophosphorous, Carbamate and Pyrethroid Resistance in Peach—Potato Aphids" (Myzus Persicae) Pesticide Biochemistry and Physiology, 1982, vol. 18, pp. 235-246.

"A Translation Fusion Product of Two Different Insecticidal Crystal Protein Genes of Bacillus thuringiensis Exhibits an Enlarged Insecticidal Spectrum" Chemical Abstracts, 1990, vol. 112, No. 21, p. 262, 193742F.

Brizzard et al., "Nucleotide sequence of an additional crystal protein gene cloned from Bacillus thuringiensis subsp. thuringiensis", Nucleic Acids Research, 1988, vol. 16, No. 6, pp. 2723-2724.

"Chimera Insecticidal Protein of Bacillus thuringiensis", Patent Abstracts of Japan, 1988, vol. 12, No. 391, (C-537).

"Binding of the Delta Endotoxin From Bacillus thuringiensis to Brush Border Membrane Vesicles of the Cabbage Butterfly (Pieris brassiae)", Eur. J. Biochem, 1988, vol. 173, pp. 85-91.

C. Hofmann et al., "Specificity of Bacillus thuringiensis endotoxins is Correlated with the Presence of High-Affinity Binding Sites in the Brush Border Membrance of Target Insect Midguts", Proc. Natl. Acad. Sci. USA, 1988, vol. 85, pp. 7844-7848.

Christina Hofmann, "The Binding of Bacillus thuringiensis Delta-endotoxin to Cultured Insect Cells and to Brush Border Membrane Vesicles", a dissertation submitted to the Swiss Federal Institute of Technology in Zurich, Switzerland, for the degree of Doctor of Natural Sciences, ADAG Administration & Druck AG, Zurich 1988, Diss. ETH No. 8498.

(Continued)

*Primary Examiner*—Anne R Kubelik
(74) *Attorney, Agent, or Firm*—Buchanan Ingersoll & Rooney PC

(57) ABSTRACT

Plants made resistant to insects by transforming their nuclear genome with two or more DNA sequences, each encoding a different non-competitively binding *B. thuringiensis* protoxin or insecticidal part thereof, preferably the toxin thereof.

5 Claims, 55 Drawing Sheets

OTHER PUBLICATIONS

C. Payne, "Current User and Future Prospects for Microbial Pest Control Agents", Med. Fac. Landbouww. Rijksuniv., Gent, 1987, vol. 52, No. 2a, pp. 113-123.

G. Mani, "Evolution of Resistance in the Presence of Two Insecticides", The Genetics Society of America, 1985, pp. 761-783.

H. Van Mellaert et al., "The Mode of Action of Bacillus Thuringiensis Delta-Endotoxins: Binding to Lepidopteran Midcut Membranes", Insect Pathology and Biological Control VIIIC2, p. 257.

Van Mellaert et al., "Binding of Different Types of Bacillus Thuringiensis Delta-Endotoxins to Midgut Brush Border Membrane Vesicles is Correlated with the Insecticidal Spectrum", XXI Annual meeting of the Society for invertebrate Pathology at the University of California, San Diego at La Jolla on Aug. 14-18, 1988.

J. Wong et al., "Cloning and Nucleotide Sequence of the Gene Coding for a 135-KDAL Protein f Bacillus Thuringiensis Aizawai", 1988, p. 27.

M. Vaeck et al., "Transgenic Plants Protected From Insect Attack", Nature, 1987, vol. 328, pp. 33-37.

"Simultaneous Expression of Two Kinds of Insecticidal Proteins", Patent Abstracts of Japan, 1989, vol. 13, No. 326, C-620.

"Specificity of Bacillus thuringiensis Delta-Endotoxins is Corrected With The Presence of High-Affinity Binding Sites in the Brush Broder Membrane of Target insect Midgut", Proc. Natl. Sci., 1988, vol. 85, pp. 7844-7848.

V. Sanchis et al., "Nucleotide sequence and analysis of the N-terminal coding region of the Spodoptera-active δ-endotoxin gene of Bacillus thuringiensis aizawai 7.29", Molecular Microbiology, 1989, vol. 3, No. 2, pp. 229-238.

B. Visser, "A screening for the presence of four different crystal protein gene types in 25 Bacillus thuringiensis strains", FEMS Microbiology Letters 58, 1989, pp. 121-124.

Honée et al., Nucleotide sequence of crystal protein gene isolated from B.thuringiensis subspecies entomocidus 60.5 coding for a toxin highly active against Spodoptera species, Nucleic Acids Research, 1988, vol. 16, No. 13, p. 6240.

Lecadet et al., "Identification of a δ-Endotoxin Gene Product Specifically Active against Spodoptera Littoralis Bdv. among Proteolysed Fractions of the Insecticidal Crystals of Bacillus thuringiensis subsp. aizawai 7.29", Applied and Environmental Microbiology, 1988, vol. 54, No. 11, pp. 2689-2698.

V. Sanchis et al., "Multiplicity of δ-endotoxin genes with different insecticidal specificities in Bacillus thuringiensis aizawai 7.29", Molecular Microbiology, 1988, vol. 2, No. 3, pp. 393-404.

% Max. Binding of $^{125}$I-Bt73-Toxin vs. [Competitor] (nM)

FIG. 5

% Max. Binding of $^{125}$I-Bt3-Toxin vs [Competitor] (nM)

FIG. 6

% Max. Binding of $^{125}$I-Bt73-Toxin vs. [Competitor] (nM)

FIG. 8

% Max. Binding of $^{125}$I-Bt14-Toxin vs [Competitor] (nM)

FIG. 10

% Max. Binding of $^{125}$I-Bt15-Toxin vs [Competitor] (nM)

```
          10          20          30          40          50
GGATCTGTTT TAATATAAGG GATTTGTGCC CTTCTCGTTA TATTCTTTTA 60          70          80          90         100
TTAGCCCCAA AAACTAGTGC AACTAAATAT TTTTATAATT ACACTGATTA 110         120         130         140         150
AATACTTTAT TTTTGGGAGT AAGATTTATG CTGAAATGTA ATAAAATTCG 160         170         180         190         200
TTCCATTTTC TGTATTTTCT CATAAAATGT TTCATATGCT TTAAATTGTA 210         220         230         240         250
GTAAAGAAAA ACAGTACAAA CTTAAAAGGA CTTTAGTAAT TTAATAAAAA 260         269         278         287
AAGGGGATAG TTT ATG GAA ATA AAT AAT CAA AAC CAA TGT
            MET Glu Ile Asn Asn Gln Asn Gln Cys
```

FIG. 13B

```
      296             305             314             323
GTG CCT TAC AAT TGT TTA AGT AAT CCT AAG GAG ATA ATA
Val Pro Tyr Asn Cys Leu Ser Asn Pro Lys Glu Ile Ile 332             341             350             359             368
TTA GGC GAG GAA AGG CTA GAA ACA GGG AAT ACT GTA GCA
Leu Gly Glu Glu Arg Leu Glu Thr Gly Asn Thr Val Ala 377             386             395             404
GAC ATT TCA TTA GGG CTT ATT AAT TTT CTA TAT TCT AAT
Asp Ile Ser Leu Gly Leu Ile Asn Phe Leu Tyr Ser Asn 413             422             431             440
TTT GTA CCA GGA GGA GGA TTT ATA GTA GGT TTA CTA GAA
Phe Val Pro Gly Gly Gly Phe Ile Val Gly Leu Leu Glu 449             458             467             476             485
TTA ATA TGG GGA TTT ATA GGG CCT TCG CAA TGG GAT ATT
Leu Ile Trp Gly Phe Ile Gly Pro Ser Gln Trp Asp Ile 494             503             512             521
TTT TTA GCT CAA ATT GAG CAA TTG ATT AGT CAA AGA ATA
Phe Leu Ala Gln Ile Glu Gln Leu Ile Ser Gln Arg Ile
```

FIG. 13C

```
       530             539              548             557
     GAA GAA TTT GCT AGG AAT CAG GCA ATT TCA AGA TTG GAG
     Glu Glu Phe Ala Arg Asn Gln Ala Ile Ser Arg Leu Glu 566             575              584             593             602
     GGG CTA AGC AAT CTT TAT AAG GTC TAT GTT AGA GCG TTT
     Gly Leu Ser Asn Leu Tyr Lys Val Tyr Val Arg Ala Phe 611             620              629             638
     AGC GAC TGG GAG AAA GAT CCT ACT AAT CCT GCT TTA AGG
     Ser Asp Trp Glu Lys Asp Pro Thr Asn Pro Ala Leu Arg 647             656              665             674
     GAA GAA ATG CGT ATA CAA TTT AAT GAC ATG AAT AGT GCT
     Glu Glu MET Arg Ile Gln Phe Asn Asp MET Asn Ser Ala 683             692              701             710             719
     CTC ATA ACG GCT ATT CCA CTT TTT AGA GTT CAA AAT TAT
     Leu Ile Thr Ala Ile Pro Leu Phe Arg Val Gln Asn Tyr 728             737              746             755
             GAA GTT GCT CTT TTA TCT GTA TAT GTT CAA GCC GCA AAC
             Glu Val Ala Leu Leu Ser Val Tyr Val Gln Ala Ala Asn
```

FIG. 13D

```
       764              773              782              791
TTA CAT TTA TCT ATT TTA AGG GAT GTT TCA GTT TTC GGA
Leu His Leu Ser Ile Leu Arg Asp Val Ser Val Phe Gly 800              809              818              827              836
GAA AGA TGG GGA TAT GAT ACA GCG ACT ATC AAT AAT CGC
Glu Arg Trp Gly Tyr Asp Thr Ala Thr Ile Asn Asn Arg 845              854              863              872
TAT AGT GAT CTG ACT AGC CTT ATT CAT GTT TAT ACT AAC
Tyr Ser Asp Leu Thr Ser Leu Ile His Val Tyr Thr Asn 881              890              899              908
CAT TGT GTG GAT ACG TAT AAT CAG GGA TTA AGG CGT TTG
His Cys Val Asp Thr Tyr Asn Gln Gly Leu Arg Arg Leu 917              926              935              944              953
GAA GGT CGT TTT CTT AGC GAT TGG ATT GTA TAT AAT CGT
Glu Gly Arg Phe Leu Ser Asp Trp Ile Val Tyr Asn Arg 962              971              980              989
TTC CGG AGA CAA TTG ACA ATT TCA GTA TTA GAT ATT GTT
Phe Arg Arg Gln Leu Thr Ile Ser Val Leu Asp Ile Val
```

FIG. 13E

```
      998              1007              1016              1025
GCG TTT TTT CCA AAT TAT GAT ATT AGA ACA TAT CCA ATT
Ala Phe Phe Pro Asn Tyr Asp Ile Arg Thr Tyr Pro Ile 1034              1043              1052              1061              1070
CAA ACA GCT ACT CAG CTA ACG AGG GAA GTC TAT CTG GAT
Gln Thr Ala Thr Gln Leu Thr Arg Glu Val Tyr Leu Asp 1079              1088              1097              1106
TTA CCT TTT ATT AAT CAA AAT CTT TCT CCT GCA GCA AGC
Leu Pro Phe Ile Asn Glu Asn Leu Ser Pro Ala Ala Ser 1115              1124              1133              1142
TAT CCA ACC TTT TCA GCT GCT GAA AGT GCT ATA ATT AGA
Tyr Pro Thr Phe Ser Ala Ala Glu Ser Ala Ile Ile Arg 1151              1160              1169              1178              1187
AGT CCT CAT TTA GTA GAC TTT TTA AAT AGC TTT ACC ATT
Ser Pro His Leu Val Asp Phe Leu Asn Ser Phe Thr Ile 1196              1205              1214              1223
TAT ACA GAT AGT CTG GCA CGT TAT GCA TAT TGG GGA GGG
Tyr Thr Asp Ser Leu Ala Arg Tyr Ala Tyr Trp Gly Gly
```

FIG. 13F

```
     1232            1241            1250            1259
CAC  TTG  GTA  AAT  TCT  TTC  CGC  ACA  GGA  ACC  ACT  ACT  AAT
His  Leu  Val  Asn  Ser  Phe  Arg  Thr  Gly  Thr  Thr  Thr  Asn 1268            1277            1286            1295            1304
TTG  ATA  AGA  TCC  CCT  TTA  TAT  GGA  AGG  GAA  GGA  AAT  ACA
Leu  Ile  Arg  Ser  Pro  Leu  Tyr  Gly  Arg  Glu  Gly  Asn  Thr 1313            1322            1331            1340
GAG  CGC  CCC  GTA  ACT  ATT  ACC  GCA  TCA  CCT  AGC  GTA  CCA
Glu  Arg  Pro  Val  Thr  Ile  Thr  Ala  Ser  Pro  Ser  Val  Pro 1349            1358            1367            1376
ATA  TTT  AGA  ACA  CTT  TCA  TAT  ATT  ACA  GGC  CTT  GAC  AAT
Ile  Phe  Arg  Thr  Leu  Ser  Tyr  Ile  Thr  Gly  Leu  Asp  Asn 1385            1394            1403            1412            1421
TCA  AAT  CCT  GTA  GCT  GGA  ATC  GAG  GGA  GTG  GAA  TTC  CAA
Ser  Asn  Pro  Val  Ala  Gly  Ile  Glu  Gly  Val  Glu  Phe  Gln 1430            1439            1448            1457
AAT  ACT  ATA  AGT  AGA  AGT  ATC  TAT  CGT  AAA  AGC  GGT  CCA
Asn  Thr  Ile  Ser  Arg  Ser  Ile  Tyr  Arg  Lys  Ser  Gly  Pro
```

FIG. 13G

```
      1466            1475            1484            1493
ATA GAT TCT TTT AGT GAA TTA CCA CCT CAA GAT GCC AGC
Ile Asp Ser Phe Ser Glu Leu Pro Pro Gln Asp Ala Ser 1502            1511            1520            1529            1538
GTA TCT CCT GCA ATT GGG TAT AGT CAC CGT TTA TGC CAT
Val Ser Pro Ala Ile Gly Tyr Ser His Arg Leu Cys His 1547            1556            1565            1574
GCA ACA TTT TTA GAA CGG ATT AGT GGA CCA AGA ATA GCA
Ala Thr Phe Leu Glu Arg Ile Ser Gly Pro Arg Ile Ala 1583            1592            1601            1610
GGC ACC GTA TTT TCT TGG ACA CAC CGT AGT GCC AGC CCT
Gly Thr Val Phe Ser Trp Thr His Arg Ser Ala Ser Pro 1619            1628            1637            1646            1655
ACT AAT GAA GTA AGT CCA TCT AGA ATT ACA CAA ATT CCA
Thr Asn Glu Val Ser Pro Ser Arg Ile Thr Gln Ile Pro 1664            1673            1682            1691
TGG GTA AAG GCG CAT ACT CTT GCA TCT GGT GCC TCC GTC
Trp Val Lys Ala His Thr Leu Ala Ser Gly Ala Ser Val
```

FIG. 13H

```
     1700            1709            1718            1727
ATT AAA GGT CCT GGA TTT ACA GGT GGA GAT ATT CTG ACT
Ile Lys Gly Pro Gly Phe Thr Gly Gly Asp Ile Leu Thr 1736            1745            1754            1763            1772
AGG AAT AGT ATG GGC GAG CTG GGG ACC TTA CGA GTA ACC
Arg Asn Ser MET Gly Glu Leu Gly Thr Leu Arg Val Thr 1781            1790            1799            1808
TTC ACA GGA AGA TTA CCA CAA AGT TAT TAT ATA CGT TTC
Phe Thr Gly Arg Leu Pro Gln Ser Tyr Tyr Ile Arg Phe 1817            1826            1835            1844
CGT TAT GCT TCG GTA GCA AAT AGG AGT GGT ACA TTT AGA
Arg Tyr Ala Ser Val Ala Asn Arg Ser Gly Thr Phe Arg 1853            1862            1871            1880            1889
TAT TCA CAG CCA CCT TCG TAT GGA ATT TCA TTT CCA AAA
Tyr Ser Gln Pro Pro Ser Tyr Gly Ile Ser Phe Pro Lys 1898            1907            1916            1925
ACT ATG GAC GCA GGT GAA CCA CTA ACA TCT CGT TCG TTC
Thr MET Asp Ala Gly Glu Pro Leu Thr Ser Arg Ser Phe
```

FIG. 131

```
    1934            1943            1952            1961
GCT CAT ACA ACA CTC TTC ACT CCA ATA ACC TTT TCA CGA
Ala His Thr Thr Leu Phe Thr Pro Ile Thr Phe Ser Arg 1970            1979            1988            1997            2006
GCT CAA GAA GAA TTT GAT CTA TAC ATC CAA TCG GGT GTT
Ala Gln Glu Glu Phe Asp Leu Tyr Ile Gln Ser Gly Val
                                                ---
    2015            2024            2033            2042
TAT ATA GAT CGA ATT GAA TTT ATA CCG GTT ACT GCA ACA
Tyr Ile Asp Arg Ile Glu Phe Ile Pro Val Thr Ala Thr
------------------------------------------------------->
    2051            2060            2069            2078
TTT GAG GCA GAA TAT GAT TTA GAA AGA GCG CAA AAG GTG
Phe Glu Ala Glu Tyr Asp Leu Glu Arg Ala Gln Lys Val 2087            2096            2105            2114            2123
GTG AAT GCC CTG TTT ACG TCT ACA AAC CAA CTA GGG CTA
Val Asn Ala Leu Phe Thr Ser Thr Asn Gln Leu Gly Leu 2132            2141            2150            2159
AAA ACA GAT GTG ACG GAT TAT CAT ATT GAT CAG GTA TCC
Lys Thr Asp Val Thr Asp Tyr His Ile Asp Gln Val Ser
```

FIG. 13J

```
      2168            2177            2186            2195
AAT CTA GTT GCG TGT TTA TCG GAT GAA TTT TGT CTG GAT
Asn Leu Val Ala Cys Leu Ser Asp Glu Phe Cys Leu Asp 2204            2213            2222            2231            2240
GAA AAG AGA GAA TTG TCC GAG AAA GTT AAA CAT GCA AAG
Glu Lys Arg Glu Leu Ser Glu Lys Val Lys His Ala Lys 2249            2258            2267            2276
CGA CTC AGT GAT GAG CGG AAT TTA CTT CAA GAT CCA AAC
Arg Leu Ser Asp Glu Arg Asn Leu Leu Gln Asp Pro Asn 2285            2294            2303            2312
TTC AGA GGG ATC AAT AGG CAA CCA GAC CGT GGC TGG AGA
Phe Arg Gly Ile Asn Arg Gln Pro Asp Arg Gly Trp Arg 2321            2330            2339            2348            2357
GGA AGT ACG GAT ATT ACT ATC CAA GGA GGA GAT GAC GTA
Gly Ser Thr Asp Ile Thr Ile Gln Gly Gly Asp Asp Val 2366            2375            2384            2393
TTC AAA GAG AAT TAC GTT ACG CTA CCG GGT ACC TTT GAT
Phe Lys Glu Asn Tyr Val Thr Leu Pro Gly Thr Phe Asp
```

FIG. 13K

```
     2402            2411            2420            2429
GAG TGC TAT CCA ACG TAT TTA TAT CAA AAA ATA GAT GAG
Glu Cys Tyr Pro Thr Tyr Leu Tyr Gln Lys Ile Asp Glu 2438            2447            2456            2465            2474
TCG AAA TTA AAA GCC TAT ACC CGT TAT CAA TTA AGA GGG
Ser Lys Leu Lys Ala Tyr Thr Arg Tyr Gln Leu Arg Gly 2483            2492            2501            2510
TAT ATC GAA GAT AGT CAA GAC TTA GAA ATC TAT TTA ATT
Tyr Ile Glu Asp Ser Gln Asp Leu Glu Ile Tyr Leu Ile 2519            2528            2537            2546
CGT TAC AAT GCA AAA CAC GAA ATA GTA AAT GTA CCA GGT
Arg Tyr Asn Ala Lys His Glu Ile Val Asn Val Pro Gly 2555            2564            2573            2582            2591
ACA GGA AGT TTA TGG CCT CTT TCT GTA GAA AAT CAA ATT
Thr Gly Ser Leu Trp Pro Leu Ser Val Glu Asn Gln Ile 2600            2609            2618            2627
GGA CCT TGT GGA GAA CCG AAT CGA TGC GCG CCA CAC CTT
Gly Pro Cys Gly Glu Pro Asn Arg Cys Ala Pro His Leu
```

FIG. 13L

```
           2636                2645                2654                2663
      GAA TGG AAT CCT GAT TTA CAC TGT TCC TGC AGA GAC GGG
      Glu Trp Asn Pro Asp Leu His Cys Ser Cys Arg Asp Gly 2672            2681            2690            2699            2708
      GAA AAA TGT GCA CAT CAT TCT CAT CAT TTC TCT TTG GAC
      Glu Lys Cys Ala His His Ser His His Phe Ser Leu Asp 2717            2726            2735            2744
      ATT GAT GTT GGA TGT ACA GAC TTA AAT GAG GAC TTA GGT
      Ile Asp Val Gly Cys Thr Asp Leu Asn Glu Asp Leu Gly 2753            2762            2771            2780
      GTA TGG GTG ATA TTC AAG ATT AAG ACG CAA GAT GGC CAC
      Val Trp Val Ile Phe Lys Ile Lys Thr Gln Asp Gly His 2789            2798            2807            2816            2825
      GCA CGA CTA GGG AAT CTA GAG TTT CTC GAA GAG AAA CCA
      Ala Arg Leu Gly Asn Leu Glu Phe Leu Glu Glu Lys Pro 2834            2843            2852            2861
      TTA TTA GGA GAA GCA CTA GCT CGT GTG AAA AGA GCG GAG
      Leu Leu Gly Glu Ala Leu Ala Arg Val Lys Arg Ala Glu
```

FIG. 13M

```
     2870            2879            2888            2897
AAA AAA TGG AGA GAC AAA CGC GAA ACA TTA CAA TTG GAA
Lys Lys Trp Arg Asp Lys Arg Glu Thr Leu Gln Leu Glu 2906            2915            2924            2933            2942
ACA ACT ATC GTT TAT AAA GAG GCA AAA GAA TCT GTA GAT
Thr Thr Ile Val Tyr Lys Glu Ala Lys Glu Ser Val Asp 2951            2960            2969            2978
GCT TTA TTT GTA AAC TCT CAA TAT GAT AGA TTA CAA GCG
Ala Leu Phe Val Asn Ser Gln Tyr Asp Arg Leu Gln Ala 2987            2996            3005            3014
GAT ACG AAC ATC GCG ATG ATT CAT GCG GCA GAT AAA CGC
Asp Thr Asn Ile Ala MET Ile His Ala Ala Asp Lys Arg 3023            3032            3041            3050            3059
GTT CAT AGA ATT CGA GAA GCG TAT CTG CCG GAG CTG TCT
Val His Arg Ile Arg Glu Ala Tyr Leu Pro Glu Leu Ser 3068            3077            3086            3095
GTG ATT CCG GGT GTC AAT GCG GCT ATT TTT GAA GAA TTA
Val Ile Pro Gly Val Asn Ala Ala Ile Phe Glu Glu Leu
```

FIG. 13N

```
    3104            3113            3122            3131
GAA GAG CGT ATT TTC ACT GCA TTT TCC CTA TAT GAT GCG
Glu Glu Arg Ile Phe Thr Ala Phe Ser Leu Tyr Asp Ala 3140            3149            3158            3167            3176
AGA AAT ATT ATT AAA AAT GGC GAT TTC AAT AAT GGC TTA
Arg Asn Ile Ile Lys Asn Gly Asp Phe Asn Asn Gly Leu 3185            3194            3203            3212
TTA TGC TGG AAC GTG AAA GGG CAT GTA GAG GTA GAA GAA
Leu Cys Trp Asn Val Lys Gly His Val Glu Val Glu Glu 3221            3230            3239            3248
CAA AAC AAT CAC CGT TCA GTC CTG GTT ATC CCA GAA TGG
Gln Asn Asn His Arg Ser Val Leu Val Ile Pro Glu Trp 3257            3266            3275            3284            3293
GAG GCA GAA GTG TCA CAA GAG GTT CGT GTC TGT CCA GGT
Glu Ala Glu Val Ser Gln Glu Val Arg Val Cys Pro Gly 3302            3311            3320            3329
CGT GGC TAT ATC CTT CGT GTT ACA GCG TAC AAA GAG GGA
Arg Gly Tyr Ile Leu Arg Val Thr Ala Tyr Lys Glu Gly
```

FIG. 13P

```
     3338            3347            3356            3365
TAT GGA GAA GGT TGC GTA ACG ATC CAT GAG ATC GAG AAC
Tyr Gly Glu Gly Cys Val Thr Ile His Glu Ile Glu Asn 3374            3383            3392            3401            3410
AAT ACA GAC GAA CTG AAA TTC AAC AAC TGT GTA GAA GAG
Asn Thr Asp Glu Leu Lys Phe Asn Asn Cys Val Glu Glu 3419            3428            3437            3446
GAA GTA TAT CCA AAC AAC ACG GTA ACG TGT ATT AAT TAT
Glu Val Tyr Pro Asn Asn Thr Val Thr Cys Ile Asn Tyr 3455            3464            3473            3482
ACT GCG ACT CAA GAA GAA TAT GAG GGT ACG TAC ACT TCT
Thr Ala Thr Gln Glu Glu Tyr Glu Gly Thr Tyr Thr Ser 3491            3500            3509            3518            3527
CGT AAT CGA GGA TAT GAC GAA GCC TAT GGT AAT AAC CCT
Arg Asn Arg Gly Tyr Asp Glu Ala Tyr Gly Asn Asn Pro 3536            3545            3554            3563
TCC GTA CCA GCT GAT TAT GCG TCA GTC TAT GAA GAA AAA
Ser Val Pro Ala Asp Tyr Ala Ser Val Tyr Glu Glu Lys
```

FIG. 13Q

```
     3572            3581            3590            3599
TCG TAT ACA GAT AGA CGA AGA GAG AAT CCT TGT GAA TCT
Ser Tyr Thr Asp Arg Arg Arg Glu Asn Pro Cys Glu Ser 3608            3617            3626            3635            3644
AAC AGA GGA TAT GGA GAT TAC ACA CCA CTA CCA GCT GGT
Asn Arg Gly Tyr Gly Asp Tyr Thr Pro Leu Pro Ala Gly 3653            3662            3671            3680
TAT GTA ACA AAG GAA TTA GAG TAC TTC CCA GAG ACC GAT
Tyr Val Thr Lys Glu Leu Glu Tyr Phe Pro Glu Thr Asp 3689            3698            3707            3716
AAG GTA TGG ATT GAG ATT GGA GAA ACA GAA GGA ACA TTC
Lys Val Trp Ile Glu Ile Gly Glu Thr Glu Gly Thr Phe 3725            3734            3743            3752            3761
ATC GTG GAC AGC GTG GAA TTA CTC CTT ATG GAG GAA TAG
Ile Val Asp Ser Val Glu Leu Leu Leu MET Glu Glu   •
```

FIG. 13R

```
      3771        3781        3791        3801        3811
GACCATCCGA GTATAGCAGT TTAATAAATA TTAATTAAAA TAGTAGTCTA 3821        3831        3841        3851        3861
ACTTCCGTTC CAATTAAATA AGTAAATTAC AGTTGTAAAA AAAAACGAAC 3871        3881        3891        3901
ATTACTCTTC AAAGAGCGAT GTCCGTTTTT TATATGGTGT GT
```

FIG. 14A

```
            10         20         30         40         50
    AATAGAATCT CAAATCTCGA TGACTGCTTA GTCTTTTTAA TACTGTCTAC 60         70         80         90        100
    TTGACAGGGG TAGGAACATA ATCGGTCAAT TTTAAATATG GGCATATAT 110        120        130        140        150
    TGATATTTTA TAAAATTTGT TACGTTTTTT GTATTTTTTC ATAAGATGTG 160        170        180        190        200
    TCATATGTAT TAAATCGTGG TAATGAAAAA CAGTATCAAA CTATCAGAAC 210        220        230     239
    TTTGGTAGTT TAATAAAAAA ACGGAGGTAT TTT ATG GAG GAA
                                    ----- MET Glu Glu 248        257        266        275
    AAT AAT CAA AAT CAA TGC ATA CCT TAC AAT TGT TTA AGT
    Asn Asn Gln Asn Gln Cys Ile Pro Tyr Asn Cys Leu Ser 284        293        302        311        320
    AAT CCT GAA GAA GTA CTT TTG GAT GGA GAA CGG ATA TCA
    Asn Pro Glu Glu Val Leu Leu Asp Gly Glu Arg Ile Ser
```

FIG. 14B

```
          329                    338                    347                    356
ACT GGT AAT TCA    TCA ATT GAT ATT    TCT CTG TCA CTT    GTT
Thr Gly Asn Ser    Ser Ile Asp Ile    Ser Leu Ser Leu    Val 365                    374                    383                    392
CAG TTT ATG GTA    TCT AAC TTT GTA    CCA GGG GGA GGA    TTT
Gln Phe Leu Val    Ser Asn Phe Val    Pro Gly Gly Gly    Phe 401                    410                    419                    428                    437
TTA GTT GGA TTA    ATA GAT TTT GTA    TGG GGA ATA GTT    GGC
Leu Val Gly Leu    Ile Asp Phe Val    Trp Gly Ile Val    Gly 446                    455                    464                    473
CCT TCT CAA TGG    GAT GCA TTT CTA    GTA CAA ATT GAA    CAA
Pro Ser Gln Trp    Asp Ala Phe Leu    Val Gln Ile Glu    Gln 482                    491                    500                    509
TTA ATT AAT GAA    AGA ATA GCT GAA    TTT GCT AGG AAT    GCT
Leu Ile Asn Glu    Arg Ile Ala Glu    Phe Ala Arg Asn    Ala 518                    527                    536                    545                    554
GCT ATT GCT AAT    TTA GAA GGA TTA    GGA AAC AAT TTC    AAT
Ala Ile Ala Asn    Leu Glu Gly Leu    Gly Asn Asn Phe    Asn
```

FIG. 14C

```
     563              572              581              590
ATA TAT GTG GAA GCA TTT AAA GAA TGG GAA GAA GAT CCT
Ile Tyr Val Glu Ala Phe Lys Glu Trp Glu Glu Asp Pro 599              608              617              626
AAT AAT CCA GAA ACC AGG ACC AGA GTA ATT GAT CGC TTT
Asn Asn Pro Glu Thr Arg Thr Arg Val Ile Asp Arg Phe 635              644              653              662              671
CGT ATA CTT GAT GGG CTA CTT GAA AGG GAC ATT CCT TCG
Arg Ile Leu Asp Gly Leu Leu Glu Arg Asp Ile Pro Ser 680              689              698              707
TTT CGA ATT TCT GGA TTT GAA GTA CCC CTT TTA TCC GTT
Phe Arg Ile Ser Gly Phe Glu Val Pro Leu Leu Ser Val 716              725              734              743
TAT GCT CAA GCG GCC AAT CTG CAT CTA GCT ATA TTA AGA
Tyr Ala Gln Ala Ala Asn Leu His Leu Ala Ile Leu Arg 752              761              770              779              788
GAT TCT GTA ATT TTT GGA GAA AGA TGG GGA TTG ACA ACG
Asp Ser Val Ile Phe Gly Glu Arg Trp Gly Leu Thr Thr
```

FIG. 14D

```
     797              806              815              824
ATA AAT GTC AAT GAA AAC TAT AAT AGA CTA ATT AGG CAT
Ile Asn Val Asn Glu Asn Tyr Asn Arg Leu Ile Arg His 833              842              851              860
ATT GAT GAA TAT GCT GAT CAC TGT GCA AAT ACG TAT AAT
Ile Asp Glu Tyr Ala Asp His Cys Ala Asn Thr Tyr Asn 869              878              887              896              905
CGG GGA TTA AAT AAT TTA CCG AAA TCT ACG TAT CAA GAT
Arg Gly Leu Asn Asn Leu Pro Lys Ser Thr Tyr Gln Asp 914              923              932              941
TGG ATA ACA TAT AAT CGA TTA CGG AGA GAC TTA ACA TTG
Trp Ile Thr Tyr Asn Arg Leu Arg Arg Asp Leu Thr Leu 950              959              968              977
ACT GTA TTA GAT ATC GCC GCT TTC TTT CCA AAC TAT GAC
Thr Val Leu Asp Ile Ala Ala Phe Phe Pro Asn Tyr Asp 986              995              1004             1013             1022
AAT AGG AGA TAT CCA ATT CAG CCA GTT GGT CAA CTA ACA
Asn Arg Arg Tyr Pro Ile Gln Pro Val Gly Gln Leu Thr
```

FIG. 14E

```
    1031            1040            1049            1058
AGG GAA GTT TAT ACG GAC CCA TTA ATT AAT TTT AAT CCA
Arg Glu Val Tyr Thr Asp Pro Leu Ile Asn Phe Asn Pro 1067            1076            1085            1094
CAG TTA CAG TCT GTA GCT CAA TTA CCT ACT TTT AAC GTT
Gln Leu Gln Ser Val Ala Gln Leu Pro Thr Phe Asn Val 1103            1112            1121            1130            1139
ATG GAG AGC AGC GCA ATT AGA AAT CCT CAT TTA TTT GAT
MET Glu Ser Ser Ala Ile Arg Asn Pro His Leu Phe Asp 1148            1157            1166            1175
ATA TTG AAT AAT CTT ACA ATC TTT ACG GAT TGG TTT AGT
Ile Leu Asn Asn Leu Thr Ile Phe Thr Asp Trp Phe Ser 1184            1193            1202            1211
GTT GGA CGC AAT TTT TAT TGG GGA GGA CAT CGA GTA ATA
Val Gly Arg Asn Phe Tyr Trp Gly Gly His Arg Val Ile 1220            1229            1238            1247            1256
TCT AGC CTT ATA GGA GGT GGT AAC ATA ACA TCT CCT ATA
Ser Ser Leu Ile Gly Gly Gly Asn Ile Thr Ser Pro Ile
```

FIG. 14F

```
        1265            1274            1283            1292
TAT GGA AGA GAG GCG AAC CAG GAG CCT CCA AGA TCC TTT
Tyr Gly Arg Glu Ala Asn Gln Glu Pro Pro Arg Ser Phe 1301            1310            1319            1328
ACT TTT AAT GGA CCG GTA TTT AGG ACT TTA TCA AAT CCT
Thr Phe Asn Gly Pro Val Phe Arg Thr Leu Ser Asn Pro 1337            1346            1355            1364            1373
ACT TTA CGA TTA TTA CAG CAA CCT TGG CCA GCG CCA CCA
Thr Leu Arg Leu Leu Gln Gln Pro Trp Pro Ala Pro Pro 1382            1391            1400            1409
TTT AAT TTA CGT GGT GTT GAA GGA GTA GAA TTT TCT ACA
Phe Asn Leu Arg Gly Val Glu Gly Val Glu Phe Ser Thr 1418            1427            1436            1445
CCT ACA AAT AGC TTT ACG TAT CGA GGA AGA GGT ACG GTT
Pro Thr Asn Ser Phe Thr Tyr Arg Gly Arg Gly Thr Val 1454            1463            1472            1481            1490
GAT TCT TTA ACT GAA TTA CCG CCT GAG GAT AAT AGT GTG
Asp Ser Leu Thr Glu Leu Pro Pro Glu Asp Asn Ser Val
```

FIG. 14G

```
      1499            1508             1517            1526
CCA CCT CGC GAA GGA TAT AGT CAT CGT TTA TGT CAT GCA
Pro Pro Arg Glu Gly Tyr Ser His Arg Leu Cys His Ala 1535            1544             1553            1562
ACT TTT GTT CAA AGA TCT GGA ACA CCT TTT TTA ACA ACT
Thr Phe Val Gln Arg Ser Gly Thr Pro Phe Leu Thr Thr 1571           1580            1589             1598            1607
GGT GTA GTA TTT TCT TGG ACG CAT CGT AGT GCA ACT CTT
Gly Val Val Phe Ser Trp Thr His Arg Ser Ala Thr Leu 1616            1625             1634            1643
ACA AAT ACA ATT GAT CCA GAG AGA ATT AAT CAA ATA CCT
Thr Asn Thr Ile Asp Pro Glu Arg Ile Asn Gln Ile Pro 1652            1661             1670            1679
TTA GTG AAA GGA TTT AGA GTT TGG GGG GGC ACC TCT GTC
Leu Val Lys Gly Phe Arg Val Trp Gly Gly Thr Ser Val 1688            1697             1706            1715            1724
ATT ACA GGA CCA GGA TTT ACA GGA GGG GAT ATC CTT CGA
Ile Thr Gly Pro Gly Phe Thr Gly Gly Asp Ile Leu Arg
```

FIG. 14H

```
     1733           1742            1751            1760
AGA  AAT  ACC  TTT  GGT  GAT  TTT  GTA  TCT  CTA  CAA  GTC  AAT
Arg  Asn  Thr  Phe  Gly  Asp  Phe  Val  Ser  Leu  Gln  Val  Asn 1769           1778            1787            1796
ATT  AAT  TCA  CCA  ATT  ACC  CAA  AGA  TAC  CGT  TTA  AGA  TTT
Ile  Asn  Ser  Pro  Ile  Thr  Gln  Arg  Tyr  Arg  Leu  Arg  Phe 1805           1814            1823            1832           1841
CGT  TAC  GCT  TCC  AGT  AGG  GAT  GCA  CGA  GTT  ATA  GTA  TTA
Arg  Tyr  Ala  Ser  Ser  Arg  Asp  Ala  Arg  Val  Ile  Val  Leu 1850           1859            1868            1877
ACA  GGA  GCG  GCA  TCC  ACA  GGA  GTG  GGA  GGC  CAA  GTT  AGT
Thr  Gly  Ala  Ala  Ser  Thr  Gly  Val  Gly  Gly  Gln  Val  Ser 1886           1895            1904            1913
GTA  AAT  ATG  CCT  CTT  CAG  AAA  ACT  ATG  GAA  ATA  GGG  GAG
Val  Asn  MET  Pro  Leu  Gln  Lys  Thr  MET  Glu  Ile  Gly  Glu 1922           1931            1940            1949           1958
AAC  TTA  ACA  TCT  AGA  ACA  TTT  AGA  TAT  ACC  GAT  TTT  AGT
Asn  Leu  Thr  Ser  Arg  Thr  Phe  Arg  Tyr  Thr  Asp  Phe  Ser
```

FIG. 14I

```
          1967            1976            1985            1994
AAT CCT TTT TCA TTT AGA GCT AAT CCA GAT ATA ATT GGG
Asn Pro Phe Ser Phe Arg Ala Asn Pro Asp Ile Ile Gly 2003            2012            2021            2030
ATA AGT GAA CAA CCT CTA TTT GGT GCA GGT TCT ATT AGT
Ile Ser Glu Gln Pro Leu Phe Gly Ala Gly Ser Ile Ser 2039            2048            2057            2066            2075
AGC GGT GAA CTT TAT ATA GAT AAA ATT GAA ATT ATT CTA
Ser Gly Glu Leu Tyr Ile Asp Lys Ile Glu Ile Ile Leu 2084            2093            2102            2111
GCA GAT GCA ACA TTT GAA GCA GAA TCT GAT TTA GAA AGA
Ala Asp Ala Thr Phe Glu Ala Glu Ser Asp Leu Glu Arg 2120            2129            2138            2147
GCA CAA AAG GCG GTG AAT GCC CTG TTT ACT TCT TCC AAT
Ala Gln Lya Ala Val Asn Ala Leu Phe Thr Ser Ser Asn 2156            2165            2174            2183            2192
CAA ATC GGG TTA AAA ACC GAT GTG ACG GAT TAT CAT ATT
Gln Ile Gly Leu Lys Thr Asp Val Thr Asp Tyr His Ile
```

FIG. 14J

```
     2201             2210             2219             2228
GAT CAA GTA TCC AAT TTA GTG GAT TGT TTA TCA GAT GAA
Asp Gln Val Ser Asn Leu Val Asp Cys Leu Ser Asp Glu 2237             2246             2255             2264
TTT TGT CTG GAT GAA AAG CGA GAA TTG TCC GAG AAA GTC
Phe Cys Leu Asp Glu Lys Arg Glu Leu Ser Glu Lys Val 2273             2282             2291             2300             2309
AAA CAT GCG AAG CGA CTC AGT GAT GAG CGG AAT TTA CTT
Lys His Ala Lys Arg Leu Ser Asp Glu Arg Asn Leu Leu 2318             2327             2336             2345
CAA GAT CCA AAC TTC AGA GGG ATC AAT AGA CAA CCA GAC
Gln Asp Pro Asn Phe Arg Gly Ile Asn Arg Gln Pro Asp 2354             2363             2372             2381
CGT GGC TGG AGA GGA AGT ACA GAT ATT ACC ATC CAA GGA
Arg Gly Trp Arg Gly Ser Thr Asp Ile Thr Ile Gln Gly 2390             2399             2408             2417             2426
GGA GAT GAC GTA TTC AAA GAG AAT TAC GTC ACA CTA CCG
Gly Asp Asp Val Phe Lys Glu Asn Tyr Val Thr Leu Pro
```

FIG. 14K

```
     2435              2444              2453              2462
GGT ACC GTT GAT GAG TGC TAT CCA ACG TAT TTA TAT CAG
Gly Thr Val Asp Glu Cys Tyr Pro Thr Tyr Leu Tyr Gln 2471              2480              2489              2498
AAA ATA GAT GAG TCG AAA TTA AAA GCT TAT ACC CGT TAT
Lys Ile Asp Glu Ser Lys Leu Lys Ala Tyr Thr Arg Tyr 2507              2516              2525              2534              2543
GAA TTA AGA GGG TAT ATC GAA GAT AGT CAA GAC TTA GAA
Glu Leu Arg Gly Tyr Ile Glu Asp Ser Gln Asp Leu Glu 2552              2561              2570              2579
ATC TAT TTG ATC CGT TAC AAT GCA AAA CAC GAA ATA GTA
Ile Tyr Leu Ile Arg Tyr Asn Ala Lys His Glu Ile Val 2588              2597              2606              2615
AAT GTG CCA GGC ACG GGT TCC TTA TGG CCG CTT TCA GCC
Asn Val Pro Gly Thr Gly Ser Leu Trp Pro Leu Ser Ala 2624              2633              2642              2651              2660
CAA AGT CCA ATC GGA AAG TGT GGA GAA CCG AAT CGA TGC
Gln Ser Pro Ile Gly Lys Cys Gly Glu Pro Asn Arg Cys
```

FIG. 14L

```
     2669              2678              2687              2696
GCG CCA CAC CTT GAA TGG AAT CCT GAT CTA GAT TGT TCC
Ala Pro His Leu Glu Trp Asn Pro Asp Leu Asp Cys Ser 2705              2714              2723              2732
TGC AGA GAC GGG GAA AAA TGT GCA CAT CAT TCC CAT CAT
Cys Arg Asp Gly Glu Lys Cys Ala His His Ser His His 2741              2750              2759              2768              2777
TTC ACC TTG GAT ATT GAT GTT GGA TGT ACA GAC TTA AAT
Phe Thr Leu Asp Ile Asp Val Gly Cys Thr Asp Leu Asn 2786              2795              2804              2813
GAG GAC TTA GGT GTA TGG GTG ATA TTC AAG ATT AAG ACG
Glu Asp Leu Gly Val Trp Val Ile Phe Lys Ile Lys Thr 2822              2831              2840              2849
CAA GAT GGC CAT GCA AGA CTA GGG AAT CTA GAG TTT CTC
Gln Asp Gly His Ala Arg Leu Gly Asn Leu Glu Phe Leu 2858              2867              2876              2885              2894
GAA GAG AAA CCA TTA TTA GGG GAA GCA CTA GCT CGT GTG
Glu Glu Lys Pro Leu Leu Gly Glu Ala Leu Ala Arg Val
```

FIG. 14M

|      | 2903 |     |     | 2912 |     |     | 2921 |     |     | 2930 |     |
|------|------|-----|-----|------|-----|-----|------|-----|-----|------|-----|
| AAA  | AGA  | GCG | GAG | AAG  | AAG | TGG | AGA  | GAC | AAA | CGA  | GAG | AAA |
| Lys  | Arg  | Ala | Glu | Lys  | Lys | Trp | Arg  | Asp | Lys | Arg  | Glu | Lys |

2939　　　　2948　　　　2957　　　　2966

CTG CAG TTG GAA ACA AAT ATT GTT TAT AAA GAG GCA AAA
Leu Gln Leu Glu Thr Asn Ile Val Tyr Lys Glu Ala Lys 2975　　　　2984　　　　2993　　　　3002　　　　3011

GAA TCT GTA GAT GCT TTA TTT GTA AAC TCT CAA TAT GAT
Glu Ser Val Asp Ala Leu Phe Val Asn Ser Gln Tyr Asp 3020　　　　3029　　　　3038　　　　3047

AGA TTA CAA GTG GAT ACG AAC ATC GCG ATG ATT CAT GCG
Arg Leu Gln Val Asp Thr Asn Ile Ala MET Ile His Ala 3056　　　　3065　　　　3074　　　　3083

GCA GAT AAA CGC GTT CAT AGA ATC CGG GAA GCG TAT CTG
Ala Asp Lys Arg Val His Arg Ile Arg Glu Ala Tyr Leu 3092　　　　3101　　　　3110　　　　3119　　　　3128

CCA GAG TTG TCT GTG ATT CCA GGT GTC AAT GCG GCC ATT
Pro Glu Leu Ser Val Ile Pro Gly Val Asn Ala Ala Ile

FIG. 14N

```
     3137              3146              3155              3164
TTC GAA GAA TTA GAG GGA CGT ATT TTT ACA GCG TAT TCC
Phe Glu Glu Leu Glu Gly Arg Ile Phe Thr Ala Tyr Ser 3173              3182              3191              3200
TTA TAT GAT GCG AGA AAT GTC ATT AAA AAT GGC GAT TTC
Leu Tyr Asp Ala Arg Asn Val Ile Lys Asn Gly Asp Phe 3209              3218              3227              3236              3245
AAT AAT GGC TTA TTA TGC TGG AAC GTG AAA GGT CAT GTA
Asn Asn Gly Leu Leu Cys Trp Asn Val Lys Gly His Val 3254              3263              3272              3281
GAT GTA GAA GAG CAA AAC AAC CAC CGT TCG GTC CTT GTT
Asp Val Glu Glu Gln Asn Asn His Arg Ser Val Leu Val 3290              3299              3308              3317
ATC CCA GAA TGG GAG GCA GAA GTG TCA CAA GAG GTT CGT
Ile Pro Glu Trp Glu Ala Glu Val Ser Gln Glu Val Arg 3326              3335              3344              3353     3362
GTC TGT CCA GGT CGT GGC TAT ATC CTT CGT GTC ACA GCA
Val Cys Pro Gly Arg Gly Tyr Ile Leu Arg Val Thr Ala
```

FIG. 14P

```
      3371            3380             3389            3398
TAT AAA GAG GGA TAT GGA GAG GGC TGC GTA ACG ATC CAT
Tyr Lys Glu Gly Tyr Gly Glu Gly Cys Val Thr Ile His 3407            3416             3425            3434
GAG ATC GAA GAC AAT ACA GAC GAA CTG AAA TTC AGC AAC
Glu Ile Glu Asp Asn Thr Asp Glu Leu Lys Phe Ser Asn 3443            3452            3461            3470            3479
TGT GTA GAA GAG GAA GTA TAT CCA AAC AAC ACA GTA ACG
Cys Val Glu Glu Glu Val Tyr Pro Asn Asn Thr Val Thr 3488            3497             3506            3515
TGT AAT AAT TAT ACT GGG ACT CAA GAA GAA TAT GAG GGT
Cys Asn Asn Tyr Thr Gly Thr Gln Glu Glu Tyr Glu Gly 3524            3533             3542            3551
ACG TAC ACT TCT CGT AAT CAA GGA TAT GAC GAA GCC TAT
Thr Tyr Thr Ser Arg Asn Gln Gly Tyr Asp Glu Ala Tyr 3560            3569            3578            3587            3596
GGT AAT AAC CCT TCC GTA CCA GCT GAT TAC GCT TCA GTC
Gly Asn Asn Pro Ser Val Pro Ala Asp Tyr Ala Ser Val
```

FIG. 14Q

```
         3605              3614              3623              3632
TAT GAA GAA AAA TCG TAT ACA GAT GGA CGA AGA GAG AAT
Tyr Glu Glu Lys Ser Tyr Thr Asp Gly Arg Arg Glu Asn 3641              3650              3659              3668
CCT TGT GAA TCT AAC AGA GGC TAT GGG GAT TAC ACA CCA
Pro Cys Glu Ser Asn Arg Gly Tyr Gly Asp Tyr Thr Pro 3677              3686              3695              3704              3713
CTA CCG GCT GGT TAT GTA ACA AAG GAT TTA GAG TAC TTC
Leu Pro Ala Gly Tyr Val Thr Lys Asp Leu Glu Tyr Phe 3722              3731              3740              3749
CCA GAG ACC GAT AAG GTA TGG ATT GAG ATC GGA GAA ACA
Pro Glu Thr Asp Lys Val Trp Ile Glu Ile Gly Glu Thr 3758              3767              3776              3785
GAA GGA ACA TTC ATC GTG GAT AGC GTG GAA TTA CTC CTT
Glu Gly Thr Phe Ile Val Asp Ser Val Glu Leu Leu Leu 3794              3803         3813         3823         3833
ATG GAG GAA TAA GATACGTTAT AAAATGTAAC GTATGCAAAT
MET Glu Glu  •
```

FIG. 14R

```
      3843        3853        3863        3873        3883
AAAGAATGAT  TACTGACCTA  TATTAACAGA  TAAATAAGAA  AATTTTTATA 3893        3903        3913        3923
CGAATAAAAA  ACGGACATCA  CTCTTAAGAG  AATGATGTCC
```

PREVENTION OF BT RESISTANCE DEVELOPMENT

This invention relates to plant cells and plants, the genomes of which are transformed to contain at least two genes, each coding for a different non-competitively binding *Bacillus thuringiensis* ("*B. thuringiensis*" or "Bt") insecticidal crystal protein ("ICP") for a specific target insect species, preferably belonging to the order of Lepidoptera or Coleoptera. Such transformed plants have advantages over plants transformed with a single *B. thuringiensis* ICP gene, especially with respect to the prevention of resistance development in the target insect species against the at least two *B. thuringiensis* ICPs, expressed in such plants.

This invention also relates to a process for the production of such transgenic plants, taking into account the competitive and non-competitive binding properties of the at least two *B. thuringiensis* ICPs in the target insect species' midgut. Simultaneous expression in plants of the at least two genes, each coding for a different non-competitively binding *B. thuringiensis* ICP in plants, is particularly useful to prevent or delay resistance development of insects against the at least two *B. thuringiensis* ICPs expressed in the plants.

This invention further relates to a process for the construction of novel plant expression vectors and to the novel plant expression vectors themselves, which contain the at least two *B. thuringiensis* ICP genes encoding the at least two non-competitively binding *B. thuringiensis* ICPs. Such vectors allow integration and coordinate expression of the at least two *B. thuringiensis* ICP genes in plants.

BACKGROUND OF THE INVENTION

Since the development and the widespread use of chemical insecticides, the occurrence of resistant insect strains has been an important problem. Development of insecticide resistance is a phenomenon dependent on biochemical, physiological, genetic and ecological mechanisms. Currently, insect resistance has been reported against all major classes of chemical insecticides including chlorinated hydrocarbons, organophosphates, carbamates, and pyrethroid compounds (Brattsten et al., 1986).

In contrast to the rapid development of insect resistance to synthetic insecticides, development of insect resistance to bacterial insecticides such as *B. thuringiensis* sprays has evolved slowly despite many years of use (Brattsten et al., 1986). The spore forming gram-positive bacterium *B. thuringiensis* produces a parasporal crystal which is composed of crystal proteins (ICPs) having insecticidal activity. Important factors decreasing the probability of emergence of resistant insect strains in the field against *B. thuringiensis* sprays are: firstly the short half-life of *B. thuringiensis* sprays after foliar application; secondly the fact that commercial *B. thuringiensis* preparations often consist of a mixture of several insecticidal factors including spores, ICPs and eventually beta-exotoxins (Shields, 1987); and thirdly the transitory nature of plant-pest interactions. Many successful field trials have shown that commercial preparations of a *B. thuringiensis* containing its spore-crystal complex, effectively control lepidopterous pests in agriculture and forestry (Krieg and Langenbruch, 1981). *B. thuringiensis* is at present the most widely used pathogen for microbial control of insect pests.

Various laboratory studies, in which selection against *B. thuringiensis* was applied over several generations of insects, have confirmed that resistance against *B. thuringiensis* is seldom obtained. However, it should be emphasized that the laboratory conditions represented rather low selection pressure conditions.

For example, Goldman et al. (1986) have applied selection with *B. thuringiensis israelensis* toxin over 14 generations of *Aedes aegypti* and found only a marginal decrease in sensitivity. The lack of any observable trend toward decreasing susceptibility in the selected strains may be a reflection of the low selection pressure ($LC_{50}$) carried out over a limited number of generations. However, it should be pointed out that Georghiou et al. (In: Insecticide Resistance in Mosquitoes: Research on new chemicals and techniques for management. In "Mosquito Control Research, Annual Report 1983, University of California.") with *Culex quinquefasciatus* obtained an 11-fold increase in resistance to *B. thuringiensis israelensis* after 32 generations at $LC_{95}$ selection presssure.

McGaughey (1985) reported that the grain storage pest *Plodia interpunctella* developed resistance to the spore-crystal complex of *B. thuringiensis*; after 15 generations of selection with the Indian meal moth, *Plodia interpunctella*, using a commercial *B. thuringiensis* HD-1 preparation ("Dipel", Abbott Laboratories, North Chicago, Ill. 60064, USA), a 100-fold decrease in *B. thuringiensis* sensitivity was reported. Each of the colonies was cultured for several generations on a diet treated with a constant *B. thuringiensis* dosage which was expected to produce 70-90% larval mortality. Under these high selection presssure conditions, insect resistance to *B. thuringiensis* increased rapidly. More recently, development of resistance against *B. thuringiensis* is also reported for the almond moth, *Cadra cautella* (McGaughey and Beeman, 1988). Resistance was stable when selection was discontinued and was inherited as a recessive trait (McGaughey and Beeman, 1988). The mechanism of insect resistance to *B. thuringiensis* toxins of *Plodia interpunctella* and *Cadra cautella* has not been elucidated.

The main cause of *B. thuringiensis* resistance development in both reported cases involving grain storage was the environmental conditions prevailing during the grain storage. Under the conditions in both cases, the environment was relatively stable, so *B. thuringiensis* degradation was slow and permitted successive generations of the pest to breed in the continuous presence of the microbial insecticide. The speed at which *Plodia* developed resistance to *B. thuringiensis* in one study suggests that it could do so within one single storage season in the bins of treated grain.

Although insect resistance development against *B. thuringiensis* has mostly been observed in laboratory and pilot scale studies, very recent indications of *B. thuringiensis* resistance development in *Plutella xylostella* populations in the (cabbage) field have been reported (Kirsch and Schmutterer, 1988). A number of factors have led to a continuous exposure of *P. xylostella* to *B. thuringiensis* in a relatively small geographic area. This and the short generation cycle of *P. xylostella* have seemingly led to an enormous selection pressure resulting in decreased susceptibility and increased resistance to *B. thuringiensis*.

A procedure for expressing a *B. thuringiensis* ICP gene in plants in order to render the plants insect-resistant (European patent publication ("EP") 0193259 {which is incorporated herein by reference}; Vaeck et al., 1987; Barton et al., 1987; Fischhoff et al., 1987) provides an entirely new approach to insect control in agriculture which is at the same time safe, environmentally attractive and cost-effective. An important determinant for the success of this approach will be whether insects will be able to develop resistance to *B. thuringiensis* ICPs expressed in transgenic plants (Vaeck et al., 1987; Barton et al., 1987; Fischhoff et al., 1987). In contrast with a foliar application, after which B. thuringiensis ICPs are rapidly degraded, the transgenic plants will exert a continuous selection pressure. It is clear from laboratory selection experiments that a continuous selection pressure has led to adaptation to B. thuringiensis and its components in several insect species. In this regard, it should be pointed out that the conditions in the laboratory which resulted in the development of insect-resistance to B. thuringiensis are very similar to the situation with transgenic plants which produce B. thuringiensis ICPs and provide a continuous selection pressure on insect populations feeding on the plants. Mathematical models of selection pressure predict that, if engineered insect-resistant plants become a permanent part of their environment, resistance development in insects will emerge rapidly (Gould, 1988). Thus, the chances for the development of insect resistance to B. thuringiensis in transgenic plants may be considerably increased as compared to the field application of B. thuringiensis sprays. A Heliothis virescens strain has been reported that is 20 times more resistant to B. thuringiensis HD-1 ICP produced by transgenic Pseudomonas fluorescens and 6 times more resistant to the pure ICP (Stone et al., 1989). Furthermore, the monetary and human costs of resistance are difficult to assess, but loss of pesticide effectiveness invariably entails increased application frequencies and dosages and, finally, more expensive replacement compounds as new pesticides become more difficult to discover and develop.

Therefore, it would be desirable to develop means for delaying or even preventing the evolution of resistance to B. thuringiensis.

B. thuringiensis strains, active against Lepidoptera (Dulmage et al., 1981), Diptera (Goldberg and Margalit, 1977) and Coleoptera (Krieg et al., 1983), have been described. It has become clear that there is a substantial heterogeneity among ICPs from different strains active against Lepidoptera, as well as among ICPs from strains active against Coleoptera (Hofte and Whiteley, 1989). An overview of the different B. thuringiensis ICP genes, that have been characterized, is given in Table 2 (which follows the Examples herein).

Most of the anti-Lepidopteran B. thuringiensis (e.g., Bt3, Bt2, Bt73, Bt14, Bt15, Bt4, Bt18) ICP genes encode 130 to 140 kDa protoxins which dissolve in the alkaline environment of an insect's midgut and are proteolytically activated into an active toxin of 60-65 kDa. These ICPs are related and can be recognized as members of the same family based on sequence homologies. The sequence divergence however is substantial, and the insecticidal spectrum, among the order Lepidoptera, may be substantially different (Hofte et al., 1988).

The P2 toxin gene and the cry B2 gene are different from the above-mentioned genes in that they do not encode high molecular weight protoxins but rather toxins of around 70 kDa (Donovan et al., 1988 and Widner and Whiteley, 1989, respectively).

It has recently become clear that heterogeneity exists also in the anti-Coleopteran toxin gene family. Whereas several previously reported toxin gene sequences from different B. thuringiensis isolates with anti-Coleopteran activity were identical (EP 0149162 and 0202739), the sequences and structure of bt21 and bt22 are substantially divergent (European patent application ("EPA") 89400428.2).

While the insecticidal spectra of B. thuringiensis ICPs are different, the major pathway of their toxic action is believed to be common. All B. thuringiensis ICPs, for which the mechanism of action has been studied in any detail, interact with the midgut epithelium of sensitive species and cause lysis of the epithelial cells (Knowles and Ellar, 1986) due to the fact that the permeability characteristics of the brush border membrane and the osmotic balance over this membrane are perturbed. In the pathway of toxic action of B. thuringiensis ICPs, the binding of the toxin to receptor sites on the brush border membrane of these cells is an important feature (Hofmann et al., 1988b). The toxin binding sites in the midgut can be regarded as an ICP-receptor since toxin is bound in a saturable way and with high affinity (Hofmann et al., 1988a).

Although this outline of the mode of action of B. thuringiensis ICPs is generally accepted, it remains a matter of discussion what the essential determinant(s) are for the differences in their insecticidal spectra. Haider et al. (1986) emphasize the importance of specific proteases in the insect midgut. Hofmann et al. (1988b) indicate that receptor binding is a prerequisite for toxic activity and describe that Pieris brassicae has two distinct receptor populations for two toxins. Other authors have suggested that differences in the environment of the midgut (e.g., pH of the midgut) might be crucial.

SUMMARY OF THE INVENTION

In accordance with this invention, a plant is provided having, stably integrated into its genome, at least two B. thuringiensis ICP genes encoding at least two non-competitively binding insecticidal B. thuringiensis ICPs, preferably the active toxins thereof, against a specific target insect, preferably against a Lepidoptera or Coleoptera. Such a plant is characterized by the simultaneous expression of the at least two non-competitively binding B. thuringiensis ICPs.

Also in accordance with this invention, at least two ICP genes, particularly two genes or parts thereof coding for two non-competitively binding anti-Lepidopteran or anti-Coleopteran B. thuringiensis ICPs, are cloned into a plant expression vector. Plant cells transformed with this vector are characterized by the simultaneous expression of the at least two B. thuringiensis ICP genes. The resulting transformed plant cell can be used to produce a transformed plant in which the plant cells: 1. contain the at least two B. thuringiensis ICP genes or parts thereof encoding at least two non-competitively binding anti-Lepidopteran or anti-Coleopteran B. thuringiensis ICPs as a stable insert into their genome; and 2. express the genes simultaneously, thereby conferring on the plant improved resistance to at least one target species of insect, so as to prevent or delay development of resistance to B. thuringiensis of the at least one target species of insect feeding on the transformed plant.

Further in accordance with this invention, plant expression vectors are provided which allow integration and simultaneous expression of at least two B. thuringiensis ICP genes in a plant cell and which comprise one or more chimeric genes, each containing in the same transcriptional unit: a promoter which functions in the plant cell to direct the synthesis of mRNA encoded by one of the ICP genes; one or more different ICP genes, each encoding a non-competitively binding B. thuringiensis ICP; preferably a marker gene; a 3' non-translated DNA sequence which functions in the plant cell for 3' end formation and the addition of polyadenylate nucleotides to the 3' end of the mRNA; and optionally a DNA sequence encoding a protease-sensitive protein part between any two ICP genes.

BRIEF DESCRIPTION OF THE DRAWINGS

FIG. 1 shows the binding of $^{125}$I-labeled Bt2 toxins to M. sexta brush border membrane vesicles as a function of the concentration of competitor.

FIG. 2 shows the binding of $^{125}$I-labeled Bt3 toxins to *M. sexta* brush border membrane vesicles as a function of the concentration of competitor.

FIG. 4 shows the binding of $^{125}$I-labeled Bt2 toxins to *H. virescens* brush border membrane vesicles as a function of the concentration of competitor.

FIG. 5 shows the binding of $^{125}$I-labeled Bt3 toxins to *H. virescens* brush border membrane vesicles as a function of the concentration of competitor.

FIG. 6 shows the binding of $^{125}$I-labeled Bt73 toxins to *H. virescens* brush border membrane vesicles as a function of the concentration of competitor

FIG. 8 shows the binding of $^{125}$I-labeled Bt14 toxins to *P. brassicae* brush border membrane vesicles.

FIG. 10 shows the binding of $^{125}$I-labeled Bt15 toxins to *M. sexta* brush border membrane vesicles.

FIG. 11 shows the binding of $^{125}$I-labeled Bt2 toxins to *M. sexta* brush border membrane vesicles

FIG. 13 shows the nucleotide sequence and deduced amino acid sequence of the open reading frame of the bt4 gene, isolated from HD-68.

FIG. 14 shows the nucleotide sequence and deduced amino acid sequence of the open reading frame of the bt15 gene, isolated from HD-110.

DETAILED DESCRIPTION OF THE INVENTION

Definitions

Figure 3:
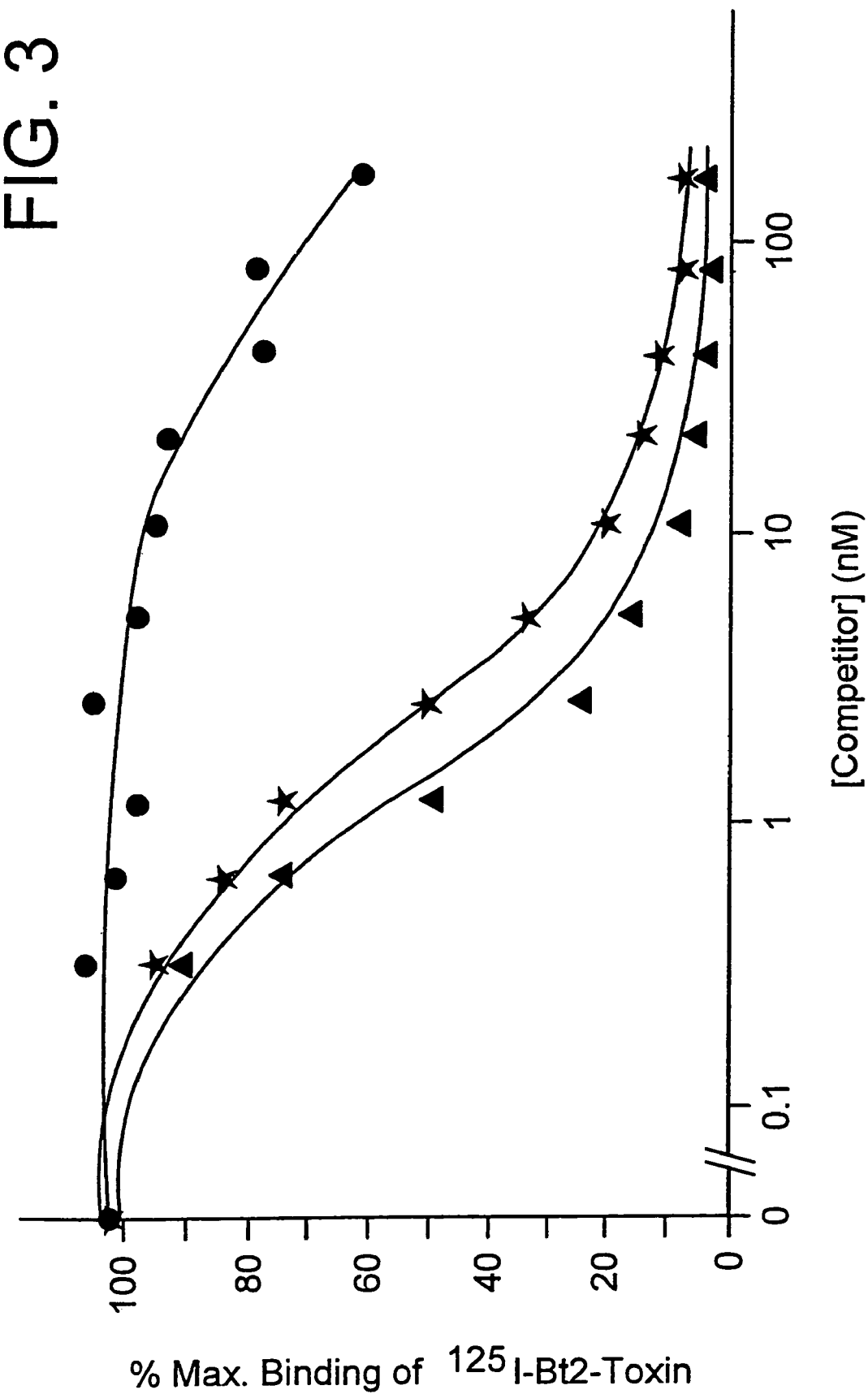
FIG. 3 shows the binding of $^{125}$I-labeled Bt73 toxins to *M. sexta* brush border membrane vesicles as a function of the concentration of competitor.

As used herein, "*B. thuringiensis* ICP" (or "ICP") should be understood as an intact protein or a part thereof which has insecticidal activity and which can be produced in nature by *B. thuringiensis*. An ICP can be a protoxin, as well as an active toxin or another insecticidal truncated part of a protoxin which need not be crystalline and which need not be a naturally occurring protein. In this regard, an ICP can be a chimaeric toxin encoded by the combination of two variable regions of two different ICP genes as disclosed in EP 0228838.

As used herein, "protoxin" should be understood as the primary translation product of a full-length gene encoding an ICP.

As used herein, "toxin", "toxic core" or "active toxin" should all be understood as a part of a protoxin which can be obtained by protease (e.g., by trypsin) cleavage and has insecticidal activity.

As used herein, "gene" should be understood as a full-length DNA sequence encoding a protein (e.g., such as is found in nature), as well as a truncated fragment thereof encoding at least the active part (i.e., toxin) of the protein encoded by the full-length DNA sequence, preferably encoding just the active part of the protein encoded by the full-length DNA sequence. A gene can be naturally occurring or synthetic.

As used herein, "truncated *B. thuringiensis* gene" should be understood as a fragment of a full-length *B. thuringiensis* gene which still encodes at least the toxic part of the *B. thuringiensis* ICP, preferentially the toxin.

As used herein, "marker gene" should be understood as a gene encoding a selectable marker (e.g., encoding antibiotic resistance) or a screenable marker (e.g., encoding a gene product which allows the quantitative analysis of transgenic plants).

Two ICPs are said to be "competitively binding ICPs" for a target insect species when one ICP competes for all ICP receptors of the other ICP, which receptors are present in the brush border membrane of the midgut of the target insect species.

Two ICPs are said to be "non-competitively binding ICPs" when, for at least one target insect species, the first ICP has at least one receptor for which the second ICP does not compete and the second ICP has at least one receptor for which the first ICP does not compete, which receptors are present in the brush border membrane of the midgut of the target insect species.

A "receptor" should be understood as a molecule, to which a ligand (here a *B. thuringiensis* ICP, preferably a toxin) can bind with high affinity (typically a dissociation constant (Kd) between $10^{-11}$ and $10^{-11}$ M) and saturability. A determination of whether two ICPs are competitively or non-competitively binding ICPs can be made by determining whether: 1. a first ICP competes for all of the receptors of a second ICP when all the binding sites of the second ICP with an affinity in the range of about $10^{-11}$ to $10^{-6}$ M can be saturated with the first ICP in concentrations of the first ICP of about $10^{-5}$ M or less (e.g., down to about $10^{-11}$ M); and 2. the second ICP competes for the all of the receptors of the first ICP when all the binding sites of the first ICP with an affinity in the range of about $10^{-11}$ to $10^{-6}$ M can be saturated with the second ICP in concentrations of the second ICP of about $10^{-5}$ M or less.

General Procedures

This section describes in broad terms general procedures for the evaluation and exploitation of at least two *B. thuringiensis* ICP genes for prevention of the development, in a target insect, of a resistance to the *B. thuringiensis* ICPs expressed in transgenic plants of this invention. A non-exhaustive list of consecutive steps in the general procedure follows, after which are described particular Examples that are based on this methodology and that illustrate this invention.

In accordance with this invention, specific *B. thuringiensis* ICPs can be isolated in a conventional manner from the respective strains such as are listed in Table 2 (which follows the Examples). The ICPs can be used to prepare monoclonal or polyclonal antibodies specific for these ICPs in a conventional manner (Hofte et al., 1988).

The ICP genes can each be isolated from their respective strains in a conventional manner. Preferably, the ICP genes are each identified by: digesting total DNA from their respective strains with suitable restriction enzyme(s); size fractionating the DNA fragments, so produced, into DNA fractions of 5 to 10 Kb; ligating such fractions to suitable cloning vectors (e.g., pEcoR251, deposited at the Deutsche Sammlung von Mikroorganismen und Zellculturen ("DSM"), Braunschweig, Federal Republic of Germany, under accession number no. 4711 on Jul. 13, 1988); transforming *E. coli* with the cloning vectors; and screening the clones with a suitable DNA probe. The DNA probe can be constructed from a highly conserved region which is commonly present in different *B. thuringiensis* genes which encode crystal protoxins against Coleoptera or Lepidoptera, such as on the basis of an N-terminal amino acid sequence determined by gas-phase sequencing of the purified proteins (EPA 88402115.5).

Alternatively, the desired fragments, prepared from total DNA of the respective strains, can be ligated in suitable expression vectors (e.g., a pUC vector (Yanisch-Perron et al., 1985) with the insert under the control of the lac promoter) and transformed in *E. coli*, and the clones can then be screened by conventional colony immunoprobing methods (French et al., 1986) for expression of the toxins with monoclonal or polyclonal antibodies raised against the toxins produced by the strains.

The isolated *B. thuringiensis* ICP genes can then be sequenced in a conventional manner using well-known procedures (e.g., Maxam and Gilbert, 1980).

At present, several ICP genes have been cloned from different subspecies of *B. thuringiensis* (Table 2). The nucleotide sequences from several of these *B. thuringiensis* ICP genes have been reported. Whereas several sequences are identical or nearly identical and represent the same gene or slight variants of the same gene, several sequences display substantial heterogeneity and show the existence of different *B. thuringiensis* ICP gene classes. Several lines of evidence suggest that all these genes specify a family of related insecticidal proteins. Analysis of the distribution of *B. thuringiensis* ICPs in different *B. thuringiensis* strains by determining the protein composition of their crystals, by immunodetection using polyclonal antisera or monoclonals against purified crystals, or by using gene-specific probes, shows that subspecies of *B. thuringiensis* might contain up to three related *B. thuringiensis* ICP genes belonging to different classes (Kronstad et al., 1983).

To express the isolated and characterized gene in a heterologous host for purification and characterization of the recombinant protein, the preferred organism is *Escherichia coli*. A number of expression vectors for enhanced expression of heterologous genes in *E. coli* have been described (e.g., Remaut et al., 1981). Usually the gene is cloned under control of a strong regulatable promoter, such as the lambda pL or pR promoters (e.g., Botterman and Zabeau, 1987), the lac promoter (e.g., Fuller, 1982) or the tac promoter (e.g., De Boer et al., 1983), and provided with suitable translation initiation sites (e.g., Stanssens et al, 1985 and 1987). Gene cassettes of the *B. thuringiensis* ICP genes can be generated by site-directed mutagenesis, for example-according to the procedure described by Stanssens et al. (1985 and 1987). This allows cassettes to be made comprising, for example, a truncated ICP gene fragment encoding the toxic core (i.e., toxin) of an ICP or a hybrid gene encoding the toxic core and a selectable marker according to the procedures described in EPA 88402241.9.

The cells of an *E. coli* culture, which has been induced to produce a recombinant ICP, are harvested. The method used to induce the cells to produce the recombinant ICP depends on the choice of the promoter. For example, the lac promoter (Fuller, 1982) is induced by isopropyl-B-D-thiogalacto-pyranoside ("IPTG"); the pL promoter is induced by temperature shock (Bernard et al., 1979). The recombinant ICP is usually deposited in the cells as insoluble inclusions (Hsuing and Becker, 1988). The cells are lysed to liberate the inclusions. The bulk of *E. coli* proteins is removed in subsequent washing steps. A semi-purified protoxin pellet is obtained, from which the protoxin can be dissolved in alkaline buffer (e.g., $Na_2CO_3$, pH 10). The procedure for the ICP Bt2, which is also applicable to other recombinant toxins, has been described by Hofte et al., 1986.

In accordance with this invention, the binding of various ICPs to ICP receptors on the brush border membrane of the columnar midgut epithelial cells of various insect species has been investigated. The brush border membrane is the primary target of each ICP, and membrane vesicles, preferentially derived from the brush border membrane, can be obtained according to Wolfersberger et al., 1987.

The binding to ICP receptors of one or more ICPs (e.g., ICP A, ICP B, etc.) can be characterized by the following steps (Hofmann et al, 1988b):

1. ICP A is labelled with a suitable marker (usually a radioisotope such as $^{125}I$).
2. Brush border membranes are incubated with a small amount (preferably less than $10^{-10}$ M) of labelled ICP A together with different concentrations of non-labelled ICP A (preferably from less than $10^{-11}$ to $10^{-5}$ M).
3. For all concentrations tested the amount of labelled ICP A bound to the brush border membranes is measured.
4. Mathematical analysis of these data allows one to calculate various characteristics of the ICP receptor such as the magnitude of the population of binding sites (Scatchard, 1949).
5. Competition by other toxins (e.g. ICP B) is preferably studied by incubating the same amount of labelled ICP A with brush border membranes in combination with different amounts of ICP B (preferentially from $10^{-11}$ to $10^{-6}$ M; and subsequently, steps 3 and 4 are repeated.

By this procedure, it has been found, for example, that Bt3 toxin, Bt2 toxin and Bt73 toxin are competitively binding anti-Lepidopteran ICPs for *Manduca sexta* and *Heliothis virescens* (See example 6 which follows). Various other combinations of toxins have been found to be non-competitively binding anti-Lepidopteran or anti-Coleopteran toxins (example 6).

Although the concept of competitivity versus non-competitivity of ICP binding does not have any practical importance by itself, the observation of the non-competitivity of two *B. thuringiensis* ICPs, active against the same target insect, can be put to very significant practical use. This is because a combination of two non-competitively binding *B. thuringiensis* ICPs can be used to prevent development, by a target insect, of resistance against such *B. thuringiensis* ICPs.

A selection experiment with *M. sexta*, using Bt2 toxin, Bt18 toxin, and a mixture of Bt2 and Bt18 toxins, has shown that Bt2 and Bt18 are two non-competitively binding anti-Lepidopteran toxins. After 20 generations of selection, a very pronounced reduction in ICP sensitivity was observed in the selection experiments with Bt2 or Bt18 alone (>100 times). The reduction in sensitivity in the selection experiment with a Bt2-Bt18 mixture was only marginal (3 times). This demonstrates the unexpected practical advantage of a simultaneous use of two non-competitively binding ICPs in a situation which models the high selection pressure which will exist with the use of transgenic plants transformed with ICP genes. In this regard, the two resistant strains showed a specific loss in receptor sites for either the Bt2 or Bt18 toxin. In each case, receptor sites for the toxin, which was not used for selection, were not affected or their concentration even increased. Thus, the Bt2 selected strain retained its Bt18 receptors, and the Bt18 selected strain developed an increased number of Bt2 receptors. Indeed, the Bt18 selected strain showed an increased sensitivity for Bt2 along with its increased Bt2 receptor concentration. No significant changes in receptor sites were found in the strain selected against the combined toxins. These findings are described in detail in Example 7 which follows.

A similar mechanism of resistance to Bt has been observed with respect to a strain of diamondback moth, *Plutella xylostella*. This strain had developed resistance in the field to Dipel which is a commercial formulation of the Bt HD-1 strain. Crystals of Dipel comprise a mixture of several BtICPs, similar to the Bt2, Bt3 and Bt73 proteins which are competitively-binding ICPs. As shown by both insect bioassays and competitive binding studies using Bt2 and Bt15, the Dipel-resistant diamondback moth strain is resistant to Bt2 protoxin and toxin but maintains full sensitivity to Bt15 protoxin and toxin. This finding is relevant to other combinations of non-competitively binding anti-Lepidopteran or Coleopteran ICPs which are expected to have the same beneficial effect against their common target insects.

Hence, a combination of non-competitively binding ICPs, when directly expressed in a transgenic plant, offers the substantial advantage of reducing the chances of development of insect resistance against the ICPs expressed in the plant. There may be additional benefits because the combined spectrum of two toxins may be broader than the spectrum of a single ICP expressed in a plant (See Examples 8, 9 and 10 which follow).

If, among two competitively binding ICPs, one has a larger binding site population than the other against a given target insect, it will be most advantageous to use the one with the larger population of binding sites to control the target pest in combination with the most suitable non-competitively binding *B. thuringiensis* ICP. For example, as seen from Example 6, it is preferred to use Bt73 against *Heliothis virescens*, rather than Bt2 or Bt3, and it is preferred to use Bt3 against *Manduca sexta* rather than Bt2 or Bt73. The selected gene can then be combined with the best suitable non-competitively binding ICP.

Previously, plant transformations involved the introduction of a marker gene together with a single ICP gene, within the same plasmid, in the plant genome (e.g., Vaeck et al., 1987; Fischoff et al., 1987). Such chimeric ICP genes usually comprised either all or part of an ICP gene, preferably a truncated ICP gene fragment encoding the toxic core, fused to a selectable marker gene, such as the neo gene coding for neomycin phosphotransferase. The chimeric ICP gene was placed between the T-DNA border repeats for *Agrobacterium* Ti-plasmid mediated transformation (EP 0193259).

This invention involves the combined expression of two or even more *B. thuringiensis* ICP genes in transgenic plants. The insecticidally effective *B. thuringiensis* ICP genes, encoding two non-competitively binding ICPs for a target insect species, preferably encoding the respective truncated ICP genes, are inserted in a plant cell genome, preferably in its nuclear genome, so that the inserted genes are downstream of, and under the control of, a promoter which can direct the expression of the genes in the plant cell. This is preferably accomplished by inserting, in the plant cell genome, one or more chimeric genes, each containing in the same transcriptional unit: at least one ICP gene; preferably a marker gene; and optionally a DNA sequence encoding a protease (e.g., trypsin)-sensitive or -cleavable protein part intercalated in frame between any two ICP genes in the chimaeric gene. Each chimaeric gene also contains at least one promoter which can direct expression of its ICP gene in the plant cell.

The selection of suitable promoters for the chimaeric genes of this invention is not critical. Preferred promoters for such chimaeric genes include: the strong constitutive 35S promoter obtained from the cauliflower mosaic virus, isolates CM 1841 (Gardner et al., 1981), CabbB-S (Franck et al., 1980) and CabbB-JI (Hull and Howell, 1987); the promoter of the nopaline synthetase gene ("PNOS") of the Ti-plasmid (Herrera-Estrella, 1983); the promoter of the octopine synthase gene ("POCS" {De Greve et al., 1982}); and the wound-inducible TR1' promoter and the TR2' promoter which drive the expression of the 1' and 2' genes, respectively, of the T-DNA (Velten et al., 1984). Alternatively, a promoter can be utilized which is specific for one or more tissues or organs of the plant, whereby the inserted genes are expressed only in cells of the specific tissue(s) or organ(s). Examples of such promoters are a stem-specific promoter such as the AdoMet-synthetase promoter (Peleman et al., 1989), a tuber-specific promoter (Rocha-Sosa et al., 1989), and a seed-specific promoter such as the 2S promoter (Krebbers et al., 1988). The ICP genes could also be selectively expressed in the leaves of a plant (e.g., potato) by placing the genes under the control of a light-inducible promoter such as the promoter of the ribulose-1,5-bisphosphate carboxylase small subunit gene of the plant itself or of another plant such as pea as disclosed in EP 0193259. Another alternative is to use a promoter whose expression is inducible (e.g., by temperature or chemical factors).

A 3' non-translated DNA sequence, which functions in plant cells for 3' end formation and the polyadenylation of the 3' end of the mRNA sequence encoded by the at least one ICP gene in the plant cell, also forms part of each such chimaeric gene. The selection of a suitable 3' non-translated DNA sequence is not critical. Examples are the 3' untranslated end of the octopine synthase gene, the nopaline synthase gene or the T-DNA gene 7 (Velten and Schell, 1985).

The selection of marker genes for the chimaeric genes of this invention also is not critical, and any conventional DNA sequence can be used which encodes a protein or polypeptide which renders plant cells, expressing the DNA sequence, readily distinguishable from plant cells not expressing the DNA sequence (EP 0344029). The marker gene can be under the control of its own promoter and have its own 3' non-translated DNA sequence as disclosed above, provided the marker gene is in the same genetic locus as the ICP gene(s) which it identifies. The marker gene can be, for example: a herbicide resistance gene such as the sfr or sfrv genes (EPA 87400141); a gene encoding a modified target enzyme for a herbicide having a lower affinity for the herbicide than the natural (non-modified) target enzyme, such as a modified 5-EPSP as a target for glyphosate (U.S. Pat. No. 4,535,060; EP 0218571) or a modified glutamine synthetase as a target for a glutamine synthetase inhibitor (EP 0240972); or an antibiotic resistance gene, such as a neo gene (PCT publication WO 84/02913; EP 0193259).

Using *A. tumefaciens* Ti vector-mediated plant transformation methodology, all chimaeric genes of this invention can be inserted into plant cell genomes after the chimaeric genes have been placed between the T-DNA border repeats of suitable disarmed Ti-plasmid vectors (Deblaere et al., 1988). This transformation can be carried out in a conventional manner, for example as described in EP 0116718, PCT publication WO 84/02913 and EPA 87400544.0. The chimaeric genes can also be in non-specific plasmid vectors which can be used for direct gene transfer (e.g., as described by Pazkowski et al., 1984; De La Pena et al., 1986). Different conventional procedures can be followed to obtain a combined expression of two *B. thuringiensis* ICP genes in transgenic plants as summarized below.

I Chimeric Gene Constructs whereby Two or More ICP Genes and a Marker Gene are Transferred to the Plant Genome as a Single Piece of DNA and Lead to the Insertion in a Single Locus in the Genome Ia The Genes can be Engineered in Different Transcriptional Units Each Under Control of a Distinct Promoter To express two or more ICP genes and a marker gene as separate transcriptional units, several promoter fragments directing expression in plant cells can be used as described above. All combinations of the promoters mentioned above in the chimaeric constructs for one ICP gene are possible. Examples of such individual chimeric constructs are described for the bt2 gene in EP 0193259, for the bt13 gene in EPA 88402115.5 and for the bt18 gene in EPA 88402241.9. The ICP gene in each chimeric gene of this invention can be the intact ICP gene or preferably an insecticidally-effective part of the intact ICP gene, especially a truncated gene fragment encoding the toxic core of the ICP. The individual chimeric genes are cloned in the same plasmid vector according to standard procedures (e.g., EP 0193259).

Ib Two Genes (e.g., Either an ICP and a Marker Gene or Two ICP Genes) or More can be Combined in the Same Transcriptional Unit To express two or more ICP genes in the same transcriptional unit, the following cases can be distinguished:

In a first case, hybrid genes in which the coding region of one gene is in frame fused with the coding region of another gene can be placed under the control of a single promoter. Fusions can be made between either an ICP and a marker gene or between two ICP genes. An example of an ICP gene-marker gene fusion has been described in EP 0193259 (i.e., a hybrid truncated bt2-neo gene encoding a Bt2 toxin-NPTII fusion protein).

Another possibility is the fusion of two ICP genes. Between each gene encoding an ICP which still is insecticidally active (i.e., a toxic part of the protoxin), a gene fragment encoding a protease (e.g., trypsin)—sensitive protein part should be included, such as a gene fragment encoding a part of the N-terminal or C-terminal amino acid sequence of one of the ICPs which is removed or cleaved upon activation by the midgut enzymes of the target insect species.

In a second case, the coding regions of the two respective ICP genes can be combined in dicistronic units placed under the control of a promoter. The coding regions of the two ICP genes are placed after each other with an intergenic sequence of defined length. A single messenger RNA molecule is generated, leading to the translation into two separate gene products. Based on a modified scanning model (Kozak, 1987), the concept of reinitiation of translation has been accepted provided that a termination codon in frame with the upstream ATG precedes the downstream ATG. Experimental data also demonstrated that the plant translational machinery is able to synthesize several polypeptides from a polycistronic mRNA (Angenon et al., 1989).

II Chimeric Constructs with One or More ICP Genes that are Transferred to the Genome of a Plant Already Transformed with a One or More ICP Genes Several genes can be introduced into a plant cell during sequential transformation steps (retransformation), provided that an alternative system to select transformants is available for the second round of transformation. This retransformation leads to the combined expression of ICP genes which are introduced at multiple loci in the genome. Preferably, two different selectable marker genes are used in the two consecutive transformation steps. The first marker is used for selection of transformed cells in the first transformation, while the second marker is-used for selection of transformants in the second round of transformation. Sequential transformation steps using kanamycin and hygromycin have been described, for example by Sandler et al. (1988) and Delauney et al. (1988).

III Chimeric Constructs with One or More ICP Genes, that are Separately Transferred to the Nuclear Genome of Separate Plants in Independent Transformation Events and are Subsequently Combined in a Single Plant Genome Through Crosses The first plant should be a plant transformed with a first ICP gene or an F1 plant derived herefrom through selfing (preferably an F1 plant which is homozygous for the ICP gene). The second plant should be a plant transformed with a second ICP gene or an F1 plant derived herefrom through selfing (preferably an F1 plant which is homozygous for the second ICP gene). Selection methods can be applied to the plants obtained from this cross in order to select those plants having the two ICP genes present in their genome (e.g., Southern blotting) and expressing the two ICPs (e.g., separate ELISA detection of the immunologically different ICPs). This is a useful strategy to produce hybrid varieties from two parental lines, each transformed with a different ICP gene, as well as to produce inbred lines containing two different ICP genes through crossing of two independent transformants (or their F1 selfed offspring) from the same inbred line.

IV Chimeric Constructs with One or More ICP Genes Separately Transferred to the Genome of a Single Plant in the Same Transformation Experiment Leading to the Onsertion of the Respective Chimeric Genes at Multiple Loci Cotransformation involves the simultaneous transformation of a plant with two different expression vectors, one containing a first ICP gene, the second containing a second ICP gene. Along with each ICP gene, a different marker gene can be used, and selection can be made with the two markers simultaneously. Alternatively, a single marker can be used, and a sufficiently large number of selected plants can be screened in order to find those plants having the two ICP genes (e.g., by Southern blotting) and expressing the two proteins (e.g., by means of ELISA). Cotransformation with more than one T-DNA can be accomplished by using simultaneously two different strains of *Agrobacterium*, each with a different Ti-plasmid (Depicker et al., 1985) or with one strain of *Agrobacterium* containing two T-DNAs on separate plasmids (de Framond et al., 1986). Direct gene transfer, using a mixture of two plasmids, can also be employed to cotransform plant cells with a selectable and a non-selectable gene (Schocher et al., 1986).

The transgenic plant obtained can be used in further plant breeding schemes. The transformed plant can be selfed to obtain a plant which is homozygous for the inserted genes. If the plant is an inbred line, this homozygous plant can be used to produce seeds directly or as a parental line for a hybrid variety. The gene can also be crossed into open pollinated populations or other inbred lines of the same plant using conventional plant breeding approaches.

Of course other plant transformation methods can be used and are within the scope of the invention as long as they result is a plant which expresses two or more non-competitively binding ICPs. In this regard, this invention is not limited to the use of *Agrobacterium* Ti-plasmids for transforming plant cells with genes encoding non-competitively binding ICPs. Other known methods for plant cell transformations, such as electroporation or by the use of a vector system based on plant viruses or pollen, can be used for transforming monocotyledonous and dicotyledonous plants in order to obtain plants which express two non-competitively binding ICPs. Furthermore, DNA sequences encoding two non-competitively binding ICPs other than those disclosed herein can be used for transforming plants. Also, each of the ICP genes, described herein, can be encoded by equivalent DNA sequences, taking into consideration the degeneracy of the genetic code. Also, equivalent ICPs with only a few amino acids changed, such as would be obtained through mutations in the ICP gene, can also be used, provided they encode a protein with essentially the same characteristics (e.g., insecticidal activity and receptor binding).

The following Examples illustrate the invention. Those skilled in the art will, however, recognize that other combinations of two or more non-competitively binding *B. thuringiensis* ICP genes can be used to transform plants in accordance with this invention in order to prevent the development, in a target insect, of resistance to *B. thuringiensis* ICPs expressed in the transformed plants. Unless otherwise indicated, all procedures for making and manipulating DNA were carried out by the standardized procedures described in Maniatis et al, Molecular Cloning—A Laboratory Manual, Cold Spring Harbor Laboratory (1982).

EXAMPLE 1

Collection of Genes

The collection of anti-Lepidopteran and anti-Coleopteran Bt genes encoding ICPs, which are the subject of the Examples, is described in Table 2 (following the Examples). References for the respective genes are indicated in Table 2. The origin, the isolation and characterization of the Bt genes, which have not been published, are described below. Bt strains, such as strains HD-1, HD-68, HD-110, and HD-73, are publicly available from the Agricultural Research Culture Collection, Northern Regional Research Laboratory, U.S. Dept. of Agriculture, Peoria, Ill. 61604, U.S.A.

bt3 gene: From *B. thuringiensis* var. *kurstaki* HD-1, the ICP was cloned. Characterization of this gene revealed an open reading frame of 3528 bp which encodes a protoxin of 133 kDa. This gene was identical to the one described by Schnepf et al. (1985).

bt73 gene: From *B. thuringiensis* var HD-73. The ICP gene was cloned as described by Adang et al. (1985).

bt4 gene: A genomic library was prepared from total DNA of strain *B. thuringiensis aizawai* HD-68. Using the 1.1 kb internal HindIII fragment of the bt2 gene as a probe, a gene designated bt4 was isolated. Characterization of this gene revealed an open reading frame of 3495 bp which encodes a protoxin of 132 kDa and a trypsin activated toxin fragment of 60 kDa. This (insect controlling protein) gene differs from previously identified genes and was also found in several other strains of subspecies *aizawai* and *entomocidus* including HD-110. FIG. 13 shows the nucleotide sequence and deduced amino acid sequence of the open reading frame ("ORF") of the bt4 gene extending from nucleotide 264 to nucleotide 3761 (SEQ ID NO: 5).

bt14 and bt15 genes: A genomic library was prepared from total DNA of strain *B. thuringiensis* var. *entomocidus* HD-110 by partial Sau3A digest of the total DNA and cloning in the vector pEcoR251 (deposited at DSM under accession number 4711). Using monoclonal antibodies (Hofte et al., 1988), at least three structurally distinct ICPs were identified in crystals of *B. thurinciens* is *entomocidus* HD-110. These monoclonal antibodies were used to clone the three different ICP genes from this *B. thuringiensis* strain. One of these genes is the bt4 gene as described above.

The second gene was called "bt15". FIG. 14 shows the nucleotide sequence and deduced amino acid sequence of the ORF of the bt15 gene, isolated from HD-110, extending from nucleotide 234 to nucleotide 3803 (SEQ ID NO: 7). The Shine and Dalgarno sequence, preceding the initiation codon is underlined. This gene has an open reading frame of 3567 bp which encodes a protoxin of 135 kDa and a 63 kDa toxin fragment. A similar gene has been described by Honee et al. 1988, isolated from *B. thuringiensis entomocidus* 60.5. The bt15 gene differs from the published sequence at three positions: an Ala codon (GCA) is present instead of an Arg codon (CGA) at position 925 and a consecution of a Thr-His codon (ACGCAT) is present instead of a Thr-Asp codon (ACCGAT) at position 1400. (The numbers of the positions are according to Honnee et al., 1988). Another similar gene has been described in EP 0295156, isolated from *B. thuringiensis aizawai* 7-29 and *entomocidus* 6-01. The bt15 gene is different from this published nucleotide sequence at three different places: 1) a Glu codon (GAA) instead of an Ala codon (GCA) at (position. 700; 2) the sequence (SEQ ID NO:1) TGG, CCA, GCG, CCA instead of (SEQ ID NO:2) TGC, CAG, CGC, CAC, CAT at position 1456 and 3) an Arg codon (CGT) instead of an Ala codon (GCG) at position 2654. (The numbers of the positions are according to EP 0295156).

The third gene isolated was called "bt14". It has an open reading frame of 3621 bp which encodes a 137 kDa protoxin and a 66 kDa activated toxin fragment. A similar gene has been cloned from *B. thuringiensis* HD-2 (Brizzard and Whiteley, 1988). The bt14 gene differs from the published nucleotide sequence by two nucleotide substitutions: a T instead of a C at position 126, and a C instead of a T at position 448 (the numbers of the positions are according to Brizzard and Whiteley, 1988). In the first case, the Ile codon (ATT or ATC) is conserved whereas in the second case the Tyr codon (TAT) is converted to a His codon (CAC).

bt2 gene: The bt2 gene was cloned as described in EP 0193259.

bt18 gene: Cloning of the bt18 gene was performed as described in EPA 88402241.9.

bt13 gene: The bt13 gene was cloned as described in EPA 88402115.5.

bt21 and bt22 genes: These genes, encoding Coleopteran-active ICPs, were cloned as described in EPA 89400428.2.

EXAMPLE 2

Construction of Gene Cassettes and Expression of Bt genes in *E. coli*

1) bt2, bt18: the construction of bt2 and bt18 gene cassettes has been previously described in EPA 86300291.1 and 88402241.9, respectively. Basically, they comprise a truncated gene encoding the toxic core and a hybrid gene comprising the truncated gene fused in frame to the N-terminus of the neo gene. The gene cassettes are used to transform *E. coli* to express the Bt2 and Bt18 ICP toxins.

2) bt14, bt15: as described in EPA 88402241.9, gene cassettes for the bt14 and bt15 genes were constructed in order to express the genes in *E. coli* and in plants.

First, a NcoI site was introduced at the N-terminus of the genes by site-directed mutagenesis.

In the case of the bt15 gene, the conversion of the TT nucleotides, immediately in front of the ATG codon, into CC yielded a NcoI site overlapping with the ATG initiation codon. This site was introduced using the pMa/c vectors for site-directed mutagenesis (Stanssens et al., 1987) and a 28-mer oligonucleotide with the following sequence (SEQ ID NO.:3): 5'-CGGAGGTATTCCATGGAGGAAAATAATC-3'.

This yielded the plasmid pVE29 carrying the N-terminal fragment of the bt15 gene with a NcoI site at the ATG initiation codon.

According to Brizzard and Whiteley (1988), the initiation codon of the bt14 gene is a TTG codon. Thus, a NcoI site was created in a like manner at this codon for site directed mutagenesis using a 34-mer oligonucleotide with the following sequence (SEQ ID NO.:4): 5'-CCTATTTGAAGCCATG-GTAACTCCTCCTTTTATG-3'.

In this case the sequence of the intitiation codon was converted from ATATTGA to ACCATGG. This yielded the plasmid pHW44 carrying the N-terminal fragment of the bt14 gene with a NcoI site at the initiation codon.

In a second step, the genes were reconstructed by ligating the N-terminal gene fragments with a suitable C-terminal gene fragment, yielding a bt15 gene- and bt14 gene with a NcoI site at the ATG initiation codon.

To express the bt14 and bt15 genes encoding the protoxin in E. coli, the following constructs were made: pOH50 containing the bt15 gene under the control of the lac promoter; and pHW67 containing the bt14 gene under the control of the tac promoter. Induction of a culture of the E. coli strain WK6 carrying the respective plasmids with IPTG yielded an overproduced protein (Fuller, 1982).

The active toxic fragments of the Bt15 and Bt14 protoxins comprise 63 and 60 kDa trypsin digest products respectively. Instead of expressing the whole bt15 or bt14 gene, it is also possible to express a toxin-encoding gene fragment or derivative thereof in plants. To this end, truncated bt14 and bt15 gene fragments were constructed. In order to be able to select transgenic plants producing the ICP gene products, hybrid genes of the truncated gene fragments were also made with the neo gene encoding a selectable marker as described in EP 0193259.

By comparison of the nucleotide sequence of the bt4, bt14 and bt15 genes, respectively, with the bt2 and bt18 genes, respectively, the BclI site could be identified as a suitable site localized downstream of the coding sequence encoding the toxin gene fragment. To construct a truncated gene fragment and a hybrid gene of the truncated gene fragment with the neo gene, the filled BclI site was ligated to the filled EcoRI site of pLKM91 (Hofte et al., 1986) and the filled HindIII site of pLK94 respectively (Botterman and Zabeau, 1987). pLKM91 carries a 5' truncated neo gene fragment which codes for an enzymatically active C-terminal gene fragment of the neo gene, and pLK94 contains translation stop codons in three reading frames. This yielded the following plasmids which are then used to transform E. coli to express the ICP genes: pHW71 carrying a truncated bt14-neo hybrid gene; pHW72 carrying a truncated bt14 gene; pVE34 carrying a truncated bt15-neo hybrid gene; and pVE35 carrying a truncated bt15 gene.

In a similar way as described for the bt14 and bt15 genes, gene cassettes are constructed for the bt3 and bt4 genes which are then expressed in E. coli.

EXAMPLE 3

Purification of Recombinant ICPs

The ICPs expressed in E. coli in Example 2 are purified by the method (described for recombinant Bt2 protoxin) by Hofte et al. (1986).

EXAMPLE 4

Purification of Toxins

Solubilized protoxins of Bt2, B3, B73, B4, Bt14, Bt15, Bt18, Bt13, Bt21 and Bt22 (in $Na_2CO_3$ 50 mM, DTT 10 mM pH=10) are dialyzed against 0.5% $(NH_4)_2CO_3$ at pH 8 and treated with trypsin (trypsin/protoxin=1/20 w/w) for 2 h at 37° C. The activated toxin is chromatographically purified (Mono-Q column on FPLC) as described by Hofmann et al. (1988b).

EXAMPLE 5

Determination of the Insecticidal Spectrum

The ICP protoxins and toxins of Examples 3 and 4 are evaluated for their insecticidal activity. Each protoxin is dissolved in alkaline buffer containing a reducing agent ($Na_2CO_3$ 50 mM, DTT 10 mM pH=10), and each toxin is used as soluble protein directly from FPLC. Protein concentrations are determined. Subsequently, dilutions of the resulting protoxin or toxin solution are prepared in PBS buffer pH=7.4 containing 0.15 M NaCl and 0.1% bovine serum albumin ("BSA").

The artificial medium for insect culture, described by Bell and Joachim (1976) for *Manduca sexta*, is poured in appropriate receptacles and allowed to solidify. Subsequently a quantity of the (pro)toxin dilutions is applied on this medium, and the water is allowed to evaporate under a laminar flow. This results in a medium with a certain quantity (in the range of 0.1 to 10000 ng/cm2) of toxin coated on its surface. For example, for the Bt2 toxin, typical dilutions for a toxicity test on *Manduca sexta* are 1, 5, 25, 125 and 625 ng/cm2. First instar larvae of *Manduca sexta* are then applied on the coated medium, and growth and mortality are assessed after 6 days. Mortality increases with dosage. Dose response data is analysed in probit analysis (Finney, 1962), and the data are best summarized by an $LD_{50}$ value which is the amount of toxin which kills 50% of the insects. The $LD_{50}$ for Bt2 toxin against *Manduca sexta* is around 20 ng/cm2.

Similar assays are carried out for other insect species using a suitable diet or by applying the ICPs on leaves for insects, for which no artificial diet is used.

EXAMPLE 6

Binding Studies

Toxins All protoxins and their toxic fragments were purified according to the methods described for the Bt2 protoxin and toxin in Hofte et al. (1986) and EP 0193259. The activated and purified toxins are further referred to as the Bt2, Bt3, Bt73, Bt4, Bt14, B15, Bt18, Bt13, Bt21 and Bt22 toxins.

By way of example for the Bt73 toxin, it has been shown that *B. thuringiensis* var. *kurstaki* HD73 produces a protein of 133 kDa encoded by a 6.6 kb type gene. A culture of this strain was grown as described by Mahillon and Delcour (1984). The autolysed culture was spun down (20 minutes at 4500 rpm in a HB4 rotor) and washed with a buffer containing 20 mM Tris, 100 mM NaCl and 0.05% Triton X-100, pH 8. The final pellet was resuspended in this buffer (4 ml buffer for 100 ml culture). This solution was then layered onto a linear Urograffin gradient (60-70%) which was centrifuged in a SW 28 rotor for 90 minutes at 18000 rpm. Crystals were collected and stored at −20° C. until further use. Activation was performed according to Hofte et al. (1986). The purified toxin is further referred to as the Bt73 toxin.

Iodination of ICPs

Iodination of Bt2, Bt3, and Bt73 toxins was performed using the Chloramin-T method (Hunter and Greenwood, 1962). 1 mCi $^{125}$I-NaI and 20 to 37.5 ug Chloramin-T in NaCl/$P_i$ were added to 50 ug of purified toxin. After gentle shaking for 60 seconds, the reaction was stopped by adding 53 ug of potassium metabisulfite in $H_2O$. The whole mixture was loaded on a PD 10 Sephadex G-25M gelfiltration column to remove free iodine. A subsequent run on a Biogel P-60 column was carried out in order to increase the purity.

Alternatively, toxins were labeled using the Iodogen method. Iodogen (Pierce) was dissolved in chloroform at 0.1 mg/ml. 100 ul of this solution was pipetted into a disposable glass vessel and dried under a stream of nitrogen gas. The vessel was rinsed with Tris buffer (20 mM Tris, pH 8.65 with 0.15 M NaCl). 50 ug of toxin (in Tris buffer) was incubated with 1 mCi of $^{125}$I-NaI in the tube for 10 minutes. The reaction was then stopped by the addition of 1 M NaI (one fourth of the sample volume). The sample was immediately loaded onto a PD10 Sephadex G-25M column and later on a Biogel P-60 column to remove free iodine and possible degradation products. Other toxins were iodinated using one of the above mentioned procedures.

Determination of Specific Activity of Iodinated Toxin

Specific activity of iodinated Bt2, B3, and Bt73 toxin samples was determined using a "sandwich" ELISA technique according to Voller, Bidwell and Barlett (1976). Primary antibody was a polyclonal antiserum raised against Bt2 toxin, and the secondary antibody was a monoclonal antibody 4D6.

The conjugate used was alkaline phosphatase coupled to anti-mouse IgG. The reaction intensity of a standard dilution series of unlabeled toxin and dilutions of the iodinated toxin sample (in NaCl/$P_i$-0.1% BSA) was measured. Linear regression calculations yielded the protein content of the radioactive toxin sample. The samples with the highest specific activities were used in the binding assays. Specific activities were 59400, 33000 and 19800 Ci/mole (on reference date) for Bt73 toxin (labeled according to Iodogen procedure), Bt2 toxin (Chloramin-T method) and Bt3 toxin (Iodogen method) respectively.

Specific activities of other toxins were determined using a similar approach. Specific monoclonal and polyclonal antibodies for each of these toxins were raised and applied in ELISA.

Preparation of Brush Border Membrane Vesicles

Brush border membrane vesicles ("BBMV") from *Manduca sexta*, *Heliothis virescens*, *Plutella xylostella*, *Phthorimaea operculella*, *Spodoptera exigua*, *Spodoptera littoralis*, *Plodia interpunctella*, *Mamestra brassicae*, *Pieris brassicae* and *Leptinotarsa decemlineata* were prepared according to the method of Wolfersberger et al. (1987). This is a differential centrifugation method that makes use of the higher density of negative electrostatic charges on luminal than on basolateral membranes to separate these fractions.

Binding Assay

Duplicate samples of $^{125}$I-labeled toxin, either alone or in combination with varying amounts of unlabeled toxin, were incubated at the appropriate temperature with brush border membrane vesicles in a total volume of 100 ul of Tris buffer (Tris 10 mM, 150 mM NaCl, pH 7.4). All buffers contained 0.1% BSA. The incubation temperature was 20 C. Ultrafiltration through Whatman GF/F glass fiber filters was used to separate bound from free toxin. Each filter was rapidly washed with 5 ml of ice-cold buffer (NaCl/$P_i$-0.1% BSA). The radioactivity of the filter was measured in a gamma-counter (1275 Minigamma, LXB). Binding data were analyzed using the LIGAND computer program. This program calculates the bound concentration of ligand as a function of the total concentration of ligand, given the affinity (Ka or its inverse Kd=1/Ka, the dissociation constant) and the total concentration of receptors or binding site concentration ($R_t$).

Determination of Protein Concentration

Protein concentrations of purified Bt2, B3, B73 and Bt15 toxins were calculated from the OD at 280 nm (measured with a Uvikon 810 P, Kontron Instruments spectrofotometer). The protein content of solutions of other toxins and of brush border membrane vesicles (BBMV) as measured according to Bradford (1976). Binding of Bt2, Bt3 and Bt73 Toxins to BBMV of *Manduca sexta* and *Heliothis virescens*: an Example of 3 Competitively Binding Lepidopteran ICPs.

Bt2, Bt3 and Bt73 toxins are toxic to both *Manduca sexta* and *Heliothis virescens*: LC50 values for *Manduca sexta* are respectively 17.70, 20.20 and 9.00 ng/cm2; for *Heliothis virescens* the $LC_{50}$'s are 7.16, 90.00 and 1.60 ng/cm2.

Labelled toxin, either Bt3 (0.8 nM) or Bt2 (1.05 nM) or Bt73 (1.05 nM), was incubated with BBMV in a volume of 0.1 ml. BBMV protein concentrations were 100 ug/ml for *M. sexta* and for Bt2-*H. virescens*, for Bt3-*H. virescens* 150 and for Bt73-*H. virescens* 50 ug/ml. The labelled toxin was combined with varying amounts of an unlabeled toxin (competitor). After a 30 min. incubation, bound and free toxins were separated through filtration.

Figure 1:
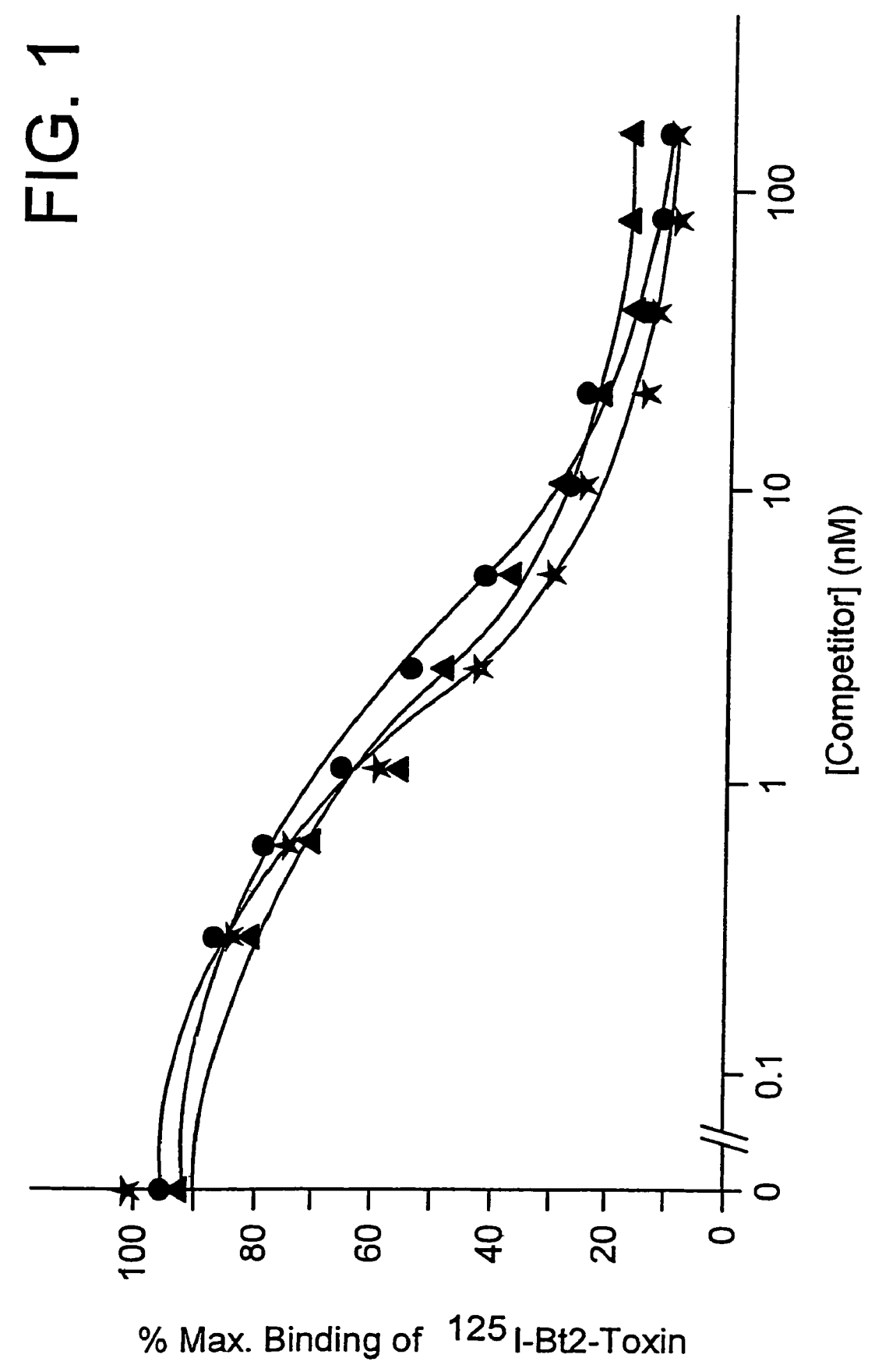
Figure 2:
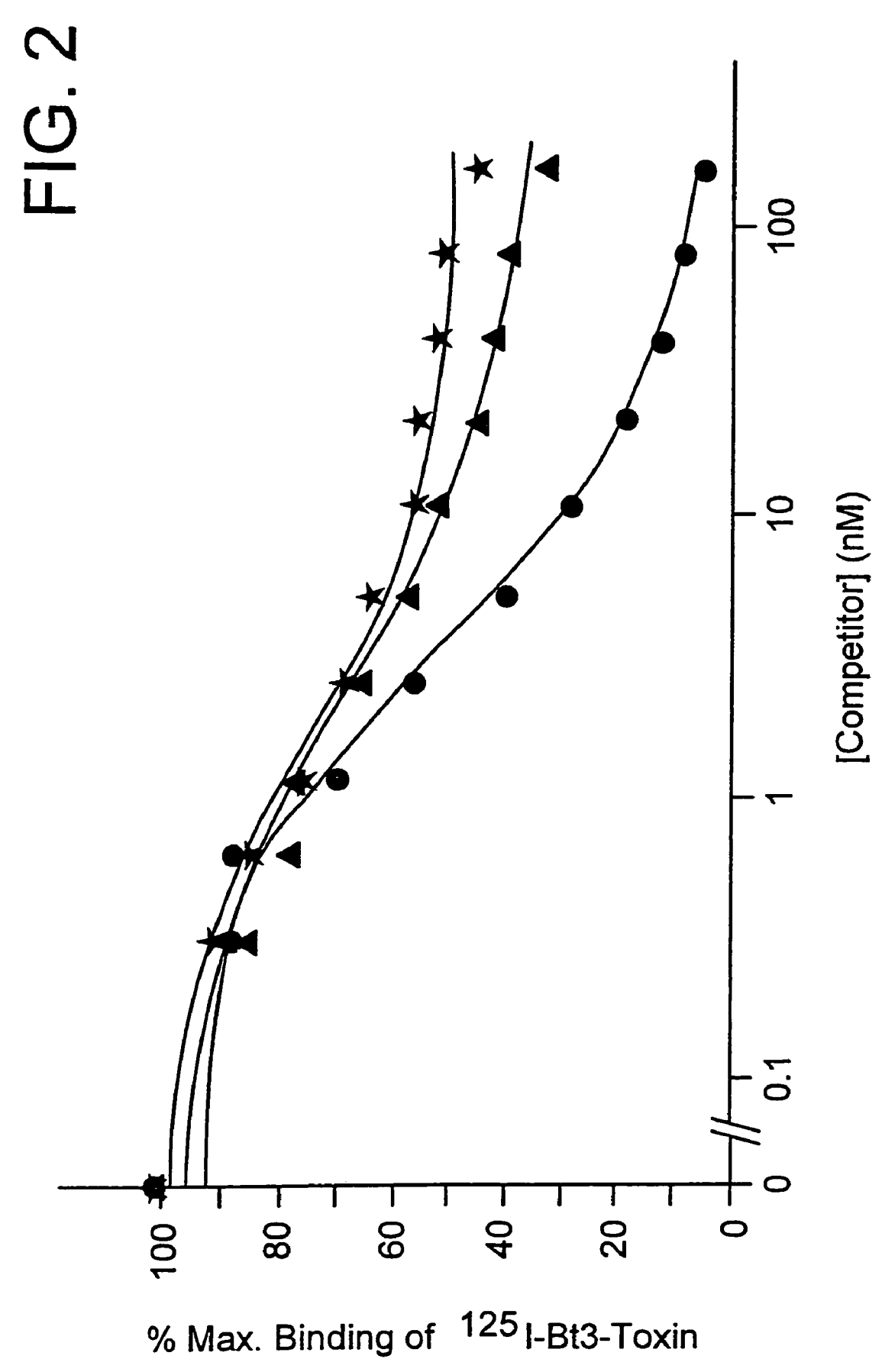
Figure 4:
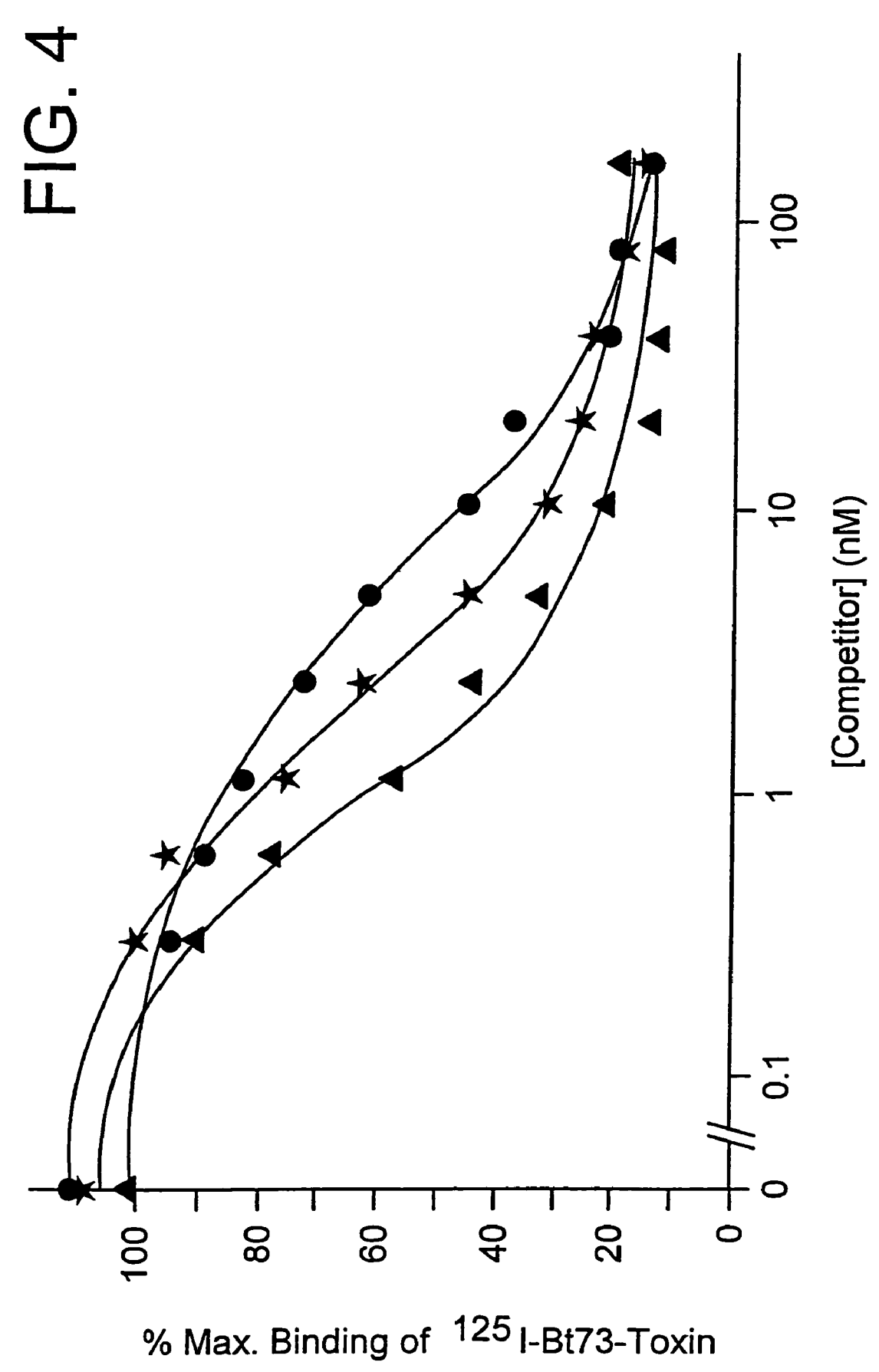
Figure 5:
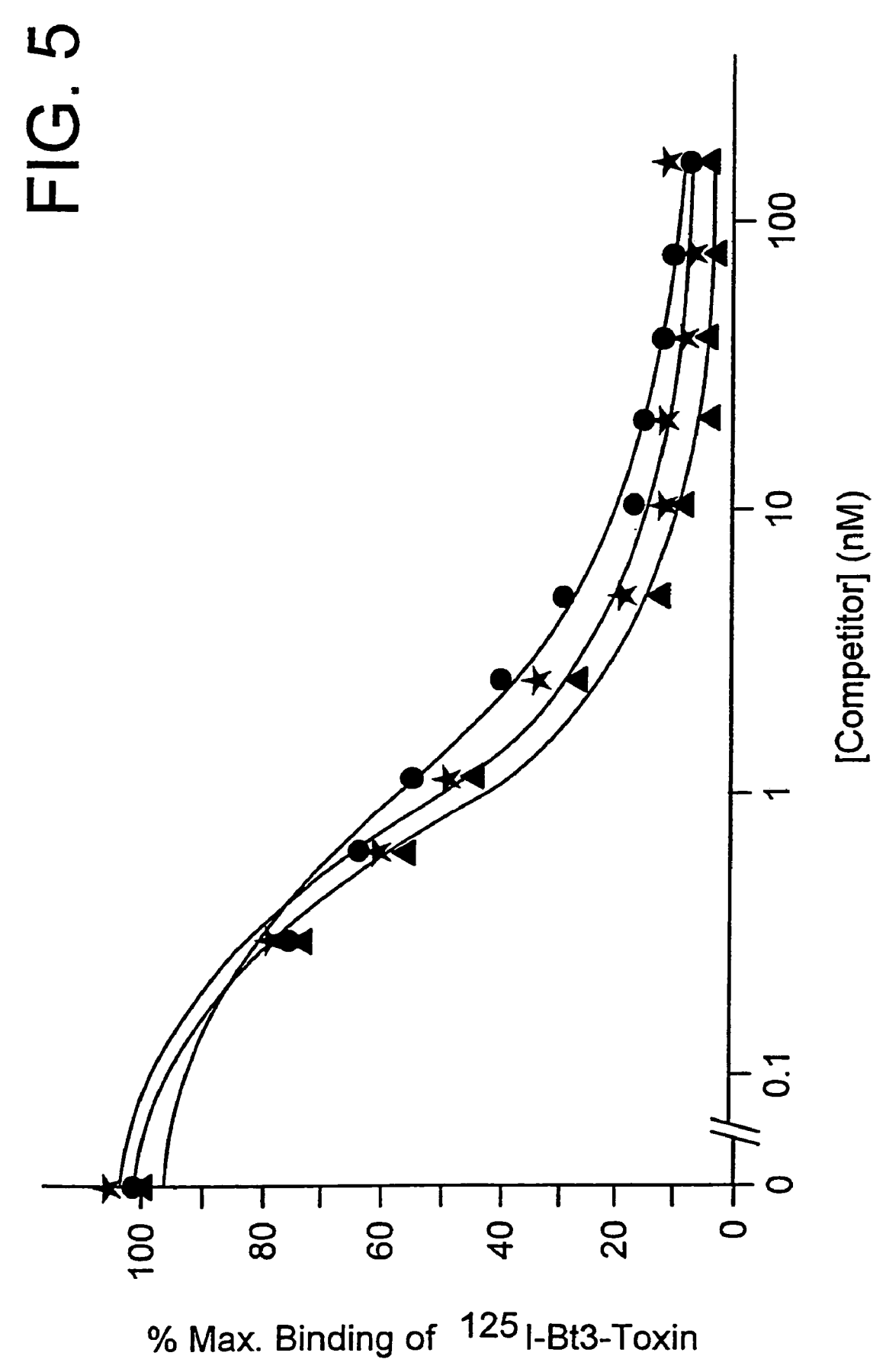
Figure 6:
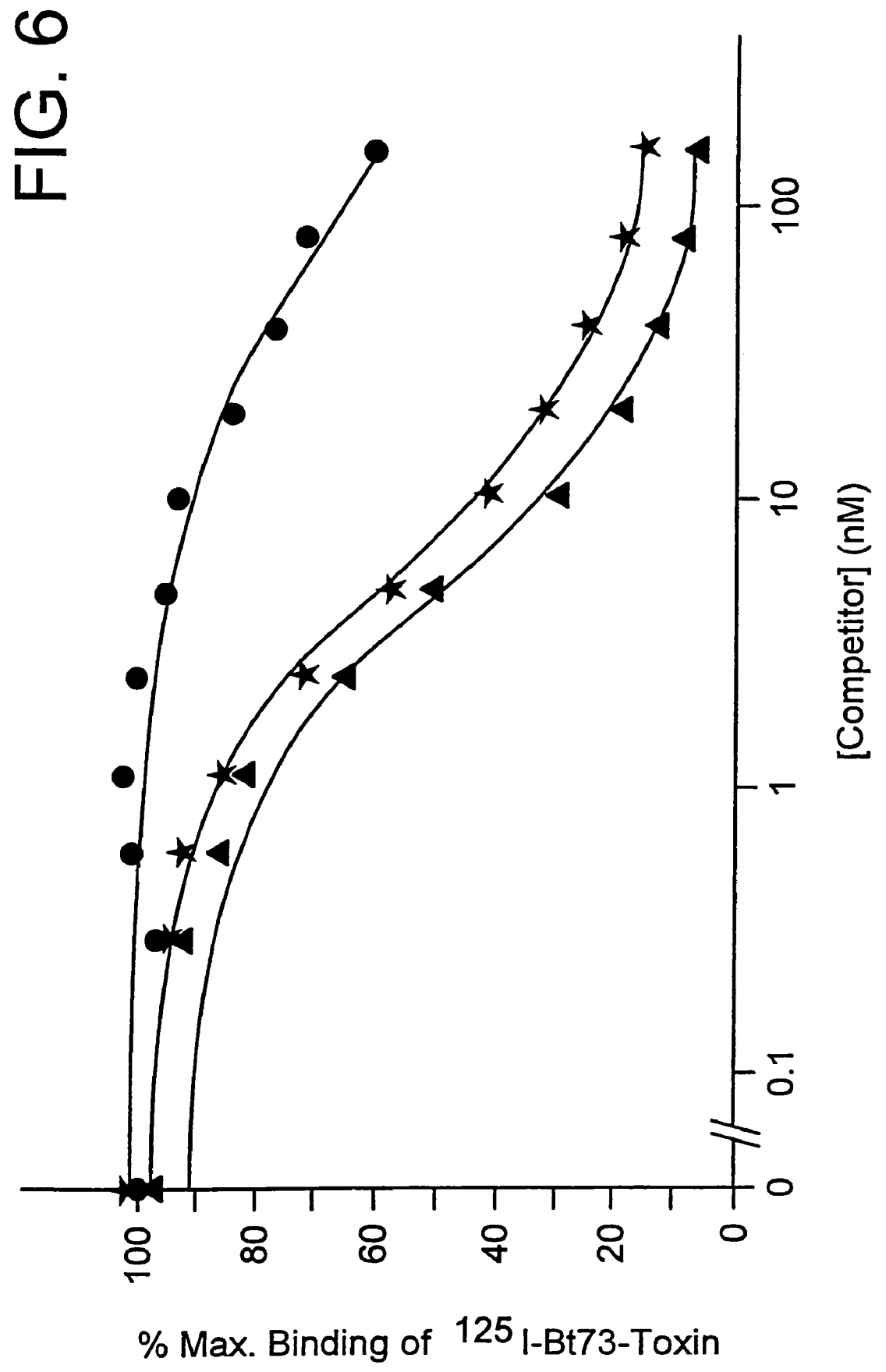

FIGS. 1-3 show the percentages binding of respectively labelled Bt2, B3 and Bt73 toxins as a function of the concentration of competitor for *Manduca sexta*. FIGS. 4-6 show these data for *Heliothis virescens*. The amount bound in the absence of competitor is always taken as 100% binding. FIGS. 1-6 show the binding of $^{125}$I-labeled toxins to *M. sexta* (in FIGS. 1, 2 and 3) and *H. virescens* (in FIGS. 4, 5 and 6) brush border membrane vesicles. Vesicles were incubated with labeled toxin {in FIGS. 1 and 4: $^{125}$I-Bt2-toxin (1.05 nM); in FIGS. 2 and 5: $^{125}$I-Bt3-toxin (0.8 nM); in FIGS. 3 and 6: $^{125}$I-Bt73-toxin (1.05 nM)} in the presence of increasing concentrations of Bt2 toxin (*), Bt3 toxin (●) or Bt73 toxin (▲). Binding is expressed as percentage of the amount bound upon incubation with labeled toxin alone. On *M. sexta* vesicles, these amounts were 1820, 601 and 2383 cpm, and on *H. virescens* vesicles 1775, 472 and 6608 cpm for $^{125}$I-Bt2-, Bt3- and Bt73-toxin, respectively. Non-specific binding was not substracted. Data were analyzed with the LIGAND computer program. Each point is the mean of a duplicate sample.

FIG. 1: shows the binding of $^{125}$I Bt2 toxin to *M. sexta* BBMV

FIG. 2: shows the binding of $^{125}$I Bt3 toxin to -*M. sexta* BBMV

FIG. 3: shows the binding of $^{125}$I Bt73 toxin to *M. sexta* BBMV

FIG. 4: shows the binding of $^{125}$I Bt2 toxin to *H. virescens* BBMV

FIG. 5: shows the binding of $^{125}$I Bt3 toxin to *H. virescens* BBMV

FIG. 6: shows the binding of $^{125}$I Bt73 toxin to *H. virescens* BBMV

The conclusions from FIGS. 1-6 are that Bt2 and Bt3, B3 and Bt73, and Bt2 and Bt73 are competitively-binding ICP's both for *Manduca sexta* and for *Heliothis virescens*. Indeed Bt3 competes for the entire population of receptor sites of Bt2 in *Manduca sexta* (FIG. 1): the % labelled Bt2 bound in the presence of 100 nm Bt3 is equal to the % Bt2 bound with 100 nM of Bt2 itself. The opposite is not true: in the presence of 100 nM Bt2 the % of labelled Bt3 is not reduced to the same level as with 100 nM of Bt3 (FIG. 2).

A similar reasoning is followed to observe competitivity of other toxin combinations: Bt3 competes for the entire population of receptor sites of Bt73 (FIG. 3) in *M. sexta*; the opposite is not true (FIG. 2); Bt2 and Bt73 compete for the entire population of each other's binding sites in *M. sexta* (FIGS. 1 and 3).

In *Heliothis virescens*: Bt2 competes for the entire population of receptor sites of Bt3 (FIG. 5); Bt73 competes for the entire population of receptor sites of Bt3 (FIG. 5); Bt73 competes for the entire population of receptor sites of Bt2 (FIG. 4); but the opposite statements are not true (FIGS. 4, 5 and 6).

The same data can be used in mathematical analysis (e.g., Scatchard analysis according to Scatchard, 1949; analysis with the LIGAND computer program according to Munson and Rodbard, 1980) to calculate the dissociation constant (Kd) of the toxin-receptor complex and the concentration of binding sites (Rt); the results of these calculations using the LIGAND computer program were the following:

| | | |
|---|---|---|
| Bt2-*M. sexta*: protein | Kd = 0.4 nM | Rt = 3.4 pmol/mg vesicle |
| Bt3-*M. sexta*: protein | Kd = 1.5 nM | Rt = 9.8 pmol/mg vesicle |
| Bt73-*M. sexta*: protein | Kd = 0.6 nM | Rt = 4.0 pmol/mg vesicle |
| Bt2-*H. virescens*: protein | Kd = 0.6 nM | Rt = 9.7 pmol/mg vesicle |
| Bt3-*H. virescens*: protein | Kd = 1.2 nM | Rt = 3.7 pmol/mg vesicle |
| Bt73-*H. virescens*: protein | Kd = 0.8 nM | Rt = 19.5 pmol/mg vesicle |

These data demonstrate the high affinity receptor binding of the toxins (Kds in the range of $10^{-10}$ to $10^{-9}$ M.

Binding of Bt2 and Bt14 Toxins to BBMV of *P. brassicae*, *Plutella xylostella* and *Phthorimaea opercullela*: an Example Two Non-competitively Binding Lepidopteran ICPs Bt2 and Bt14 toxins are toxic to *P. brassicae* (p.b.), *P. xylostella* (p.x.) and *P. operculela* (p.o.) as seen from the table below.

| | $C_{50}$ of Toxins | |
|---|---|---|
| | Bt2 | Bt14 |
| P.b. | 1.3 | 2.0 |
| P.x. | 6.7 | 5.4 |
| P.o. | 4.20 | 0.8-4.0 |

$LC_{50}$ values of solubilized purified Bt2 and Bt14 toxins for P.x. are expressed as ng protein spotted per $cm^2$ of artificial diet. $LC_{50}$ values for P.b. are expressed as $ug^2$ toxin per ml solution into which leaf discs, fed to first instar Pb larvae, were dipped. For P.o., $LC_{50}$ values are expressed in ug/ml into which potato chips were dipped prior to feeding.

Labelled Bt2 toxin (1.05 nM) or Bt14 toxin (1.4 nM) was incubated with BBMV from *P. brassicae* (100 ug protein/ml) in a volume of 0.1 ml in combination with varying amounts of unlabelled Bt2 or Bt14. After a 30 min. incubation period at 22° C., the bound and free toxins were separated.

Figure 7:
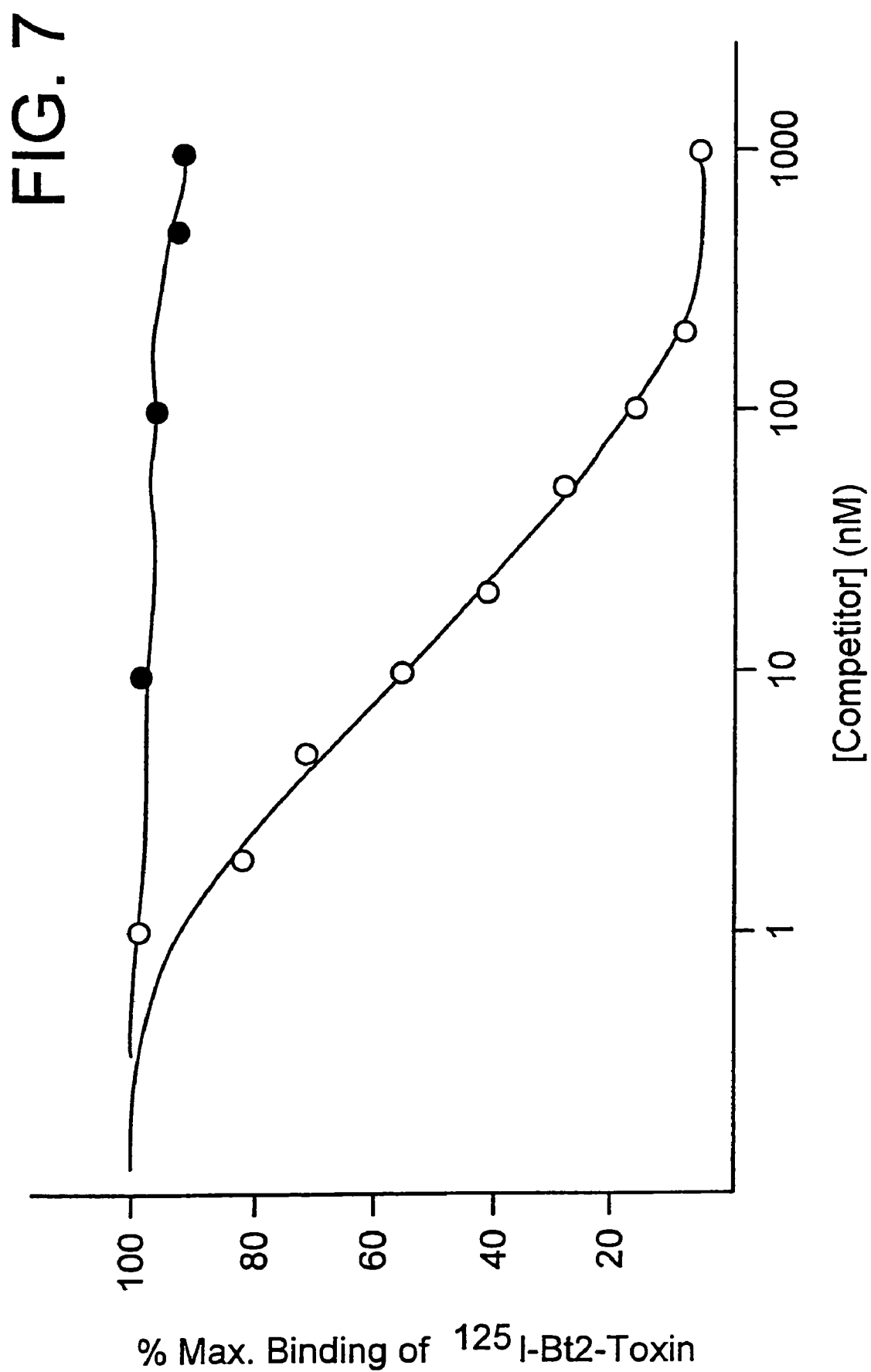
FIG. 7 shows the binding of $^{125}$I-labeled Bt2 toxins to *P. brassicae* brush border membrane vesicles.
Figure 8:
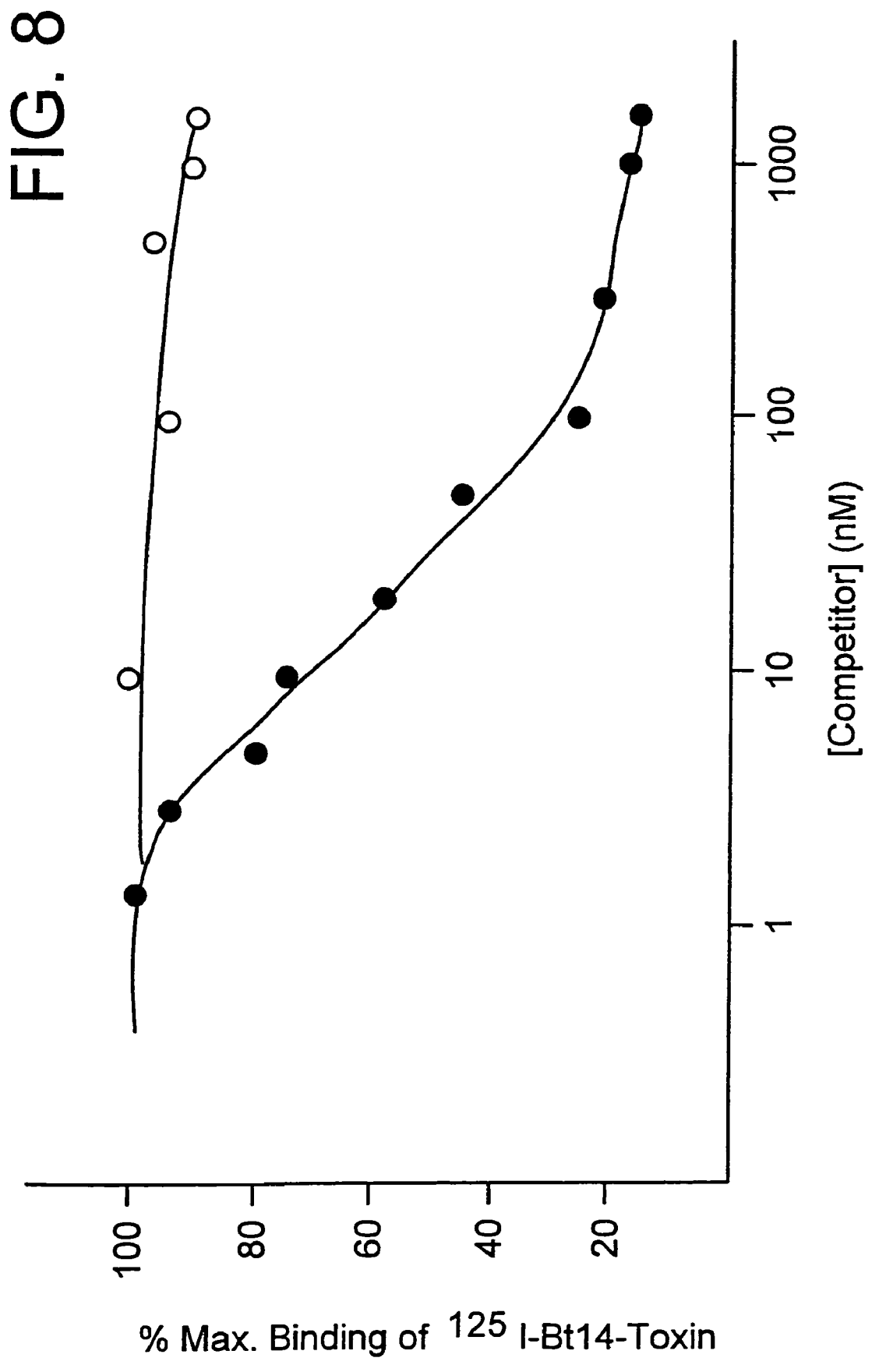

FIGS. 7 and 8 show the binding of $^{125}$I-labeled toxins to *P. brassicae* brush border membrane vesicles. Vesicles were incubated with labeled toxin {in FIG. 7: $^{125}$I-Bt2-toxin (1.05 nM); in FIG. 8: $^{125}$I-Bt14-toxin (1.4 nM)} in the presence of increasing concentrations of Bt2 toxin (○) or Bt14 toxin (●). Binding is expressed as percentage of the amount bound upon incubation with labeled toxin alone. Non-specific binding was not substracted. Data were analyzed with the LIGAND computer program. Each point is the mean of a duplicate sample. FIG. 7 shows the binding of labelled Bt2 toxin to *P. brassicae* BBMV, and FIG. 8 shows the binding of labelled Bt14 toxin to *P. brassicae* BBMV.

The competition data demonstrate the presence of high affinity binding sites both for Bt2 and Bt14, as well as the almost complete absence of competition of Bt14 for the Bt2 binding sites and of Bt14 for the Bt2 binding sites. This demonstrates that Bt2 and Bt14 are non-competitively binding toxins. Hence they are useful to prevent the development of *Pieris brassicae* resistance against *B. thuringiensis* ICP's expressed in *Brassica* sp.

Calculated Kd and Rt values were from these experiments were:
Bt2: Kd=2.8 nM, Rt=12.9 pmol/mg vesicle protein
Bt14: Kd=8.4 nM, Rt=21.4 pmol/mg vesicle protein.

Binding of Bt2 and Bt15 Toxins to BBMV of *M. sexta*. *M. brassicae*, *P. xylostella* and *P. interpunctella*: an Example of Two Non-competitively Binding Lepidopteran ICPs Bt2 and Bt15 toxins are both toxic to *M. sexta* (LC50's of 20 and 111 ng/cm2, respectively). They also show activity against *M brassicae*, *P. xylostella* and *P. interpunctella*.

Labelled Bt2 (1.05 nM) or Bt15 (0.7 nM) was incubated with BBMV from *M. sexta* (100 ug protein/ml) in a volume of 0.1 ml in combination with varying amounts of unlabelled Bt2 or Bt15. After a 30 min. incubation period at 22° C., the bound and free toxins were separated.

Figure 9:
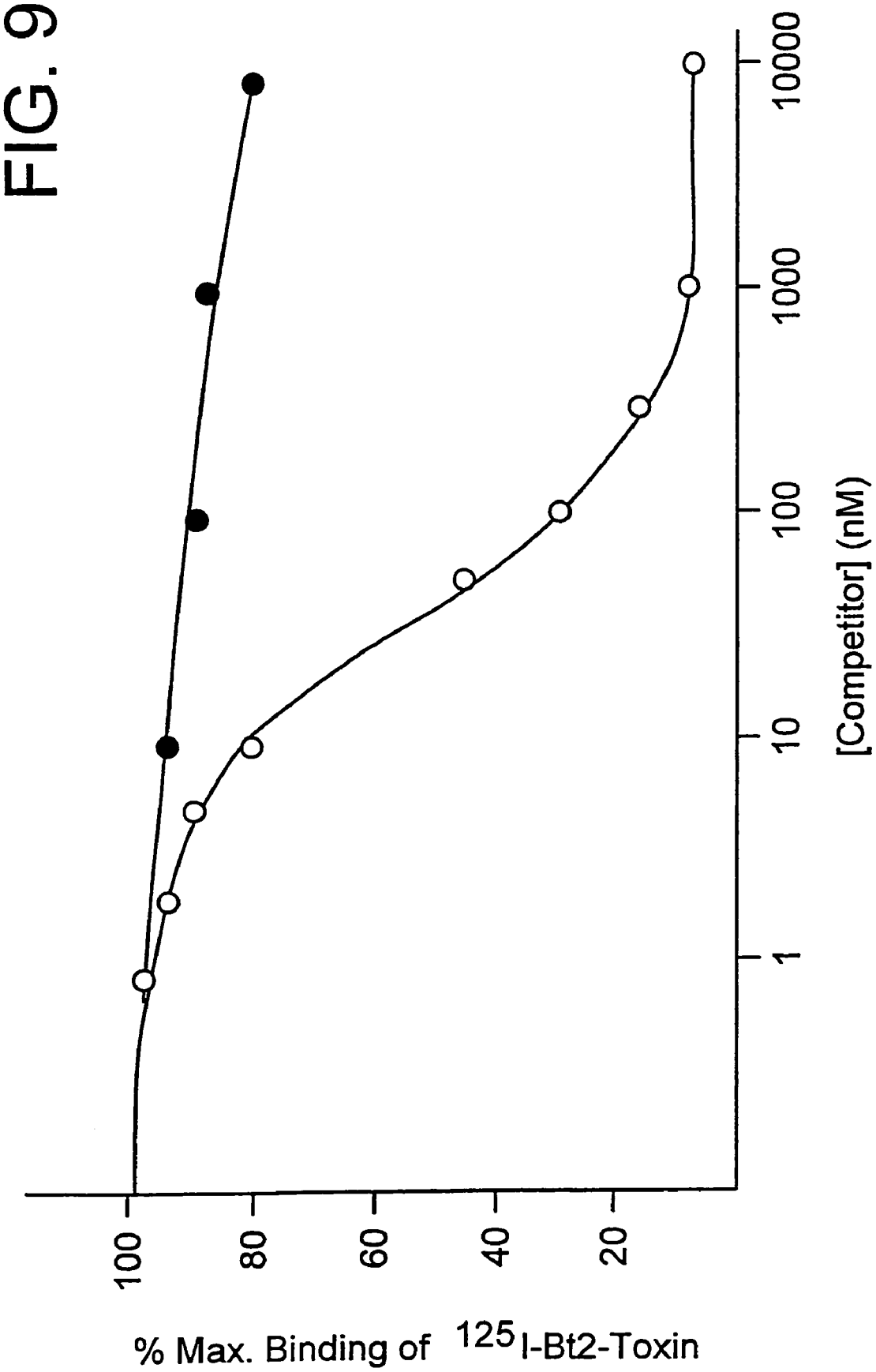
FIG. 9 shows the binding of $^{125}$I-labeled Bt2 toxins to *M. sexta* brush border membrane vesicles.
Figure 10:
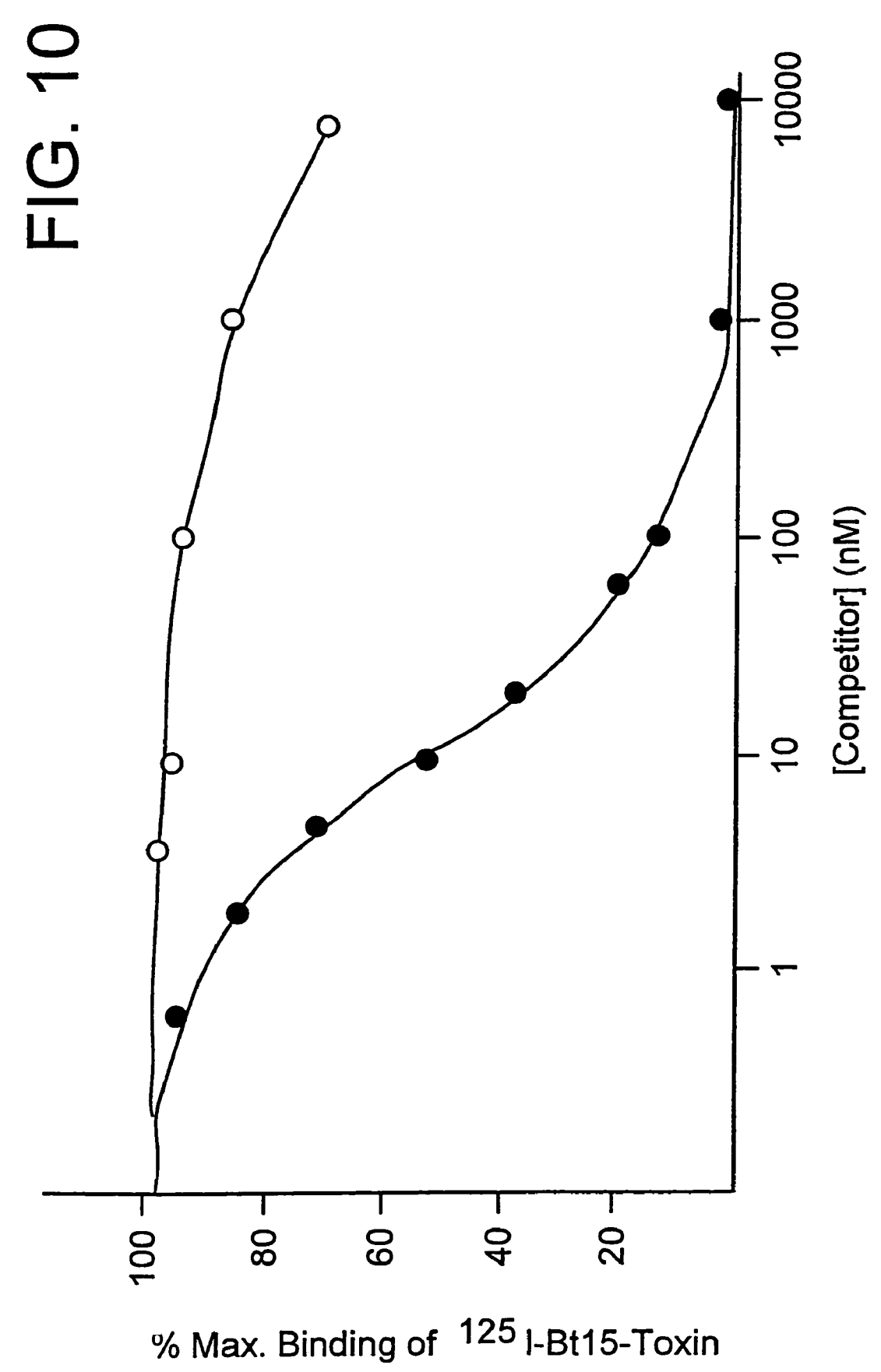

FIGS. 9-10 show the binding of $^{125}$I-labeled toxins to *M. sexta* brush border membrane vesicles. Vesicles were incubated with labeled toxin {in FIG. 9: $^{125}$I-Bt2-toxin (1.05 nM); in FIG. 10: $^{125}$I-Bt15-toxin (0.7 nM)} in the presence of increasing concentrations of Bt2-toxin (○) or Bt15-toxin (●). Binding is expressed as percentage of the amount bound upon incubation with labeled toxin alone. Non-specific binding was not substracted. Data were analyzed with the LIGAND computer program. Each point is the mean of a duplicate sample. FIG. 9 shows the data for binding of labelled Bt2, and FIG. 10 shows the binding of labelled Bt15.

The competition data demonstrate the presence of high affinity binding sites for both Bt2 and Bt15, as well as the complete absence of competition of Bt15 for the Bt2 binding sites and of Bt2 for the Bt15 binding sites. This demonstrates that Bt2 and Bt15 are non-competitively binding toxins. Hence the combination of Bt2 and Bt15 is useful to prevent the development of resistance of *M. sexta* against *B. thuringiensis* ICP's expressed in tobacco or other crops in which *Manduca* sp. are a pest. Calculated Kd and Rt values are: Bt2: Kd=0.4 nM, Rt=3.4 pmol/mg vesicle protein Bt15: Kd=0.3 nM Kd2=2.9 nM, Rt1=5.9 and Rt2=6.7 pmol/mg vesicle protein (2 distinct high affinity receptor sites are present).

Similar studies were performed for *M. brassicae, S. littoralis* and *P. interpunctella*. Although LD50, Kd and Rt values differed substantially, the essential observation that Bt2 and Bt15 are both toxic and are non-competitively binding toxins was confirmed in these three insect species. Thus, it is also a useful toxin combination to prevent resistance of *M. brassicae* to ICP's or to prevent resistance of *Spodoptera* species against ICP's expressed in any of the crop plants in which *Spodoptera* species are a pest.

Binding of Bt2 and Bt4 Toxins to BBMV of *M. sexta*: an Example of Two Non-competitively Binding Lepidopteran ICPs Both Bt2 and Bt4 toxins are toxic to *Manduca sexta*. LD50 values are 20 and 5.4. ng/cm2, respectively. No mutual competition of Bt2 for binding of labelled Bt4 and of Bt4 for binding of labelled Bt2 was observed, demonstrating that Bt2 and Bt4 are non-competitively binding toxins.

Binding of Bt15 and Bt18 Toxins to BBMV of *S. littoralis*: an Example of Two Non-competitively Binding Lepidopteran ICPs Both Bt15 and Bt18 toxins are toxic to *S. littoralis*. LD50 values are 93 and 88 ng toxin/cm$^2$, respectively. Labelled Bt15 (0.7 nM) or Bt18 (0.9 nM) was incubated with 100 ug of vesicle protein from *S. littoralis* in combination with varying amounts of unlabelled Bt15 or Bt18 toxin. After a 45-min. incubation period, bound and free toxins were separated. Binding data demonstrate high affinity binding for both Bt15 and Bt18 to *S. littoralis* BBMV. As seen from FIGS. 11 and 12, the entire population of receptor sites of Bt15 was not saturable with Bt18, nor was the entire population of receptor sites of Bt18 saturable with Bt15.

Binding of Bt13 and Bt22 Toxins to BBMV of *L. decemlineata*: an Example of Two Non-competitively Binding Coleopteran ICPs.

Both Bt13 and Bt22 toxins are toxic to *L. decemlineata*. LD50 values are 0.8 and 1.1 ug toxin/ml respectively. Labelled Bt13 (1 nM) or Bt22 (0.7 nM) was incubated with 100 ug of vesicle protein/ml from *S. littoralis* in combination with varying amounts of unlabelled Bt13 or Bt22 toxin. After a 45 min. incubation period, bound and free toxins were separated. Binding data demonstrate high affinity binding for both Bt13 and Bt22 to *S. littoralis* BBMV. The entire population of receptor sites of Bt13 was not saturable with Bt22. Nor was the entire population of receptor sites of Bt22 saturable with Bt13.

Binding of Bt2 and Bt18 Toxins to BBMV of *M. sexta*: an Example of Two Non-competitively Binding Lepidopteran ICPs.

Both Bt2 and Bt18 toxins are toxic to *M. sexta*, and LD50 values are 20 to 73 ng toxin/cm$^2$ respectively. Labelled Bt2 (1.05 nM) or Bt18 (0.7 nM) was incubated with 100 ug/ml of vesicle protein from *M. sexta* in combination with varying amounts of unlabelled Bt2 or Bt18 toxin. After a 45 min. incubation period, bound and free toxins were separated. Binding data (FIGS. 11-12) demonstrate high affinity binding for both Bt2 and Bt18 to *M. sexta* BBMV. The entire population of receptor sites of Bt2 was not saturable with Bt18. Nor was the entire population of receptor sites of Bt18 saturable with Bt2. Calculated Kd and Rt values are:

Bt2: Kd=0.4 nM, Rt=3.4 pmol/mg vesicle protein.
Bt18: Kd1=0.04 nM, Rt1=2.2 pmoles/mg vesicle protein and Kd2=168 nM Rt2=194 pmoles/mg vesicle protein (2 distinct receptor sites for Bt18 are present).

A list of non-competitively binding anti-Lepidopteran ICP combinations and anti-Coleopteran ICP combinations is given below, together with their common target insect species in which non-competitivity has been demonstrated:

Bt2-Bt15 (*Manduca sexta, Plutella xylostella, Pieris brassicae, Mamestra brassicae, Plodia interpunctella*)
Bt2-Bt18 (*Manduca sexta, Spodoptera littoralis*)
Bt2-Bt14 (*Pieris brassicae, Plutella xylostella, Phthorimaea operculella*)
Bt2-Bt4 (*Manduca sexta*)
Bt15-Bt18 (*Manduca sexta, Spodoptera littoralis*)
Bt14-Bt15 (*Pieris brassicae*)
Bt18-Bt4 (*Manduca sexta, Spodoptera exigua*)
Bt18-Bt4 (*Manduca sexta, Spodoptera littoralis*)
Bt18-Bt14 (*Pieris brassicae*)
Bt18-Bt4 (*Manduca sexta*)
Bt13-Bt21 (*Leptinotarsa decemlineata*)
Bt13-Bt22 (*Leptinotarsa decemlineata*)
Bt21-Bt22 (*Leptinotarsa decemlineata*)

Of course, this list of specific non-competitively binding ICP combinations for specific target insect pests is not exhaustive, and it is believed that other such ICP combinations, including combinations for yet-to-be discovered ICPs, will be found using a similar approach for any target insect species. Likewise, the foregoing list of target insect pests also is not exhaustive, and it is believed that other target insects pests (as well as the plants that are to be transformed to prevent their attack by such pests), against which the specific combinations of ICPs can be used (e.g., the combination of the Bt2 and Bt14 ICPs in *Brassica* to prevent resistance of *Pieris brassicae* against the ICPs expressed in the plant), will be found using a similar approach.

EXAMPLE 7

Selection for Resistance of *Manduca sexta* (Tobacco Hornworm)

A selection experiment involves exposing a large number of larvae to a concentration of a toxin in a diet killing (e.g., 50-90%) of the larvae. The surviving larvae are again exposed to toxin concentrations killing a similar proportion of the larvae, and this process is continued for several generations. The sensitivity of the larvae to the toxin is investigated after each four generations of selection.

Selections for 20 generations of *M. sexta* were performed with Bt2 toxin alone, with Bt18 toxin alone and with a 1/4 (by weight) Bt2/Bt18 mixture. LC50 values of the reference strain for Bt2, B18 and the 1/4 Bt2/Bt18 mixture respectively were the following 20 ng/cm2, 73 ng/cm2 and 62 ng/cm2 of diet.

Selection was initiated at concentrations killing around 75% of the larvae. After 4 generations of selection, survival increased in both the Bt2 and the Bt18 selection to around 70%, no such increase was observed in the selection with the combination of Bt2 and Bt18. Dosages were again increased to calculated LC75 values. This was repeated every 4 generations. The selection process was thus continued to the 20th generation. Final results were the following (LC50 of the 20th generation):

Bt2 selection: LC50 was 6400 ug/g (320 times decreased sensitivity)

Bt18 selection: LC50 was 15100 ug/g (207 times decreased sensitivity)

Bt2/Bt18 selection: LC50 was 181 ug/g (3 times decreased sensitivity).

Thus the decrease in sensitivity was about 100 times slower in the combined selection experiment.

Receptor binding in the three selected *M. sexta* strains was investigated with Bt2 and Bt18 and compared to those of the reference *M. sexta* strain (non-selected strain). Binding characteristics of the reference strain for the Bt2 and BT18 toxins were:

Bt2: Kd=0.4 nM, Rt=3.4 pmol/mg vesicle protein

Bt18: Kd1=0.04 M, Rt1=2.2 pmoles/mg vesicle protein and Kd2=168 nM, Rt2=194 pmoles/mg vesicle protein (2 distinct receptor sites for Bt18 are present).

Figure 11:
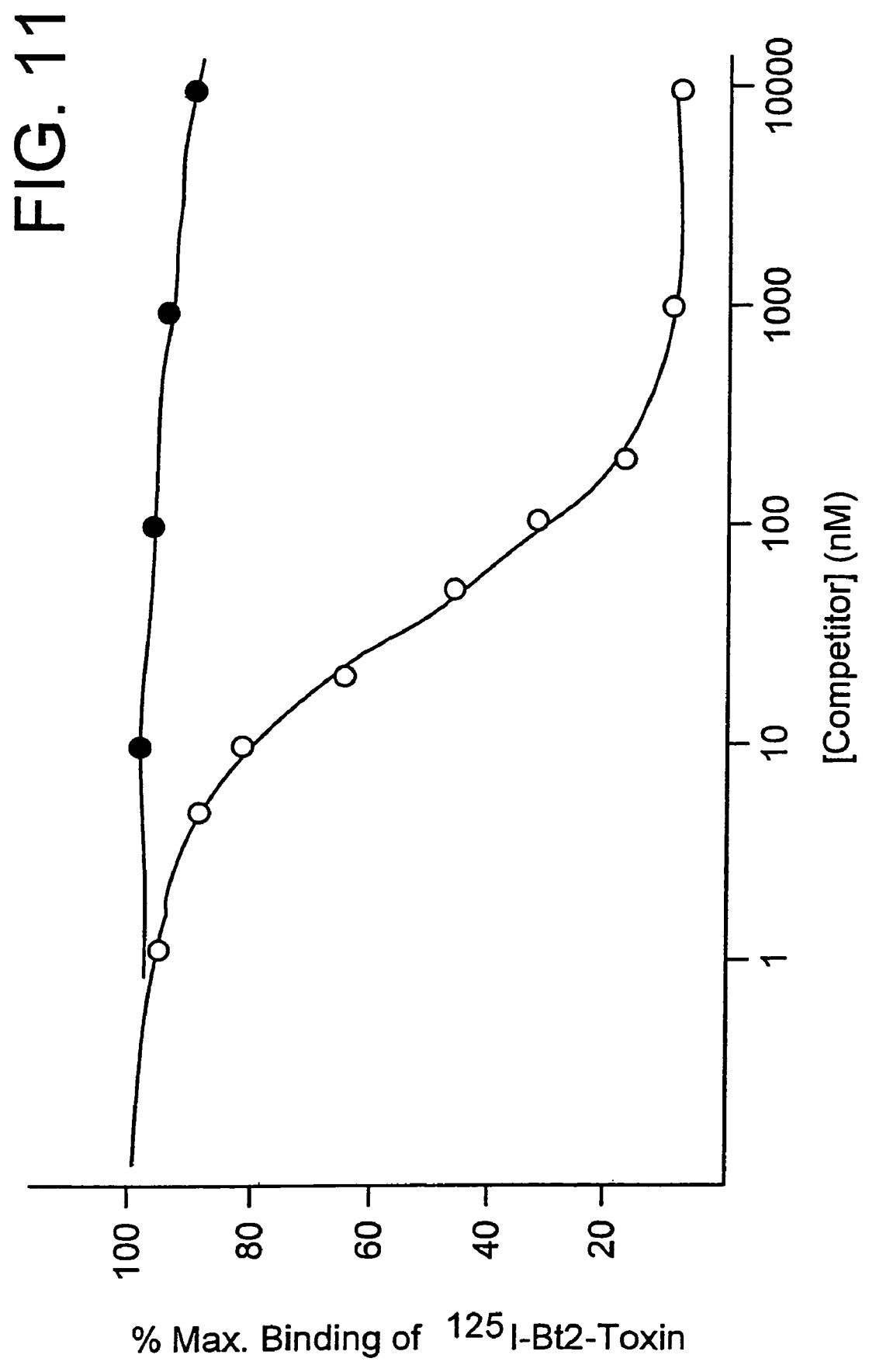
Figure 12:
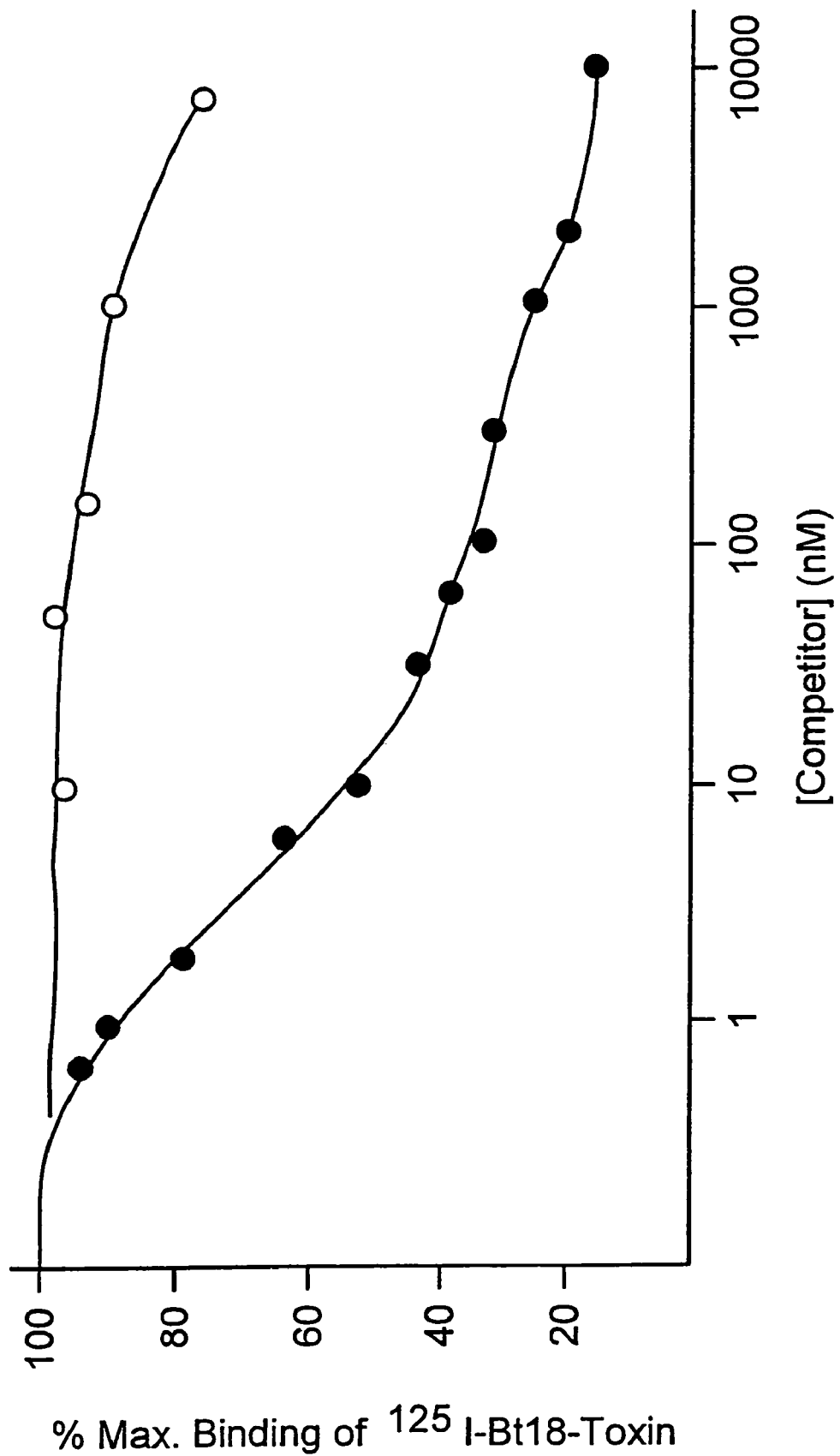
FIG. 12 shows the binding of $^{125}$I-labeled Bt18 toxins to *M. sexta* brush border membrane vesicles.
Figure 15A:
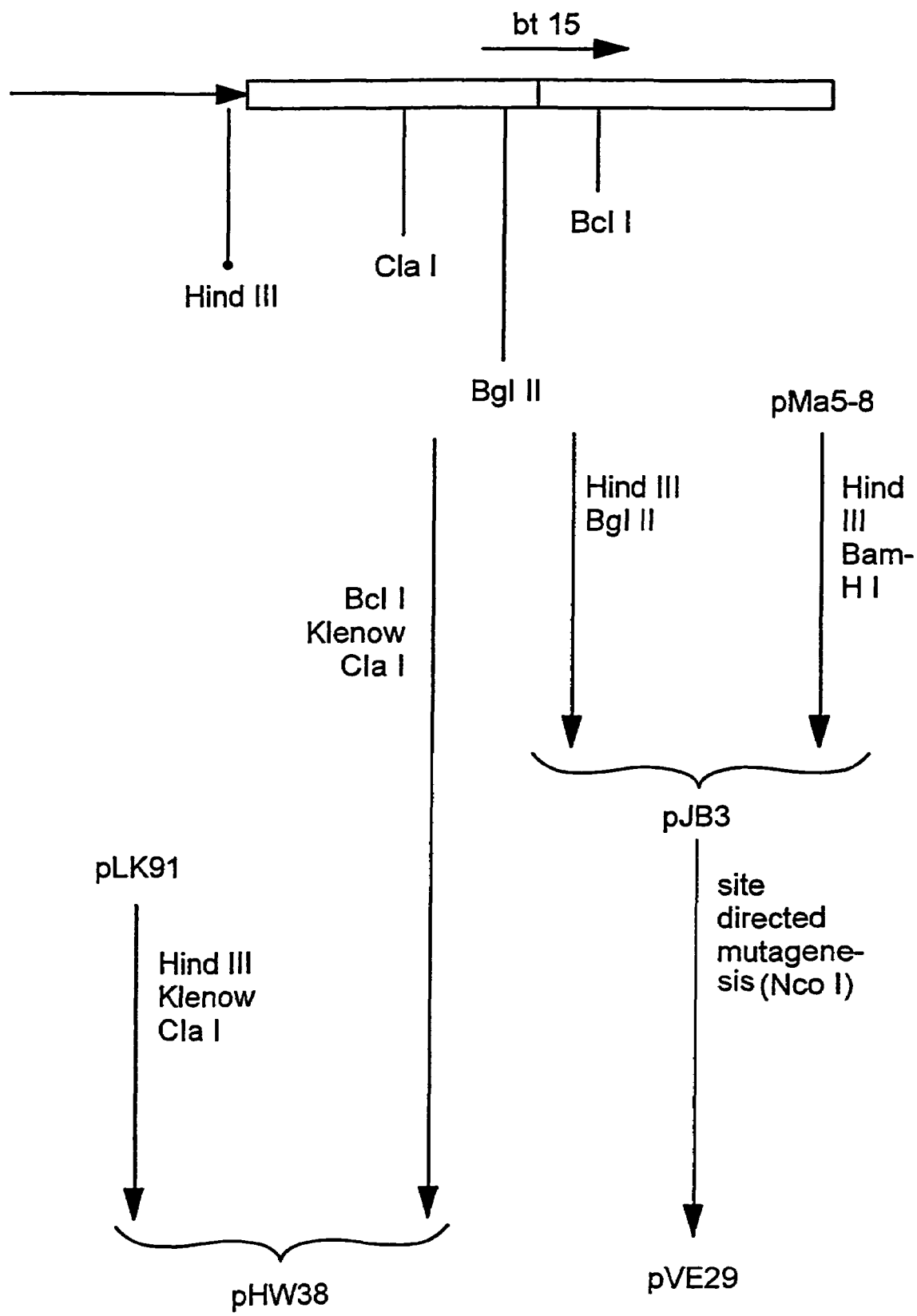
FIGS. 15A-15C schematically show (a) the construction of pVE29; (b) the construction of pVE35; and (c) the construction of pTHW88.
Figure 15B:
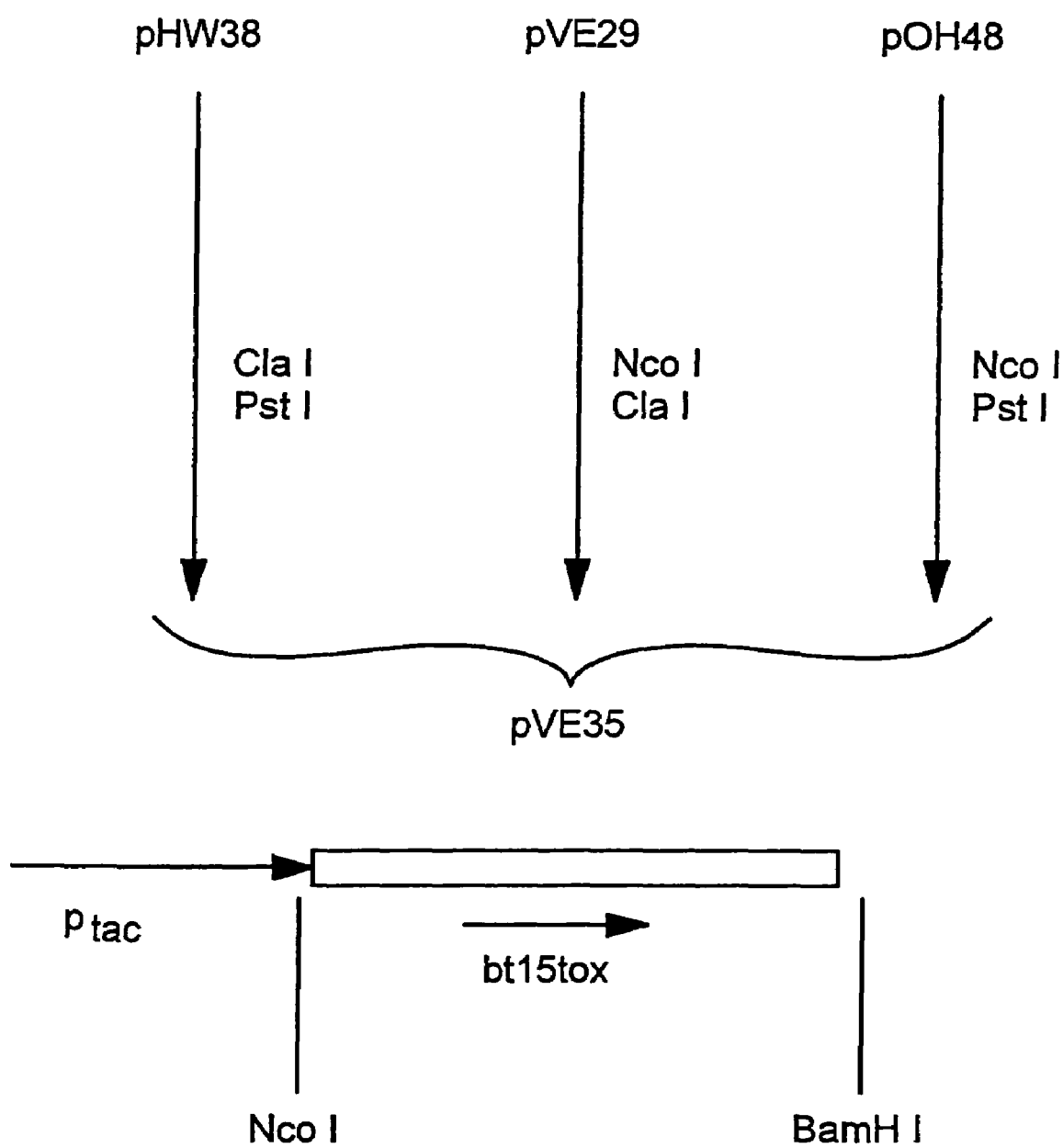
Figure 15C:
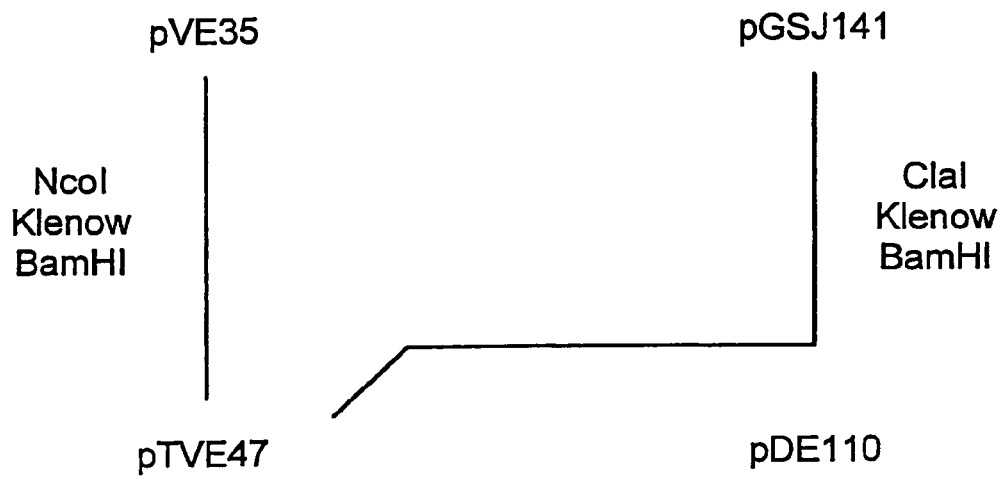
Figure 15C:
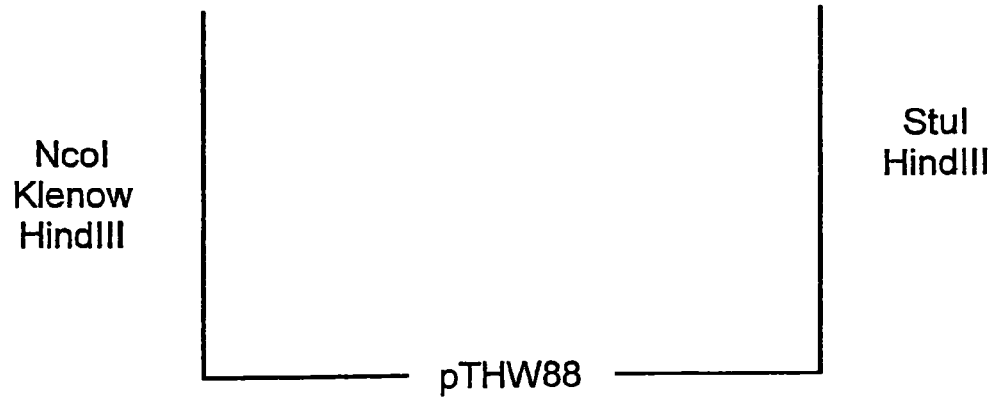
Figure 15C:
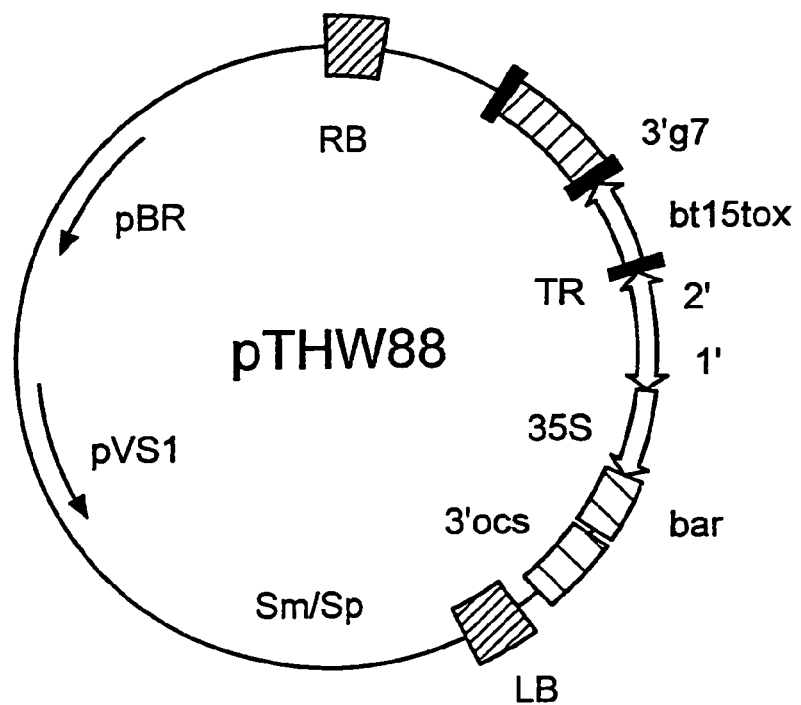
Figure 16A:
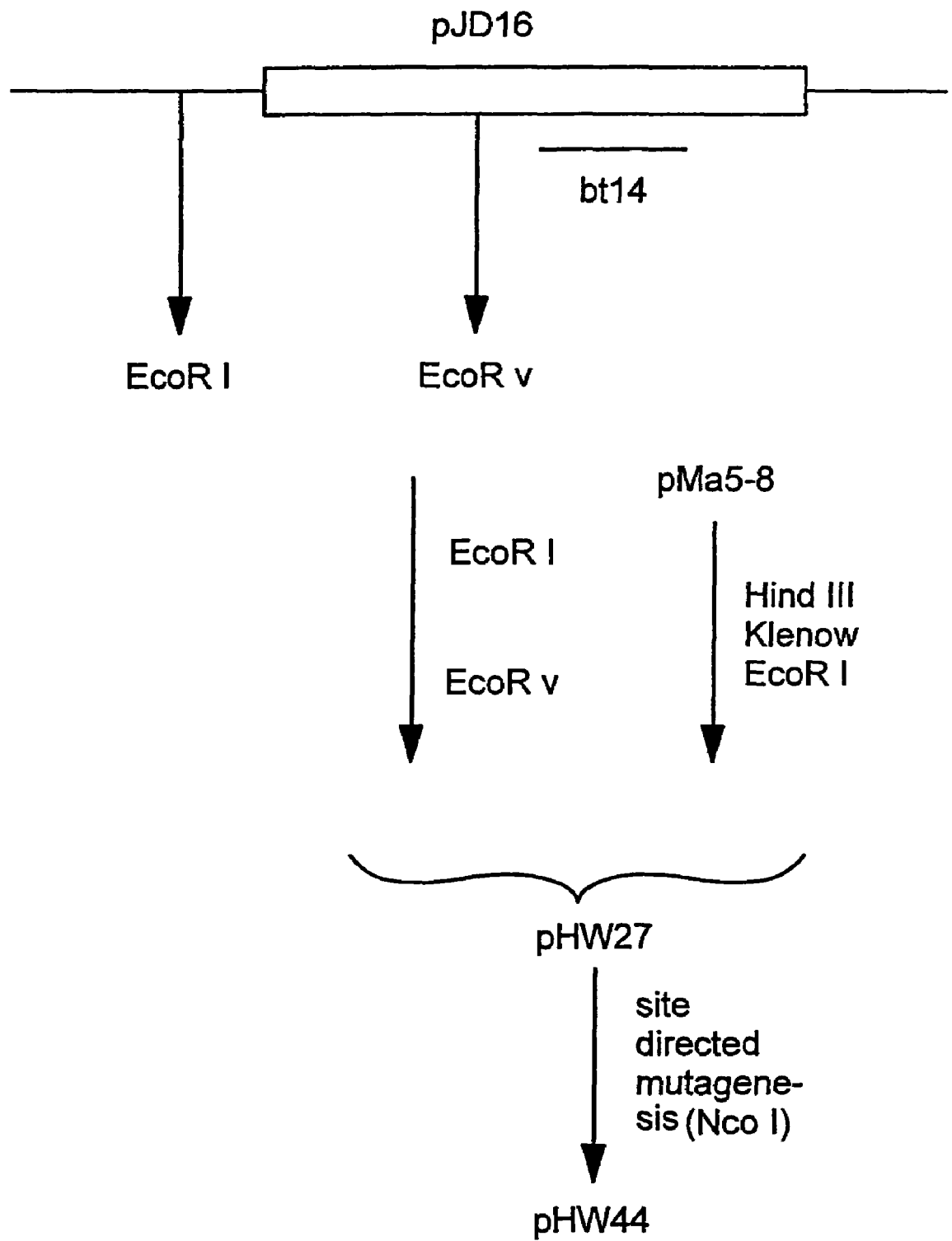
FIGS. 16A-16E schematically show (a) the construction of pHW44; (b) the construction of pHW67; (c) the construction of pHW71; (d) the construction of pTHW94; and (e) restriction map of the pTHW94 vector.
Figure 16B:
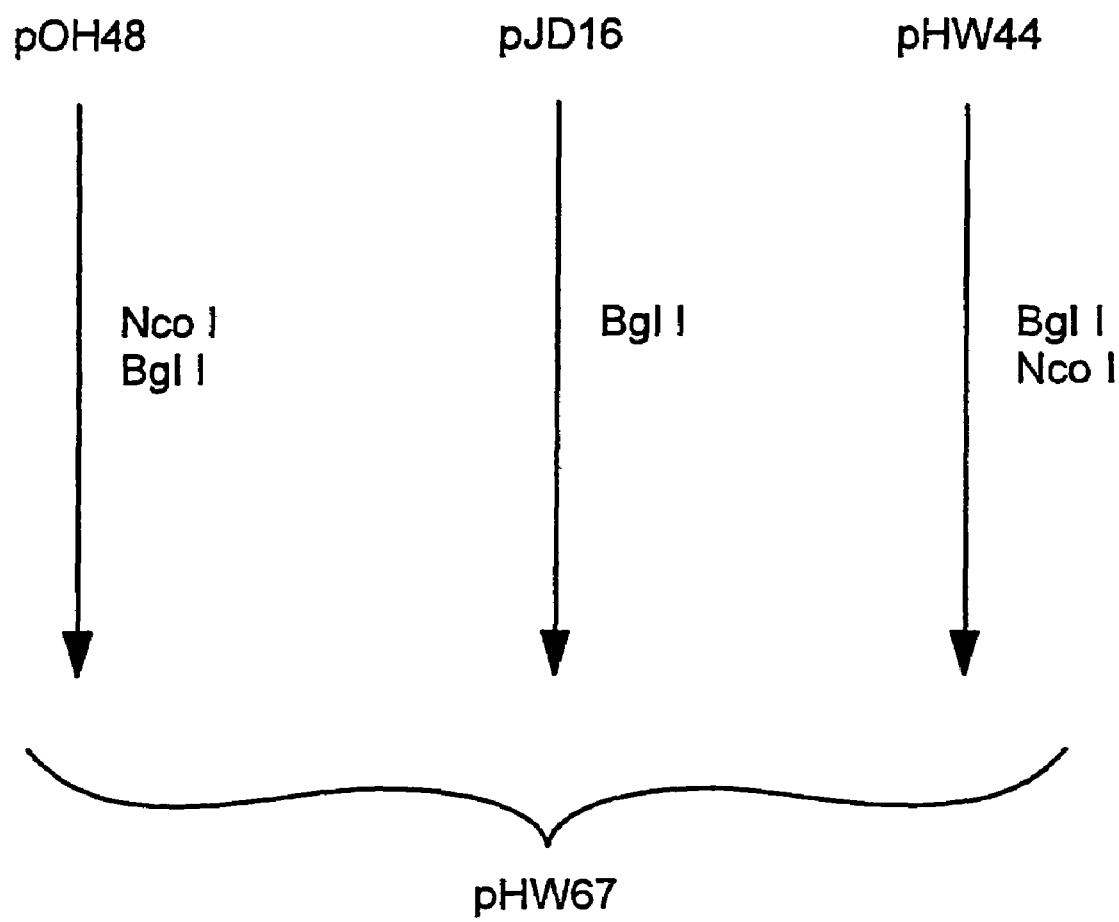
Figure 16B:
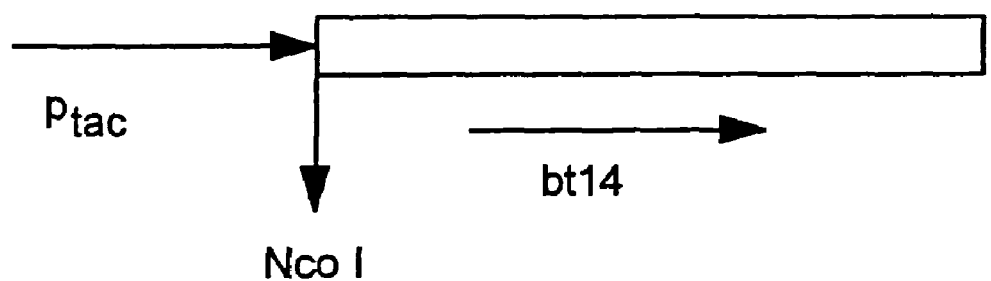
Figure 16C:
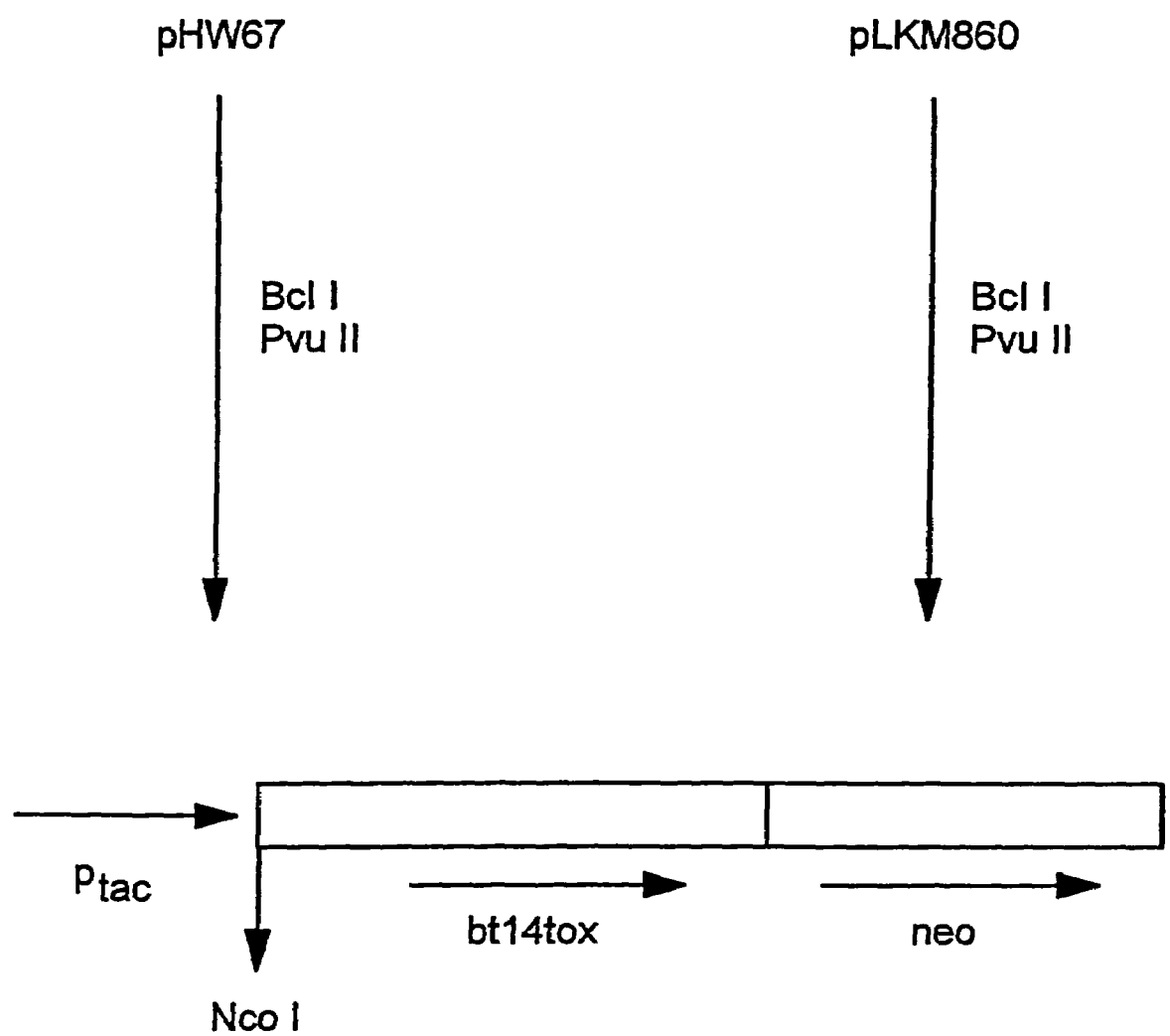
Figure 16D:
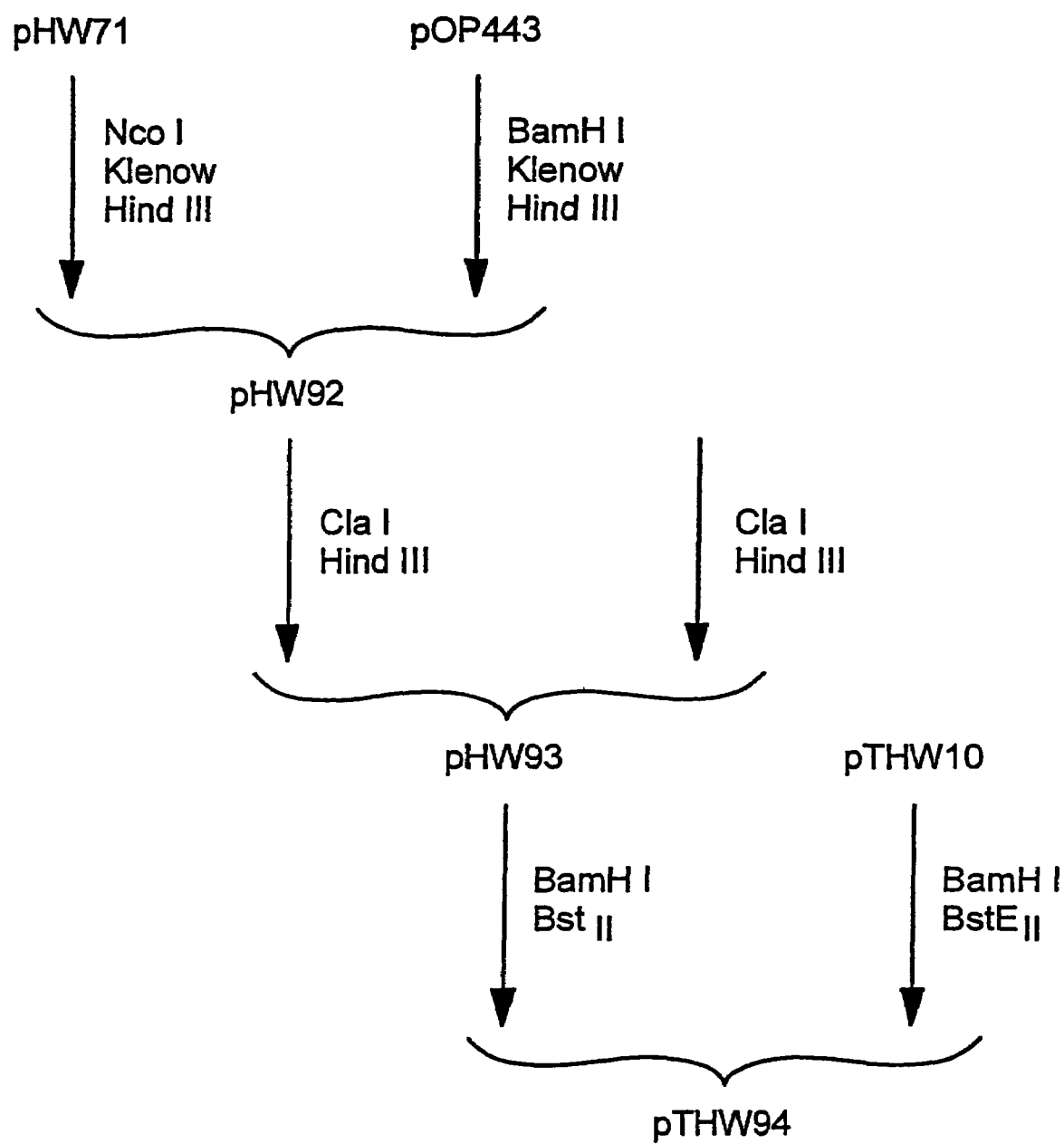
Figure 16E:
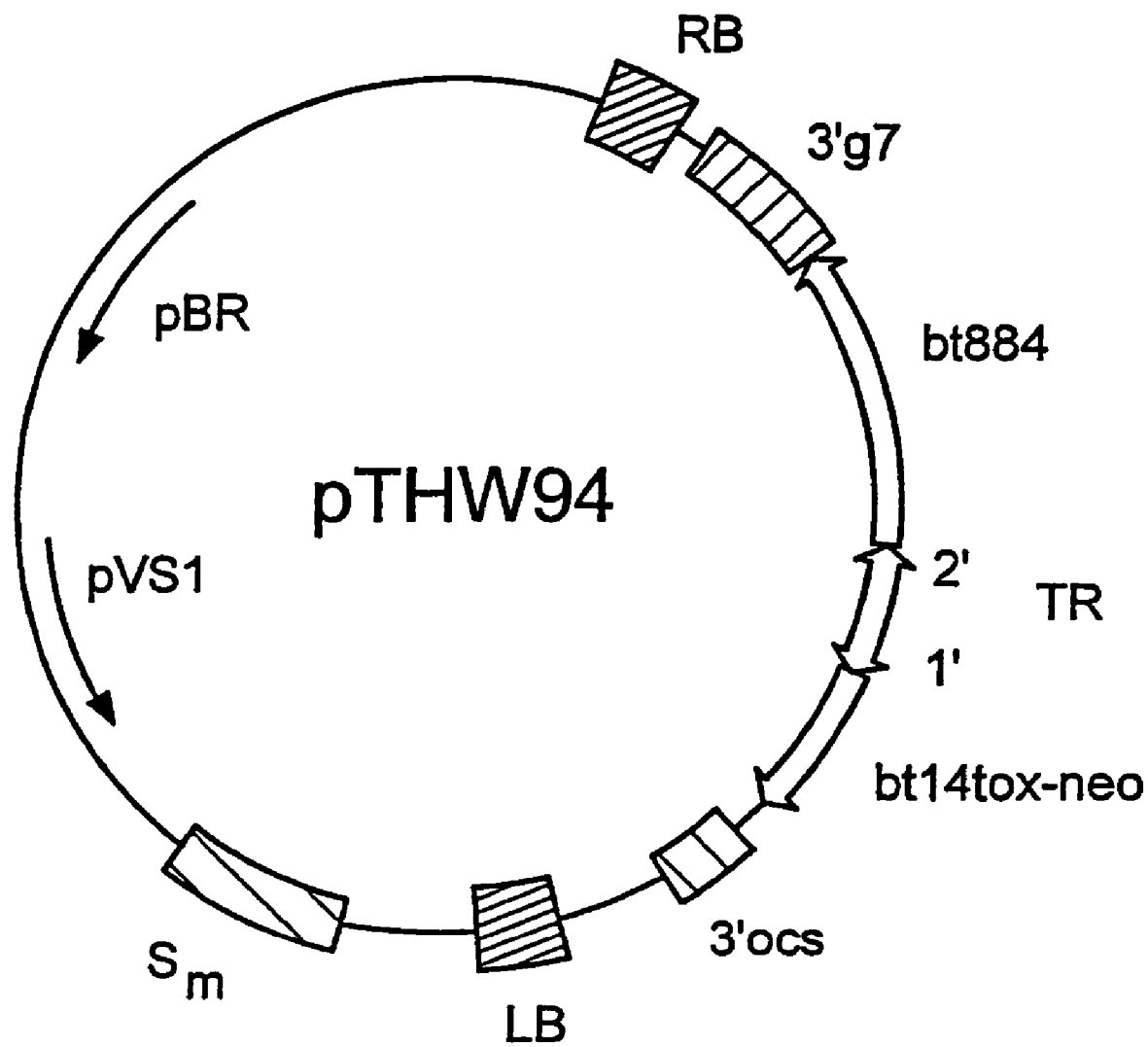

FIGS. 11 and 12 show the binding of $^{125}$I-labeled toxins to *M. sexta* brush border membrane vesicle. Vesicles were incubated with labeled toxin {in FIG. 11: $^{125}$I-Bt2-toxin (1.05 nM); in FIG. 12: $^{125}$I-Bt18-toxin (0.7 nM)} in the presence of increasing concentrations of Bt2-toxin (○) or Bt18-toxin (●). Binding is expressed as percentage of the amount bound upon incubation with labeled toxin alone. Non-specific binding was not substracted. Data were analyzed with the LIGAND computer program. Each point is the mean of a duplicate sample.

The Bt2 selected strain showed no detectable high affinity binding of Bt2 whereas its Bt18 binding characteristics remained close to the reference strain. (Bt18: Kd1=0.03 nM, Rt1=2.8 pmoles/mg vesicle protein and Kd2=199 nM, Rt2=109 pmoles/mg vesicle protein; 2 distinct receptor sites for Bt18 are still present).

The Bt18 selected strain lost the high affinity receptor site for Bt18. The lower affinity site for Bt18 was still present in lower concentration than in the reference strain (Kd=189 nM, Rt=43 nM). Bt2 binding site concentration increased markedly compared to the reference strain (Kd=0.4 nM, Rt=20.8 pmoles/mg vesicle protein). This strain had a Bt2 sensitivity of $LC_{50}$=4 ng/cm$^2$. Thus, its sensitivity for Bt2 had increased as compared to the reference strain ($LC_{50}$=20 ng/cm$^2$).

The Bt2/Bt18 selected strain showed a slight but statistically non-significant decrease in Bt18 binding site concentration. (Bt2: Kd=0.4 nM, Rt=3.4 pmol/mg vesicle protein, Bt18: Kd1=0.04 nM, Rt1=1.0 pmoles/mg vesicle protein and Kd2=168 nM, Rt2=194 pmoles/mg vesicle protein; 2 distinct receptor sites for Bt18 are present). These data demonstrate that, in the two selection lines where resistance occurred, the mechanism was situated at the receptor level. Changes in receptor site are shown to be the most likely mechanism of resistance to *B. thuringiensis* ICPs.

EXAMPLE 8

Mechanism of Resistance of the Diamondback Moth to the Microbial Insecticide *Bacillus thuringiensis*

The mechanism of development of insect resistance to ICPs has been investigated in a *P. xylostella* strain ("PxR"). This insect strain has developed a high level of resistance in the field against Dipel. Crystals of Dipel preparations contain a mixture of ICPs such as Bt3, B2 and Bt73 ICPs; in Example 6, it has been shown that these toxins are competitively binding ICPs.

Resistance to Dipel was confirmed by the toxicity data for the sensitive strain ("PxS") and for the Dipel-resistant strain ("PxR"). High levels of resistance are also observed for the Bt2 protoxin and toxin as shown in the following table

| | $LC_{50}$ of Strains | |
|---|---|---|
| | PxS | PxR |
| Bt2 | 6.7 | >1350 |
| Bt15 | 132.6 | 120.4 |

$LC_{50}$ data are expressed as ng protein spotted per cm$^2$ of artificial diet.

However, insect toxicity data show that there is no resistance to the Bt15 protoxin and Bt15 toxin; this iCP is not present in Dipel crystals. To investigate whether a change in toxin-membrane binding was responsible for resistance, receptor binding studies were performed with $^{125}$I-labeled Bt2 toxin and Bt15 toxin, with BBMV derived from larvae midguts of the PxR and PxS strains. The results are summarized in Table 1, below.

TABLE 1 inding characteristics of Bt2 and Bt15 toxins to brush border membrane vesicles from sensitive and resistant *P. xylostella*.

| ICP | strain | Kd (nM) | Rt (pmol/mg protein) |
|---|---|---|---|
| Bt2 toxin | PxS | 8.1 | 1.6 |
| | PxR | no binding detectable | |
| Bt15 toxin | PxS | 1.9 | 4.2 |
| | PxR | 3.7 | 5.8 |

Table 1 shows that there was high-affinity saturable binding of the Bt2 toxin to midgut membranes of the PxS strain, but the PxR strain showed no detectable level of Bt2 toxin binding. With the Bt15 toxin, there was significant binding to BBMW of both the PxR and PxS strains, and values are not significantly different for the two strains.

These data show that resistance in *P. xylostella* is due to an alteration in toxin-membrane binding. Resistance to the Bt2 toxin and the sensitivity toward the Bt15 toxin of the PxR strain is reflected by the binding characteristics shown in Table 1.

Hence, when different non-competitively binding ICPs (i.e., Bt2 and Bt15) are available with activity against the same insect species (e.g., *P. xylostella*), resistance to one ICP(Bt2) does not imply resistance against other ICPs (such as Bt15). Thus, ICPs with different binding properties can be used in combination to delay development of insect resistance to ICPs.

EXAMPLE 9

Separate Transfer of Two ICP Genes within Individual Transcriptional Units to the Genome of Plant Cells Two procedures are envisaged for obtaining the combined expression of two ICP genes, such as the bt2 and bt15 genes in transgenic plants, such as tomato plants. These procedures are based on the transfer of two chimeric ICP genes, not linked within the same DNA fragment, to the genome of a plant of interest.

A first procedure is based on sequential transformation steps in which a plant, already transformed with a first chimeric ICP gene, is retransformed in order to introduce a second ICP gene. The sequential transformation makes use of two different selectable marker genes, such as the resistance genes for kanamycin ("km") and phosphinotricin acetyl transferase ("PPT"), which confers resistance to phoshinotricin. The use of both these selectable markers has been described in De Block et al. (1987).

The second procedure is based on the cotransformation of two chimeric ICP genes on different plasmids in a single step. The integration of both ICP genes can be selected by making use of the two selectable markers conferring resistance to Km and PPT, linked with the respective ICP genes.

For either procedure, a Ti-plasmid vector is used for *Agrobacterium*-mediated transformation of each chimeric ICP gene into plant cells.

Plasmid pGSH163, described in EP 0193259; contains the following chimeric genes between the T-DNA border repeats: a gene fragment encoding the toxin part of the bt2 gene under the control of the TR2' promoter and the neo gene under control of the TR1' promoter. The 3' ends of the T-DNA gene 7 and octopine synthase respectively provide information for the 3' end formation of transcripts.

A chimeric bt15 gene containing a gene fragment encoding the toxin of the Bt15 ICP under the control of the TR2' promoter, was constructed in the following way (FIG. 15). pOH50 consists of pUC18 with the whole bt15 gene under the control of the lac promoter. A HindIII-BglII fragment was cloned in pMa5-8 yielding pJB3. By site-directed mutagenesis, a NcoI site was created at the initiation codon to yield pVE29. A fragment containing the truncated gene fragment of the bt15 gene, with a translational stop codon, was obtained by isolation of BclI-ClaI from pOH50 and cloning in pLK91, yielding pHW38. The whole toxin gene fragment was reconstructed under the control of the tac promoter, yielding pVE35, by ligation of a ClaI-PstI fragment from pHW38, a NcoI-ClaI fragment from pVE29 and a NcoI-PstI fragment from pOH48. A truncated bt15 gene fragment with a NcoI site at the initiation codon was obtained from pVE35 as a 1980 NcoI-BamHI fragment and cloned in pGSJ141, digested with ClaI and BamHI. pGSJ141 has been described in EPA 88402115.5. Ligation of the filled ClaI site to the filled NcoI site yielded a chimeric TR2'—truncated bt15—3'g7 construct (pTVE47). As a selectable marker in this plasmid, the bar gene encoding phosphinothricin acetyl transferase and conferring resistance to PPT was used. A chimeric bar gene containing the bar gene under the control of the 35S promoter and followed by the 3' end of the octopine synthase was introduced in pTVE47. From pDE11, a 35S-bar-3'ocs fragment was obtained as a StuI-HindIII fragment and was cloned in pTVE47 digested with PstI and HindIII. This yielded the plasmid pTHW88 (FIG. 15) which contains the truncated bt15 gene under the control of the TR2' promoter and the bar gene under the control of the 35S promoter between the T-DNA border repeats. Plasmid pGSH163 is cointegration type Ti-plasmid vector, whereas pTHW88 is a binary type Ti-plasmid vector as described in EPA 0193259.

Both plasmids were mobilized in the *A. tumefaciens* strain C58C1Rif (pGV2260) according to Deblaere et al. (1988). In the sequential transformation procedure, tomato was transformed according to De Block et al. (1987) with the *A. tumefaciens* strain C58C1Rif carrying pGS1163 resulting from the cointegration of pGSH163 and pGV2260. Individual transformants were selected for kanamycin resistance, and regenerated plants were characterized for expression of the truncated bt2 gene according to Vaeck et al. (1987). One representative transformant was subsequently retransformed with the *A. tumefaciens* strain C58C1Rif (pGV2260 and pTHW88), and transformants were selected for PPT resistance. Using this cotransformation procedure, the respective *Agrobacteria* strains, carrying the cointegrate vector pGS1163 and the binary vector pTHW88, were used for transformation of tomato. Individual plants were selected for resistance to Km and PPT.

Schematically shown in FIG. 15 are:

| | |
|---|---|
| a) construction of pVE29: | bt15 N-terminal gene fragment with NcoI site introduced at ATG initiation codon. |
| b) construction of pVE35: | bt15 C-terminal truncated gene fragment under control of the tac promoter. |
| c) construction of pTHW88: | binary T-DNA vector with a chimeric bt15 gene and a chimeric bar gene within the T-DNA border repeats. |

In both cases, co-expression of the two ICP genes in the individual transformants was evaluated by insect toxicity tests as described in EP 0193259 and by biochemical means. Specific RNA probes allowed the quantitive analysis of the transcript levels; monoclonal antibodies cross-reacting with the respective gene products allowed the quantitative analysis of the respective gene products in ELISA tests (EP 0193259); and specific DNA probes allowed the characterization of the genomic integrations of the bt2 and bt15 genes in the transformants. It was found that the transformed tomato plants simultaneously expressed both the bt2 gene (8.1 ng/mg) and the bt15 gene (7.6 ng/mg) as measured by ELISA, which would prevent or delay development of resistance of *M. sexta* to the insecticidal effects of the Bt2 and Bt15 toxins, being expressed.

These procedures also could be applied when one or both ICP genes are part of a hybrid gene. For example, the same strategy as described above could be followed with the plasmid vectors pGSH152, containing a chimeric truncated bt2-neo hybrid gene under control of the TR2' promoter, and pTHW88 in suitable *Agrobacterium* strains.

EXAMPLE 10

Separate Transfer of Two ICP Genes to the Nuclear Genome of Separate Plants in Independent Transformation Events and Subsequent Combination in a Single Plant Through Crossing Tobacco plants have been transformed with either the bt18 gene or the bt15 gene by applying the same cloning strategies as described in EP 0358557 and EP 193259, respectively. For both genes, the plants were transformed with plant expression vectors containing either the truncated bt18 or bt15 gene, which just encode the Bt18 or Bt15 toxin, respectively.

The mortality rate of *Spodoptera littoralis* larvae feeding on the transformed plants is significantly higher than the mortality rate of larvae fed on untransformed plants.

The bt18-transformed plant, which is homozygous for the bt18 gene, is then crossed with the bt15-transformed plant, which is homozygous for the bt15 gene. After selfing, a plant homozygous for both genes is obtained.

The resulting tobacco plants, expressing both the bt18 and bt15 genes, delay significantly development of resistance by *S. littoralis* to either the Bt18 or Bt15 toxin expressed by the plants.

EXAMPLE 11

Transfer of Two Chimeric ICP Genes Linked within the Same DNA to the Genome of Plant Cells The strategy used is based on the organization of two independent chimeric ICP genes between the T-DNA border repeats of a single vector. Binding studies indicated that the Bt2 and Bt14 toxins are two non-competitively binding ICPs with insecticidal activity towards *Pieris brassicae*. For expression in plants, both the bt2 and bt14 genes can be co-expressed to prevent insect resistance development. For the design of a plasmid vector with each ICP gene under the control of a separate promoter, two possibilities can be envisaged: 1) three chimeric constructs carrying the truncated bt2 and bt14 genes and a selectable marker, respectively; or 2) a hybrid of a truncated gene fragment (bt2 or bt14) and the neo gene can be used in combination with a truncated bt14 or bt2 gene.

This Example describes the construction of the vector pTHW94 for plant transformations carrying the following chimeric ICP genes between the T-DNA border repeats: a truncated bt2 gene fragment under the control of the TR2' promoter and a hybrid truncated bt14-neo gene under the control of the TR1' promoter. The 3' end of the T-DNA gene 7 and octopine synthase, respectively, provide information for proper 3' end formation. pTHW94 has been deposited at the DSM under accession no. 5514 on Aug. 28, 1989.

Schematically shown in FIG. 16 are the:

| | |
|---|---|
| a) construction of pHW44: | bt14 N-terminal gene fragment with NcoI site introduced at ATG initiation codon. |
| b) construction of pHW67: | reconstruction of the bt14 gene under the control of the tac promoter. |
| c) construction of pHW71: | construction of a hybrid truncated bt14-neo gene under the control of the tac promoter. |
| d) construction of pTHW94: | binary T-DNA vector with a chimeric bt14 gene and a chimeric bt2 gene within the T-DNA border repeats. |

The pTHW94 vector is mobilized into the *Agrobacterium* strain C58C1Rif (pMP90) which is used to transform *Brassica napus* according to the procedure described by De Block et al. (1989). Transformants are selected on Km, and regenerated plants are found to express both ICP gene products in insect toxicity tests and biochemical tests.

EXAMPLE 12

Expression of Two ICP Genes in a Hybrid Construct

In order to obtain a combined and simultaneous expression of two ICP genes, truncated gene fragments encoding the toxic parts of two different ICPs can be fused in a proper reading frame and placed, as a hybrid gene, under the control of the same promoter in a chimaeric gene construct. Toxic cores from certain ICPs can be liberated from their protoxins by protease activation at the N- and/or C-terminal end. Thus, hybrid genes can be designed with one or more regions encoding protease cleavage site(s) at the fusion point(s) of two or more ICP genes.

Figure 17:
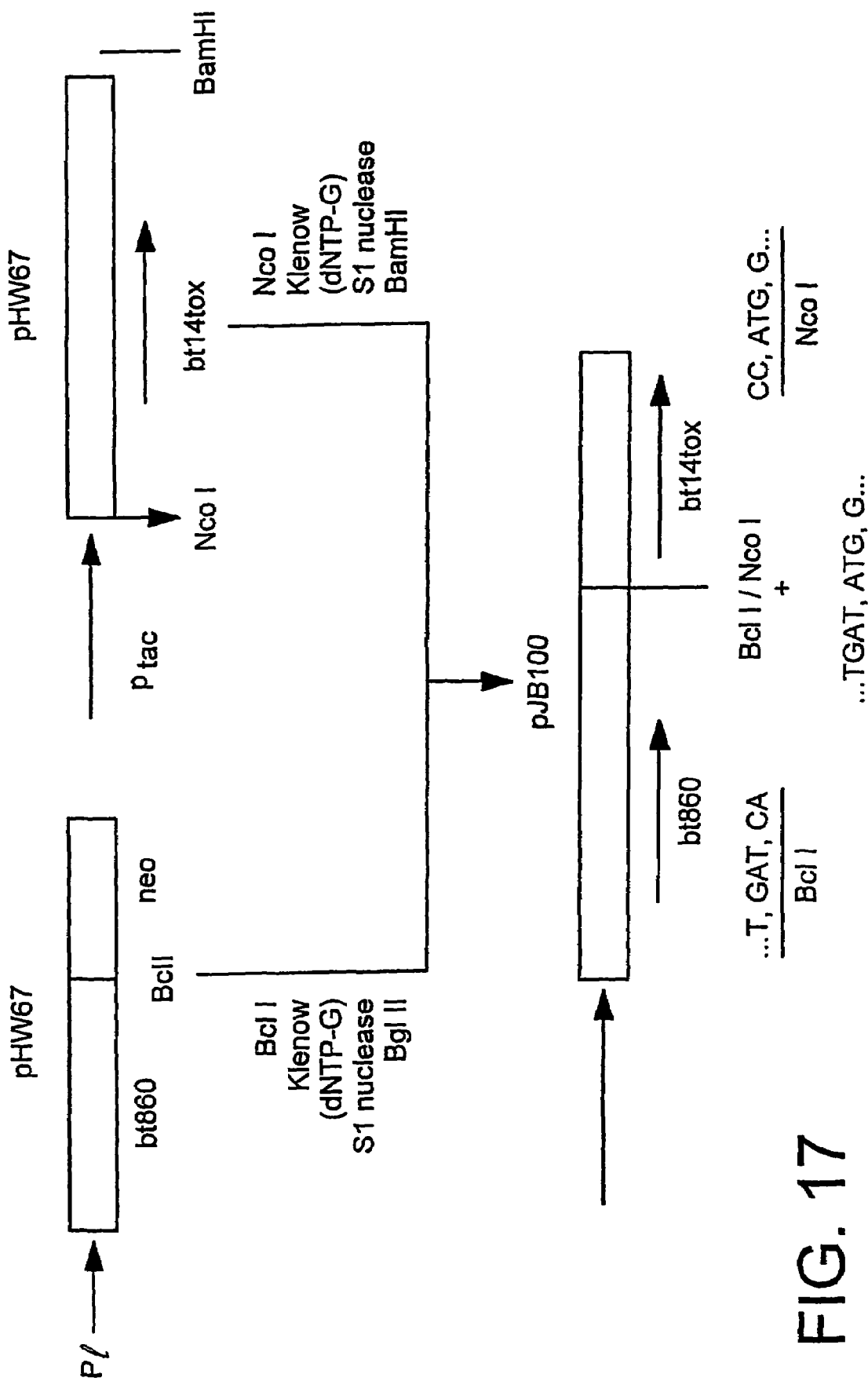
FIG. 17 schematically shows the construction of a hybrid bt2-bt gene with a C-terminal bt2 gene fragment (bt860) encoding the toxic core of the Bt2 protoxin in frame with a C-terminal truncated bt14 gene fragment encoding the toxic core of the Bt14 protoxin.

The simultaneous co-expression of the bt2 and bt14 genes is obtained by constructing a hybrid gene composed of a truncated bt14 gene fragment fused to a truncated bt2 gene fragment. Schematically shown in FIG. 17 is the construction of such a hybrid bt2-bt14 gene with a C-terminal bt2 gene fragment (bt860) encoding the toxic core of the Bt2 protoxin in frame with a C-terminal truncated bt14 gene fragment encoding the toxic core of the Bt14 protoxin. The BclI site in the bt2 gene, localized downstream of the trypsin cleavage site, is fused in frame with the NcoI site introduced at the N-terminal end of the truncated bt14 gene fragment. To this end, the plasmids pLBKm860 (EP 0193259) and pHW67 are used. pLBKm860 contains a hybrid bt2-neo gene under control of the lambda $P_L$ promoter. The bt2 gene moiety in the hybrid gene is a C-terminal truncated bt2 gene fragment, indicated as bt860 (in FIG. 17) (see also Vaeck et al, 1987). The construction of pHW67 is described in FIG. 16. pHW67 contains a C-terminal truncated bt14 gene fragment (bt14tox) with a NcoI site at the ATG initiation codon, a translation stop codon located at the BclI site of the intact bt14 gene and a BamHI site downstream of the whole gene fragment. To fuse both gene fragments in the proper reading frame, the BclI and NcoI ends of the respective plasmids are treated with Klenow DNA polymerase and S1 nuclease as indicated in FIG. 16. The resulting plasmid pJB100 contains the hybrid bt860-bt14tox gene under control of the lambda $P_L$ promoter and directs the expression in *E. coli* of a fusion protein with the expected mobility on SDS-PAGE.

Crude extracts of the *E. coli* strain show the toxicity of the fusion protein, expressed by the strain, against *P. brassicae*. It has also been confirmed by N-terminal amino acid sequence analyses of the fusion protein produced by the *E. coli* strain that the N-terminal amino acids from the Bt14 protoxin are processed upon activation. The bt2-bt14 hybrid gene product has thus two potential protease cleavage sites.

Subsequently, this hybrid gene is inserted into a vector for plant transformations and placed under control of a suitable promoter and transferred to the genome of *Brassica* (EP 0193259) where both the bt2 and bt14 genes are expressed in insect toxicity tests.

TABLE 2

| Gene | St strain | Host range | amino acids encoded | predicted MW (kDa) of encoded amino acids | Disclosure of nucleotide sequence |
|---|---|---|---|---|---|
| bt3 | HD-1 kurstaki | L | 1176 | 133.2 | Schnepf et. al., 1985 |
| bt2 | berliner 1715 | L | 1155 | 131 | Hofte et. al., 1986 |
| bt73 | HD-73 | L | 1178 | 133.3 | Adang et. al., 1985 |
| bt14 | entomocidus HD-110 | L | 1207 | 138 | Brizzard and Whiteley, 1988 |
| bt15 | entomocidus HD-110 | L | 1189 | 134.8 | FIG. 14 |
| bt4 | HD-68 aizawai | L | 1165 | 132.5 | FIG. 15 |
| bt18 | darmstadiensis HD-146 | L | 1171 | 133 | EP appln. 88402241.0 |
| bt13 | BtS1, DSM4288 22/10/87 | C | 644 | 73.1 | EP appln. 88402115.5 |
| bt21 | BtPGSI208, DSM 5131, 19/1/89 | C | 651 | 74.2 | EP appln. 89400428.2 |

TABLE 2-continued

| Gene | St strain | Host range | amino acids encoded | predicted MW (kDa) of encoded amino acids | Disclosure of nucleotide sequence |
|---|---|---|---|---|---|
| bt22 | BtPGSI245, DSM 5132, 19/1/89 | C | 1138 | 129 | EP appln. 8940028.2 |
| P2 | HD-263 | L/D | 633 | 70.9 | Donovan et. al., 1988 |
| Cry B2 | HD-1 | L | 633 | 70.8 | Widner and Whiteley, 1989 |

REFERENCES

Adang M., Staver M., Rocheleau T., Leighton J., Barker R. and Thompson D. (1985), Gene 36, 289-300.
Angenon et al (1989), Molecular and Cellular Biology 9, 5676-5684.
Barton K., Whiteley H. and Yang N. -S. (1987), Plant Physiol. 85, 1103-1109.
Bernard H., Remaut E., Hersfield M., Das H., Helinski D., Yanofski C. and Franklin N. (1979), Gene 5, 59-76.
Bell R. and Joachim F. (1976), Ann. Entomol. Soc. Am. 69, 365-373.
Botterman J. and Zabeau M. (1987), DNA 6, 583-591.
Bradford M. (1976), Anal. Biochem. 72, 248-254.
Brattsten L., Holyoke C., Leeper J. and Raffa K. (1986), Science 231, 1255-1260.
Brizzard B. and Whiteley H. (1988), Nucleic Acids Research 16, 4168-4169.
Deblaere R., Reynaerts A., Hofte H., Hernalsteens J-P, Leemans J. and Van Montagu M. (1988), Methods in Enzymol. 153, 277-292.
De Block M., Botterman J., Vandewiele M., Dockx J., Thoen, Gossele V., Rao Movva, Thompson C., Van Montagu M. and Leemans J. (1987), EMBO J. 6, 2513-2518.
De Block et al (1989), Plant Physiology 91, 694-701.
De Boer H., Comstock L. and Vasser M. (1983), Proc. Natl. Acad. Sci. USA 80, 21-25.
de Framond A., Back E., Chilton W., Kayes L. and Chilton M-D (1986), Mol. Gen. Genet. 202, 125-131.
De Greve et al (1982), J. Mol. Appl. Genet. 1 (6), 499-511.
De La Pena and Schell (1986), Nature 325, 274-276.
Delauney A., Tabaeizadeh Z. and Verma D. (1988), Proc. Natl. Acad. Sci. USA 85, 4300-4304.
Depicker A., Herman L., Jacobs A., Schell J. and Van Montagu M. (1985), Mol. Gen. Genet. 201, 477-484.
Donovan W., Dankoscik C. and Gilbert W. (1988), J. Bacteriol. 170, 4732-4738.
Dulmage H. T and cooperators (1981), In: Microbial control of pests and plant diseases 1970-1980 (Ed. H. D. Burges), Academic Press, 193-222.
Finney D. (1962), Probit Analysis (University Press, Cambridge), pp. 50-80.
Fischhoff D., Bowdish K., Perlak F., Marrone P., McCormick S., Niedermeyer J., Dean D., Kuzano-Kretzmer K., Mayer E., Rochester D., Rogers S. and Fraley R. (1987), Bio/Technology 5, 807-812.
Franck, Guilley, Jonard, Richards and Hirth (1980), Cell 21, 285-294.
French B., Maul H. and Maul G. (1986), Anal. Biochem. 156, 417-423.
Fuller F. (1982), Gene 19, 43-54.
Gardner, Howarth, Hahn, Brown-Luedi, Shepard and Messing, Nucl. Acids Res. 9, 2871-2887.
Goldberg L. and Margalit J. (1977), Mosq. News 37, 355-358.
Goldman I., Arnold J. and Carlton B. (1986), J. Invert. Pathol. 47, 317-324.
Gould F. (1988), Bioscience 38, 26-33.
Haider M., Knowles B. and Ellar D. (1986), Eur. J. Biochem. 156, 531-540.
Herrera-Estrella (1983) Nature 303, 209-213.
Hofmann C., Luthy P., Hutter R. and Pliska V. (1988a), Eur. J. Biochem. 173, 85-91.
Hofmann C., Vanderbruggen H., Hofte H., Van Rie J., Jansens S. and Van Mellaert H. (1988b), Proc. Natl. Acad. Sci. USA 85, 7844-7848.
Hofte H., Van Rie J., Jansens S., Van Houtven A., Verbruggen H. and Vaeck M. (1988), Appl. Environ. Microbiol. 54, 2010-2017.
Hofte H., De Greve H., Seurinck J., Jansens S., Mahillon J., Ampe C., Vanderkerkhove J., Vanderbruggen H., Van Montagu M., Zabeau M. and Vaeck M. (1987), Eur. J. Biochem. 161, 273-280.
Hofte H. and Whiteley H. R. (1989), Microbiological Reviews 53, 242-255.
Hsiung H. and Becker G. (1988), Biotech. and Genetic Engin. Rev. 6, 43-65.
Hull and Howell (1987), Virology 86, 482-493.
Hunter W. and Greenwood F. (1962), Nature 194, 495-496.
Kozak M. (1987), Mol. Cell. Biol. 7, 3438-3445.
Krebbers E., Herdies L., De Clercq A., Seurinck J., Leemans J., Van Damme J., Segura M., Gheysen G., Van Montagu M. and Vandekerckhove J. (1988), Plant Physiol. 87, 859-866.
Knowles B. and Ellar D. (1986), J. Cell. Sci 83, 89-101.
Krieg A., Huger A., Langenbruch G. and Schnetter W. (1983), Z. Ang. Ent. 96, 500-508.
Krieg A. and Langenbruch G. (1981), In: Microbial control of pests and plant diseases 1970-1980 (Ed. H. D. Burges), Academic Press, 837-986.
Kirsch K. and Schmutterer H. (1988), J. Appl. Ent. 105, 249-255.
Kronstad J., Schnepf H. and Whiteley H. (1983), J. Bacteriol. 154, 419-428.
Mahillon J. and Delcour J. (1984), J. Microbial. Methods 3, 69-73.
Maxam A. and Gilbert W. (1980), Methods in Enzymol. 65, 499-560.
McGaughey W. (1985), Science 229, 193-195.
McGaughey W. and Beeman R. (1988), J. Econ. Entomol. 81, 28-33.
Munson P. and Rodbard D. (1980), Anal. Biochem. 107, 220-239.
Pazkowski and cooperators (1984), EMBO J. 3, 2717-2722.
Peleman J., Boerjan W., Engler G., Seurinck J., Botterman J., Alliote T., Van Montagu M. and Inze D. (1989), The Plant Cell 1, 81-93.
Remaut E., Stanssen P. and Fiers W. (1981), Gene 15, 81-93.
Rocha-Sosa et al (1989) EMBO J. 8, 23-29.
Sandler S., Stayton M., Townsend J., Ralstan M., Bedbrook J. and Dunsmuir P. (1988), Plant Mol. Biol. 11, 301-310.
Scatchard G. (1949), Ann. N.Y. Acad. Sci. 51, 660-672.
Schocher R., Shillito R., Saul M., Pazkowski J. and Potrykus I. (1986) Bio/technology 4, 1093-1096.
Shields (1987), Nature 328, 12-13.
Schnepf H., Wong H. and Whiteley H. (1985), J. Biol. Chem. 260, 6264-6272.

Stanssens P., Remaut E. and Fiers W. (1985), Gene 36, 211-223.

Stanssens P., McKeown Y., Friedrich K. and Fritz H. (1987): "Oligo-nucleotide directed construction of mutations by the gapped duplex DNA method using the pMa/c plasmid vectors", published in the Collection of Experimental Procedures distributed at the EMBO course entitled "Directed mutagenesis and protein engineering" in July 1987 at the Max Planck Institut fur Biochemie, Martinsried, FRG.

Stone T., Sims S. and Marrone P. (1989), J. Invert. Pathol. 53, 228-234.

Vaeck M., Reynaerts A., Hofte H., Jansens S., De Beukeleer M., Dean C. Zabeau M., Van Montagu M. and Leemans J. (1987), Nature 327, 33-37.

Voller, Bidwell and Barlett (1976), In: Manual of Clinical Immunology (Eds. Rose and Friedman), pp. 506-512, American Society of Microbiology, Washington Velten J., Velten L., Hain R. and Schell J. (1984), EMBO J. 3, 2723-2730.

Velten J. and Schell J. (1985), Nucl. Acids Res. 13, 6981-6998.

Widner W. and Whiteley H. (1989), J. Bacterriol. 171, 965-974.

Wolfersberger M., Luthy P., Maurer A., Parenti P., Sacchi V., Giordana B. and Hanozet G. (1987), Comp. Biochem. Physiol. 86, 301-308.

Yanish-Perron C., Veiera J. and Messing J. (1985), Gene 33, 103-119.

The invention claimed is:

1. An isolated DNA encoding a protein comprising the amino acid sequence of SEQ ID NO: 8, or an insecticidally effective fragment thereof.

2. The DNA of claim 1 comprising the sequence of SEQ ID NO: 7 from nucleotide 234 to nucleotide 3803.

3. A chimeric gene comprising a) a promoter that can direct expression in plant cells operably connected to b) the DNA of claim 1.

4. A plant, seed, or plant cell comprising the chimeric gene of claim 3.

5. A method to control *Manduca sexta, Pieris brassicae, Mamestra brassicae, Plutella xylostella, Spodoptera exigua, Plodia interpunctella*, or *Spodoptera littoralis*, said method comprising the step of providing a transgenic plant comprising the chimeric gene of claim 3, wherein said plants control *Manduca sexta, Pieris brassicae, Mamestra brassicae, Plutella xylostella, Spodoptera exigua, Plodia interpunctella*, or *Spodoptera littoralis*.

* * * * *

SEQUENCE LISTING

```
<160> NUMBER OF SEQ ID NOS: 10

<210> SEQ ID NO 1
<211> LENGTH: 12
<212> TYPE: DNA
<213> ORGANISM: Bacillus thuringiensis

<400> SEQUENCE: 1
tggccagcgc ca                                                      12

<210> SEQ ID NO 2
<211> LENGTH: 15
<212> TYPE: DNA
<213> ORGANISM: Bacillus thuringiensis

<400> SEQUENCE: 2
tgccagcgcc accat                                                   15

<210> SEQ ID NO 3
<211> LENGTH: 28
<212> TYPE: DNA
<213> ORGANISM: Bacillus thuringiensis

<400> SEQUENCE: 3
cggaggtatt ccatggagga aaataatc                                     28

<210> SEQ ID NO 4
<211> LENGTH: 34
<212> TYPE: DNA
<213> ORGANISM: Bacillus thuringiensis

<400> SEQUENCE: 4
cctatttgaa gccatggtaa ctcctccttt tatg                              34

<210> SEQ ID NO 5
<211> LENGTH: 3903
<212> TYPE: DNA
<213> ORGANISM: Bacillus thuringiensis
<220> FEATURE:
<221> NAME/KEY: CDS
<222> LOCATION: (264)..(3761)

<400> SEQUENCE: 5
ggatctgttt taatataagg gatttgtgcc cttctcgtta tattcttta ttagccccaa    60 aaactagtgc aactaaatat ttttataatt acactgatta aatactttat ttttgggagt   120
```

```
aagatttatg ctgaaatgta ataaaattcg ttccattttc tgtattttct cataaaatgt      180
ttcatatgct ttaaattgta gtaaagaaaa acagtacaaa cttaaaagga ctttagtaat      240
ttaataaaaa aaggggatag ttt atg gaa ata aat aat caa aac caa tgt gtg      293
                         Met Glu Ile Asn Asn Gln Asn Gln Cys Val
                          1               5                  10 cct tac aat tgt tta agt aat cct aag gag ata ata tta ggc gag gaa      341
Pro Tyr Asn Cys Leu Ser Asn Pro Lys Glu Ile Ile Leu Gly Glu Glu
             15                  20                  25 agg cta gaa aca ggg aat act gta gca gac att tca tta ggg ctt att      389
Arg Leu Glu Thr Gly Asn Thr Val Ala Asp Ile Ser Leu Gly Leu Ile
         30                  35                  40 aat ttt cta tat tct aat ttt gta cca gga gga gga ttt ata gta ggt      437
Asn Phe Leu Tyr Ser Asn Phe Val Pro Gly Gly Gly Phe Ile Val Gly
     45                  50                  55 tta cta gaa tta ata tgg gga ttt ata ggg cct tcg caa tgg gat att      485
Leu Leu Glu Leu Ile Trp Gly Phe Ile Gly Pro Ser Gln Trp Asp Ile
 60                  65                  70 ttt tta gct caa att gag caa ttg att agt caa aga ata gaa gaa ttt      533
Phe Leu Ala Gln Ile Glu Gln Leu Ile Ser Gln Arg Ile Glu Glu Phe
 75                  80                  85                  90 gct agg aat cag gca att tca aga ttg gag ggg cta agc aat ctt tat      581
Ala Arg Asn Gln Ala Ile Ser Arg Leu Glu Gly Leu Ser Asn Leu Tyr
                 95                 100                 105 aag gtc tat gtt aga gcg ttt agc gac tgg gag aaa gat cct act aat      629
Lys Val Tyr Val Arg Ala Phe Ser Asp Trp Glu Lys Asp Pro Thr Asn
             110                 115                 120 cct gct tta agg gaa gaa atg cgt ata caa ttt aat gac atg aat agt      677
Pro Ala Leu Arg Glu Glu Met Arg Ile Gln Phe Asn Asp Met Asn Ser
         125                 130                 135 gct ctc ata acg gct att cca ctt ttt aga gtt caa aat tat gaa gtt      725
Ala Leu Ile Thr Ala Ile Pro Leu Phe Arg Val Gln Asn Tyr Glu Val
     140                 145                 150 gct ctt tta tct gta tat gtt caa gcc gca aac tta cat tta tct att      773
Ala Leu Leu Ser Val Tyr Val Gln Ala Ala Asn Leu His Leu Ser Ile
155                 160                 165                 170 tta agg gat gtt tca gtt ttc gga gaa aga tgg gga tat gat aca gcg      821
Leu Arg Asp Val Ser Val Phe Gly Glu Arg Trp Gly Tyr Asp Thr Ala
                 175                 180                 185 act atc aat aat cgc tat agt gat ctg act agc ctt att cat gtt tat      869
Thr Ile Asn Asn Arg Tyr Ser Asp Leu Thr Ser Leu Ile His Val Tyr
             190                 195                 200 act aac cat tgt gtg gat acg tat aat cag gga tta agg cgt ttg gaa      917
Thr Asn His Cys Val Asp Thr Tyr Asn Gln Gly Leu Arg Arg Leu Glu
         205                 210                 215 ggt cgt ttt ctt agc gat tgg att gta tat aat cgt ttc cgg aga caa      965
Gly Arg Phe Leu Ser Asp Trp Ile Val Tyr Asn Arg Phe Arg Arg Gln
     220                 225                 230 ttg aca att tca gta tta gat att gtt gcg ttt ttt cca aat tat gat     1013
Leu Thr Ile Ser Val Leu Asp Ile Val Ala Phe Phe Pro Asn Tyr Asp
235                 240                 245                 250 att aga aca tat cca att caa aca gct act cag cta acg agg gaa gtc     1061
Ile Arg Thr Tyr Pro Ile Gln Thr Ala Thr Gln Leu Thr Arg Glu Val
                 255                 260                 265 tat ctg gat tta cct ttt att aat caa aat ctt tct cct gca gca agc     1109
Tyr Leu Asp Leu Pro Phe Ile Asn Gln Asn Leu Ser Pro Ala Ala Ser
             270                 275                 280 tat cca acc ttt tca gct gct gaa agt gct ata att aga agt cct cat     1157
Tyr Pro Thr Phe Ser Ala Ala Glu Ser Ala Ile Ile Arg Ser Pro His
         285                 290                 295
```

```
tta gta gac ttt tta aat agc ttt acc att tat aca gat agt ctg gca    1205
Leu Val Asp Phe Leu Asn Ser Phe Thr Ile Tyr Thr Asp Ser Leu Ala
300                 305                 310 cgt tat gca tat tgg gga ggg cac ttg gta aat tct ttc cgc aca gga    1253
Arg Tyr Ala Tyr Trp Gly Gly His Leu Val Asn Ser Phe Arg Thr Gly
315                 320                 325                 330 acc act act aat ttg ata aga tcc cct tta tat gga agg gaa gga aat    1301
Thr Thr Thr Asn Leu Ile Arg Ser Pro Leu Tyr Gly Arg Glu Gly Asn
                335                 340                 345 aca gag cgc ccc gta act att acc gca tca cct agc gta cca ata ttt    1349
Thr Glu Arg Pro Val Thr Ile Thr Ala Ser Pro Ser Val Pro Ile Phe
        350                 355                 360 aga aca ctt tca tat att aca ggc ctt gac aat tca aat cct gta gct    1397
Arg Thr Leu Ser Tyr Ile Thr Gly Leu Asp Asn Ser Asn Pro Val Ala
    365                 370                 375 gga atc gag gga gtg gaa ttc caa aat act ata agt aga agt atc tat    1445
Gly Ile Glu Gly Val Glu Phe Gln Asn Thr Ile Ser Arg Ser Ile Tyr
380                 385                 390 cgt aaa agc ggt cca ata gat tct ttt agt gaa tta cca cct caa gat    1493
Arg Lys Ser Gly Pro Ile Asp Ser Phe Ser Glu Leu Pro Pro Gln Asp
395                 400                 405                 410 gcc agc gta tct cct gca att ggg tat agt cac cgt tta tgc cat gca    1541
Ala Ser Val Ser Pro Ala Ile Gly Tyr Ser His Arg Leu Cys His Ala
                415                 420                 425 aca ttt tta gaa cgg att agt gga cca aga ata gca ggc acc gta ttt    1589
Thr Phe Leu Glu Arg Ile Ser Gly Pro Arg Ile Ala Gly Thr Val Phe
        430                 435                 440 tct tgg aca cac cgt agt gcc agc cct act aat gaa gta agt cca tct    1637
Ser Trp Thr His Arg Ser Ala Ser Pro Thr Asn Glu Val Ser Pro Ser
    445                 450                 455 aga att aca caa att cca tgg gta aag gcg cat act ctt gca tct ggt    1685
Arg Ile Thr Gln Ile Pro Trp Val Lys Ala His Thr Leu Ala Ser Gly
460                 465                 470 gcc tcc gtc att aaa ggt cct gga ttt aca ggt gga gat att ctg act    1733
Ala Ser Val Ile Lys Gly Pro Gly Phe Thr Gly Gly Asp Ile Leu Thr
475                 480                 485                 490 agg aat agt atg ggc gag ctg ggg acc tta cga gta acc ttc aca gga    1781
Arg Asn Ser Met Gly Glu Leu Gly Thr Leu Arg Val Thr Phe Thr Gly
                495                 500                 505 aga tta cca caa agt tat tat ata cgt ttc cgt tat gct tcg gta gca    1829
Arg Leu Pro Gln Ser Tyr Tyr Ile Arg Phe Arg Tyr Ala Ser Val Ala
        510                 515                 520 aat agg agt ggt aca ttt aga tat tca cag cca cct tcg tat gga att    1877
Asn Arg Ser Gly Thr Phe Arg Tyr Ser Gln Pro Pro Ser Tyr Gly Ile
    525                 530                 535 tca ttt cca aaa act atg gac gca ggt gaa cca cta aca tct cgt tcg    1925
Ser Phe Pro Lys Thr Met Asp Ala Gly Glu Pro Leu Thr Ser Arg Ser
540                 545                 550 ttc gct cat aca aca ctc ttc act cca ata acc ttt tca cga gct caa    1973
Phe Ala His Thr Thr Leu Phe Thr Pro Ile Thr Phe Ser Arg Ala Gln
555                 560                 565                 570 gaa gaa ttt gat cta tac atc caa tcg ggt gtt tat ata gat cga att    2021
Glu Glu Phe Asp Leu Tyr Ile Gln Ser Gly Val Tyr Ile Asp Arg Ile
                575                 580                 585 gaa ttt ata ccg gtt act gca aca ttt gag gca gaa tat gat tta gaa    2069
Glu Phe Ile Pro Val Thr Ala Thr Phe Glu Ala Glu Tyr Asp Leu Glu
        590                 595                 600 aga gcg caa aag gtg gtg aat gcc ctg ttt acg tct aca aac caa cta    2117
Arg Ala Gln Lys Val Val Asn Ala Leu Phe Thr Ser Thr Asn Gln Leu
    605                 610                 615
```

```
ggg cta aaa aca gat gtg acg gat tat cat att gat cag gta tcc aat    2165
Gly Leu Lys Thr Asp Val Thr Asp Tyr His Ile Asp Gln Val Ser Asn
    620                 625                 630 cta gtt gcg tgt tta tcg gat gaa ttt tgt ctg gat gaa aag aga gaa    2213
Leu Val Ala Cys Leu Ser Asp Glu Phe Cys Leu Asp Glu Lys Arg Glu
635                 640                 645                 650 ttg tcc gag aaa gtt aaa cat gca aag cga ctc agt gat gag cgg aat    2261
Leu Ser Glu Lys Val Lys His Ala Lys Arg Leu Ser Asp Glu Arg Asn
                655                 660                 665 tta ctt caa gat cca aac ttc aga ggg atc aat agg caa cca gac cgt    2309
Leu Leu Gln Asp Pro Asn Phe Arg Gly Ile Asn Arg Gln Pro Asp Arg
            670                 675                 680 ggc tgg aga gga agt acg gat att act atc caa gga gga gat gac gta    2357
Gly Trp Arg Gly Ser Thr Asp Ile Thr Ile Gln Gly Gly Asp Asp Val
        685                 690                 695 ttc aaa gag aat tac gtt acg cta ccg ggt acc ttt gat gag tgc tat    2405
Phe Lys Glu Asn Tyr Val Thr Leu Pro Gly Thr Phe Asp Glu Cys Tyr
    700                 705                 710 cca acg tat tta tat caa aaa ata gat gag tcg aaa tta aaa gcc tat    2453
Pro Thr Tyr Leu Tyr Gln Lys Ile Asp Glu Ser Lys Leu Lys Ala Tyr
715                 720                 725                 730 acc cgt tat caa tta aga ggg tat atc gaa gat agt caa gac tta gaa    2501
Thr Arg Tyr Gln Leu Arg Gly Tyr Ile Glu Asp Ser Gln Asp Leu Glu
                735                 740                 745 atc tat tta att cgt tac aat gca aaa cac gaa ata gta aat gta cca    2549
Ile Tyr Leu Ile Arg Tyr Asn Ala Lys His Glu Ile Val Asn Val Pro
            750                 755                 760 ggt aca gga agt tta tgg cct ctt tct gta gaa aat caa att gga cct    2597
Gly Thr Gly Ser Leu Trp Pro Leu Ser Val Glu Asn Gln Ile Gly Pro
        765                 770                 775 tgt gga gaa ccg aat cga tgc gcg cca cac ctt gaa tgg aat cct gat    2645
Cys Gly Glu Pro Asn Arg Cys Ala Pro His Leu Glu Trp Asn Pro Asp
    780                 785                 790 tta cac tgt tcc tgc aga gac ggg gaa aaa tgt gca cat cat tct cat    2693
Leu His Cys Ser Cys Arg Asp Gly Glu Lys Cys Ala His His Ser His
795                 800                 805                 810 cat ttc tct ttg gac att gat gtt gga tgt aca gac tta aat gag gac    2741
His Phe Ser Leu Asp Ile Asp Val Gly Cys Thr Asp Leu Asn Glu Asp
                815                 820                 825 tta ggt gta tgg gtg ata ttc aag att aag acg caa gat ggc cac gca    2789
Leu Gly Val Trp Val Ile Phe Lys Ile Lys Thr Gln Asp Gly His Ala
            830                 835                 840 cga cta ggg aat cta gag ttt ctc gaa gag aaa cca tta tta gga gaa    2837
Arg Leu Gly Asn Leu Glu Phe Leu Glu Glu Lys Pro Leu Leu Gly Glu
        845                 850                 855 gca cta gct cgt gtg aaa aga gcg gag aaa aaa tgg aga gac aaa cgc    2885
Ala Leu Ala Arg Val Lys Arg Ala Glu Lys Lys Trp Arg Asp Lys Arg
    860                 865                 870 gaa aca tta caa ttg gaa aca act atc gtt tat aaa gag gca aaa gaa    2933
Glu Thr Leu Gln Leu Glu Thr Thr Ile Val Tyr Lys Glu Ala Lys Glu
875                 880                 885                 890 tct gta gat gct tta ttt gta aac tct caa tat gat aga tta caa gcg    2981
Ser Val Asp Ala Leu Phe Val Asn Ser Gln Tyr Asp Arg Leu Gln Ala
                895                 900                 905 gat acg aac atc gcg atg att cat gcg gca gat aaa cgc gtt cat aga    3029
Asp Thr Asn Ile Ala Met Ile His Ala Ala Asp Lys Arg Val His Arg
            910                 915                 920 att cga gaa gcg tat ctg ccg gag ctg tct gtg att ccg ggt gtc aat    3077
Ile Arg Glu Ala Tyr Leu Pro Glu Leu Ser Val Ile Pro Gly Val Asn
        925                 930                 935
```

| | | | | | | | | | | | | | | | |
|---|---|---|---|---|---|---|---|---|---|---|---|---|---|---|---|
| gcg | gct | att | ttt | gaa | gaa | tta | gaa | gag | cgt | att | ttc | act | gca | ttt | tcc | 3125 |
| Ala | Ala | Ile | Phe | Glu | Glu | Leu | Glu | Glu | Arg | Ile | Phe | Thr | Ala | Phe | Ser |
| | 940 | | | | 945 | | | | | 950 | | | | | |

```
gcg gct att ttt gaa gaa tta gaa gag cgt att ttc act gca ttt tcc      3125
Ala Ala Ile Phe Glu Glu Leu Glu Glu Arg Ile Phe Thr Ala Phe Ser
    940             945                 950 cta tat gat gcg aga aat att att aaa aat ggc gat ttc aat aat ggc      3173
Leu Tyr Asp Ala Arg Asn Ile Ile Lys Asn Gly Asp Phe Asn Asn Gly
955             960                 965                 970 tta tta tgc tgg aac gtg aaa ggg cat gta gag gta gaa gaa caa aac      3221
Leu Leu Cys Trp Asn Val Lys Gly His Val Glu Val Glu Glu Gln Asn
            975                 980                 985 aat cac cgt tca gtc ctg gtt atc cca gaa tgg gag gca gaa  gtg tca     3269
Asn His Arg Ser Val Leu Val Ile Pro Glu Trp Glu Ala Glu  Val Ser
                990                 995                  1000 caa gag gtt  cgt gtc tgt cca ggt  cgt ggc tat atc ctt  cgt gtt       3314
Gln Glu Val  Arg Val Cys Pro Gly  Arg Gly Tyr Ile Leu  Arg Val
            1005             1010                 1015 aca gcg tac aaa gag gga tat gga  gaa ggt tgc gta acg  atc cat        3359
Thr Ala Tyr Lys Glu Gly Tyr Gly  Glu Gly Cys Val Thr  Ile His
            1020            1025                 1030 gag atc gag aac aat aca gac gaa ctg aaa ttc aac aac tgt gta          3404
Glu Ile Glu Asn Asn Thr Asp Glu Leu Lys Phe Asn Asn Cys Val
            1035            1040                1045 gaa gag gaa gta tat cca aac aac acg gta acg tgt att  aat tat         3449
Glu Glu Glu Val Tyr Pro Asn Asn Thr Val Thr Cys Ile  Asn Tyr
            1050            1055                 1060 act gcg act caa gaa gaa tat gag ggt acg tac act tct cgt aat          3494
Thr Ala Thr Gln Glu Glu Tyr Glu Gly Thr Tyr Thr Ser Arg Asn
            1065            1070                1075 cga gga tat gac gaa gcc tat ggt aat aac cct tcc gta  cca gct         3539
Arg Gly Tyr Asp Glu Ala Tyr Gly Asn Asn Pro Ser Val  Pro Ala
            1080            1085                 1090 gat tat gcg tca gtc tat gaa gaa aaa tcg tat aca gat aga cga          3584
Asp Tyr Ala Ser Val Tyr Glu Glu Lys Ser Tyr Thr Asp Arg Arg
            1095            1100                1105 aga gag aat cct tgt gaa tct aac aga gga tat gga gat tac aca          3629
Arg Glu Asn Pro Cys Glu Ser Asn Arg Gly Tyr Gly Asp Tyr Thr
            1110            1115                1120 cca cta cca gct ggt tat gta aca aag gaa tta gag tac ttc cca          3674
Pro Leu Pro Ala Gly Tyr Val Thr Lys Glu Leu Glu Tyr Phe Pro
            1125            1130                1135 gag acc gat aag gta tgg att gag att gga gaa aca gaa gga aca          3719
Glu Thr Asp Lys Val Trp Ile Glu Ile Gly Glu Thr Glu Gly Thr
            1140            1145                1150 ttc atc gtg gac agc gtg gaa tta ctc ctt atg gag gaa tag              3761
Phe Ile Val Asp Ser Val Glu Leu Leu Leu Met Glu Glu
            1155            1160 gaccatccga gtatagcagt ttaataaata ttaattaaaa tagtagtcta acttccgttc    3821
caattaaata agtaaattac agttgtaaaa aaaaacgaac attactcttc aaagagcgat    3881
gtccgttttt tatatggtgt gt                                             3903
```

<210> SEQ ID NO 6
<211> LENGTH: 1165
<212> TYPE: PRT
<213> ORGANISM: Bacillus thuringiensis

<400> SEQUENCE: 6

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
            20                  25                  30

-continued

```
Thr Val Ala Asp Ile Ser Leu Gly Leu Ile Asn Phe Leu Tyr Ser Asn
         35                  40                  45

Phe Val Pro Gly Gly Phe Ile Val Gly Leu Leu Glu Leu Ile Trp
 50                  55                  60

Gly Phe Ile Gly Pro Ser Gln Trp Asp Ile Phe Leu Ala Gln Ile Glu
 65                  70                  75                  80

Gln Leu Ile Ser Gln Arg Ile Glu Glu Phe Ala Arg Asn Gln Ala Ile
                 85                  90                  95

Ser Arg Leu Glu Gly Leu Ser Asn Leu Tyr Lys Val Tyr Val Arg Ala
                100                 105                 110

Phe Ser Asp Trp Glu Lys Asp Pro Thr Asn Pro Ala Leu Arg Glu Glu
                115                 120                 125

Met Arg Ile Gln Phe Asn Asp Met Asn Ser Ala Leu Ile Thr Ala Ile
        130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
                180                 185                 190

Ser Asp Leu Thr Ser Leu Ile His Val Tyr Thr Asn His Cys Val Asp
                195                 200                 205

Thr Tyr Asn Gln Gly Leu Arg Arg Leu Glu Gly Arg Phe Leu Ser Asp
        210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Val Tyr Leu Asp Leu Pro Phe
                260                 265                 270

Ile Asn Gln Asn Leu Ser Pro Ala Ala Ser Tyr Pro Thr Phe Ser Ala
        275                 280                 285

Ala Glu Ser Ala Ile Ile Arg Ser Pro His Leu Val Asp Phe Leu Asn
290                 295                 300

Ser Phe Thr Ile Tyr Thr Asp Ser Leu Ala Arg Tyr Ala Tyr Trp Gly
305                 310                 315                 320

Gly His Leu Val Asn Ser Phe Arg Thr Gly Thr Thr Asn Leu Ile
                325                 330                 335

Arg Ser Pro Leu Tyr Gly Arg Glu Gly Asn Thr Glu Arg Pro Val Thr
                340                 345                 350

Ile Thr Ala Ser Pro Ser Val Pro Ile Phe Arg Thr Leu Ser Tyr Ile
        355                 360                 365

Thr Gly Leu Asp Asn Ser Asn Pro Val Ala Gly Ile Glu Gly Val Glu
370                 375                 380

Phe Gln Asn Thr Ile Ser Arg Ser Ile Tyr Arg Lys Ser Gly Pro Ile
385                 390                 395                 400

Asp Ser Phe Ser Glu Leu Pro Pro Gln Asp Ala Ser Val Ser Pro Ala
                405                 410                 415

Ile Gly Tyr Ser His Arg Leu Cys His Ala Thr Phe Leu Glu Arg Ile
        420                 425                 430

Ser Gly Pro Arg Ile Ala Gly Thr Val Phe Ser Trp Thr His Arg Ser
                435                 440                 445
```

-continued

```
Ala Ser Pro Thr Asn Glu Val Ser Pro Ser Arg Ile Thr Gln Ile Pro
    450                 455                 460
Trp Val Lys Ala His Thr Leu Ala Ser Gly Ala Ser Val Ile Lys Gly
465                 470                 475                 480
Pro Gly Phe Thr Gly Gly Asp Ile Leu Thr Arg Asn Ser Met Gly Glu
                485                 490                 495
Leu Gly Thr Leu Arg Val Thr Phe Thr Gly Arg Leu Pro Gln Ser Tyr
            500                 505                 510
Tyr Ile Arg Phe Arg Tyr Ala Ser Val Ala Asn Arg Ser Gly Thr Phe
        515                 520                 525
Arg Tyr Ser Gln Pro Pro Ser Tyr Gly Ile Ser Phe Pro Lys Thr Met
    530                 535                 540
Asp Ala Gly Glu Pro Leu Thr Ser Arg Ser Phe Ala His Thr Thr Leu
545                 550                 555                 560
Phe Thr Pro Ile Thr Phe Ser Arg Ala Gln Glu Glu Phe Asp Leu Tyr
                565                 570                 575
Ile Gln Ser Gly Val Tyr Ile Asp Arg Ile Glu Phe Ile Pro Val Thr
            580                 585                 590
Ala Thr Phe Glu Ala Glu Tyr Asp Leu Glu Arg Ala Gln Lys Val Val
        595                 600                 605
Asn Ala Leu Phe Thr Ser Thr Asn Gln Leu Gly Leu Lys Thr Asp Val
    610                 615                 620
Thr Asp Tyr His Ile Asp Gln Val Ser Asn Leu Val Ala Cys Leu Ser
625                 630                 635                 640
Asp Glu Phe Cys Leu Asp Glu Lys Arg Glu Leu Ser Glu Lys Val Lys
                645                 650                 655
His Ala Lys Arg Leu Ser Asp Glu Arg Asn Leu Leu Gln Asp Pro Asn
            660                 665                 670
Phe Arg Gly Ile Asn Arg Gln Pro Asp Arg Gly Trp Arg Gly Ser Thr
        675                 680                 685
Asp Ile Thr Ile Gln Gly Gly Asp Asp Val Phe Lys Glu Asn Tyr Val
    690                 695                 700
Thr Leu Pro Gly Thr Phe Asp Glu Cys Tyr Pro Thr Tyr Leu Tyr Gln
705                 710                 715                 720
Lys Ile Asp Glu Ser Lys Leu Lys Ala Tyr Thr Arg Tyr Gln Leu Arg
                725                 730                 735
Gly Tyr Ile Glu Asp Ser Gln Asp Leu Glu Ile Tyr Leu Ile Arg Tyr
            740                 745                 750
Asn Ala Lys His Glu Ile Val Asn Val Pro Gly Thr Gly Ser Leu Trp
        755                 760                 765
Pro Leu Ser Val Glu Asn Gln Ile Gly Pro Cys Gly Glu Pro Asn Arg
    770                 775                 780
Cys Ala Pro His Leu Glu Trp Asn Pro Asp Leu His Cys Ser Cys Arg
785                 790                 795                 800
Asp Gly Glu Lys Cys Ala His His Ser His His Phe Ser Leu Asp Ile
                805                 810                 815
Asp Val Gly Cys Thr Asp Leu Asn Glu Asp Leu Gly Val Trp Val Ile
            820                 825                 830
Phe Lys Ile Lys Thr Gln Asp Gly His Ala Arg Leu Gly Asn Leu Glu
        835                 840                 845
Phe Leu Glu Glu Lys Pro Leu Leu Gly Glu Ala Leu Ala Arg Val Lys
    850                 855                 860
```

-continued

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
            885                 890                 895

Val Asn Ser Gln Tyr Asp Arg Leu Gln Ala Asp Thr Asn Ile Ala Met
                900                 905                 910

Ile His Ala Ala Asp Lys Arg Val His Arg Ile Arg Glu Ala Tyr Leu
        915                 920                 925

Pro Glu Leu Ser Val Ile Pro Gly Val Asn Ala Ala Ile Phe Glu Glu
    930                 935                 940

Leu Glu Glu Arg Ile Phe Thr Ala Phe Ser Leu Tyr Asp Ala Arg Asn
945                 950                 955                 960

Ile Ile Lys Asn Gly Asp Phe Asn Asn Gly Leu Leu Cys Trp Asn Val
            965                 970                 975

Lys Gly His Val Glu Val Glu Glu Gln Asn Asn His Arg Ser Val Leu
                980                 985                 990

Val Ile Pro Glu Trp Glu Ala Glu Val Ser Gln Glu Val Arg Val Cys
        995                1000                1005

Pro Gly Arg Gly Tyr Ile Leu Arg Val Thr Ala Tyr Lys Glu Gly
    1010                1015                1020

Tyr Gly Glu Gly Cys Val Thr Ile His Glu Ile Glu Asn Asn Thr
    1025                1030                1035

Asp Glu Leu Lys Phe Asn Asn Cys Val Glu Glu Glu Val Tyr Pro
    1040                1045                1050

Asn Asn Thr Val Thr Cys Ile Asn Tyr Thr Ala Thr Gln Glu Glu
    1055                1060                1065

Tyr Glu Gly Thr Tyr Thr Ser Arg Asn Arg Gly Tyr Asp Glu Ala
    1070                1075                1080

Tyr Gly Asn Asn Pro Ser Val Pro Ala Asp Tyr Ala Ser Val Tyr
    1085                1090                1095

Glu Glu Lys Ser Tyr Thr Asp Arg Arg Arg Glu Asn Pro Cys Glu
    1100                1105                1110

Ser Asn Arg Gly Tyr Gly Asp Tyr Thr Pro Leu Pro Ala Gly Tyr
    1115                1120                1125

Val Thr Lys Glu Leu Glu Tyr Phe Pro Glu Thr Asp Lys Val Trp
    1130                1135                1140

Ile Glu Ile Gly Glu Thr Glu Gly Thr Phe Ile Val Asp Ser Val
    1145                1150                1155

Glu Leu Leu Leu Met Glu Glu
    1160                1165

<210> SEQ ID NO 7
<211> LENGTH: 3923
<212> TYPE: DNA
<213> ORGANISM: Bacillus thuringiensis
<220> FEATURE:
<221> NAME/KEY: CDS
<222> LOCATION: (243)..(3803)

<400> SEQUENCE: 7
aatagaatct caaatctcga tgactgctta gtcttttaa tactgtctac ttgacagggg      60
taggaacata atcggtcaat tttaaatatg gggcatatat tgatatttta taaaatttgt     120
tacgtttttt gtatttttc ataagatgtg tcatatgtat taaatcgtgg taatgaaaaa     180
cagtatcaaa ctatcagaac tttggtagtt taataaaaaa acggaggtat tttatggagg     240

-continued

```
aa aat aat caa aat caa tgc ata cct tac aat tgt tta agt aat cct         287
   Asn Asn Gln Asn Gln Cys Ile Pro Tyr Asn Cys Leu Ser Asn Pro
   1               5                   10                  15 gaa gaa gta ctt ttg gat gga gaa cgg ata tca act ggt aat tca tca         335
Glu Glu Val Leu Leu Asp Gly Glu Arg Ile Ser Thr Gly Asn Ser Ser
                20                  25                  30 att gat att tct ctg tca ctt gtt cag ttt atg gta tct aac ttt gta         383
Ile Asp Ile Ser Leu Ser Leu Val Gln Phe Met Val Ser Asn Phe Val
            35                  40                  45 cca ggg gga gga ttt tta gtt gga tta ata gat ttt gta tgg gga ata         431
Pro Gly Gly Gly Phe Leu Val Gly Leu Ile Asp Phe Val Trp Gly Ile
        50                  55                  60 gtt ggc cct tct caa tgg gat gca ttt cta gta caa att gaa caa tta         479
Val Gly Pro Ser Gln Trp Asp Ala Phe Leu Val Gln Ile Glu Gln Leu
    65                  70                  75 att aat gaa aga ata gct gaa ttt gct agg aat gct gct att gct aat         527
Ile Asn Glu Arg Ile Ala Glu Phe Ala Arg Asn Ala Ala Ile Ala Asn
80                  85                  90                  95 tta gaa gga tta gaa aac aat tta aat ata tat gtg gaa gca ttt aaa         575
Leu Glu Gly Leu Glu Asn Asn Leu Asn Ile Tyr Val Glu Ala Phe Lys
                100                 105                 110 gaa tgg gaa gaa gat cct aat aat cca gaa acc agg acc aga gta att         623
Glu Trp Glu Glu Asp Pro Asn Asn Pro Glu Thr Arg Thr Arg Val Ile
            115                 120                 125 gat cgc ttt cgt ata ctt gat ggg cta ctt gaa agg gac att cct tcg         671
Asp Arg Phe Arg Ile Leu Asp Gly Leu Leu Glu Arg Asp Ile Pro Ser
        130                 135                 140 ttt cga att tct gga ttt gaa gta ccc ctt tta tcc gtt tat gct caa         719
Phe Arg Ile Ser Gly Phe Glu Val Pro Leu Leu Ser Val Tyr Ala Gln
    145                 150                 155 gcg gcc aat ctg cat cta gct ata tta aga gat tct gta att ttt gga         767
Ala Ala Asn Leu His Leu Ala Ile Leu Arg Asp Ser Val Ile Phe Gly
160                 165                 170                 175 gaa aga tgg gga ttg aca acg ata aat gtc aat gaa aac tat aat aga         815
Glu Arg Trp Gly Leu Thr Thr Ile Asn Val Asn Glu Asn Tyr Asn Arg
                180                 185                 190 cta att agg cat att gat gaa tat gct gat cac tgt gca aat acg tat         863
Leu Ile Arg His Ile Asp Glu Tyr Ala Asp His Cys Ala Asn Thr Tyr
            195                 200                 205 aat cgg gga tta aat aat tta ccg aaa tct acg tat caa gat tgg ata         911
Asn Arg Gly Leu Asn Asn Leu Pro Lys Ser Thr Tyr Gln Asp Trp Ile
        210                 215                 220 aca tat aat cga tta cgg aga gac tta aca ttg act gta tta gat atc         959
Thr Tyr Asn Arg Leu Arg Arg Asp Leu Thr Leu Thr Val Leu Asp Ile
    225                 230                 235 gcc gct ttc ttt cca aac tat gac aat agg aga tat cca att cag cca        1007
Ala Ala Phe Phe Pro Asn Tyr Asp Asn Arg Arg Tyr Pro Ile Gln Pro
240                 245                 250                 255 gtt ggt caa cta aca agg gaa gtt tat acg gac cca tta att aat ttt        1055
Val Gly Gln Leu Thr Arg Glu Val Tyr Thr Asp Pro Leu Ile Asn Phe
                260                 265                 270 aat cca cag tta cag tct gta gct caa tta cct act ttt aac gtt atg        1103
Asn Pro Gln Leu Gln Ser Val Ala Gln Leu Pro Thr Phe Asn Val Met
            275                 280                 285 gag agc agc gca att aga aat cct cat tta ttt gat ata ttg aat aat        1151
Glu Ser Ser Ala Ile Arg Asn Pro His Leu Phe Asp Ile Leu Asn Asn
        290                 295                 300 ctt aca atc ttt acg gat tgg ttt agt gtt gga cgc aat ttt tat tgg        1199
Leu Thr Ile Phe Thr Asp Trp Phe Ser Val Gly Arg Asn Phe Tyr Trp
    305                 310                 315
```

```
gga gga cat cga gta ata tct agc ctt ata gga ggt ggt aac ata aca    1247
Gly Gly His Arg Val Ile Ser Ser Leu Ile Gly Gly Gly Asn Ile Thr
320             325                 330                 335 tct cct ata tat gga aga gag gcg aac cag gag cct cca aga tcc ttt    1295
Ser Pro Ile Tyr Gly Arg Glu Ala Asn Gln Glu Pro Pro Arg Ser Phe
                340                 345                 350 act ttt aat gga ccg gta ttt agg act tta tca aat cct act tta cga    1343
Thr Phe Asn Gly Pro Val Phe Arg Thr Leu Ser Asn Pro Thr Leu Arg
            355                 360                 365 tta tta cag caa cct tgg cca gcg cca cca ttt aat tta cgt ggt gtt    1391
Leu Leu Gln Gln Pro Trp Pro Ala Pro Pro Phe Asn Leu Arg Gly Val
        370                 375                 380 gaa gga gta gaa ttt tct aca cct aca aat agc ttt acg tat cga gga    1439
Glu Gly Val Glu Phe Ser Thr Pro Thr Asn Ser Phe Thr Tyr Arg Gly
385                 390                 395 aga ggt acg gtt gat tct tta act gaa tta ccg cct gag gat aat agt    1487
Arg Gly Thr Val Asp Ser Leu Thr Glu Leu Pro Pro Glu Asp Asn Ser
400             405                 410                 415 gtg cca cct cgc gaa gga tat agt cat cgt tta tgt cat gca act ttt    1535
Val Pro Pro Arg Glu Gly Tyr Ser His Arg Leu Cys His Ala Thr Phe
                420                 425                 430 gtt caa aga tct gga aca cct ttt tta aca act ggt gta gta ttt tct    1583
Val Gln Arg Ser Gly Thr Pro Phe Leu Thr Thr Gly Val Val Phe Ser
            435                 440                 445 tgg acg cat cgt agt gca act ctt aca aat aca att gat cca gag aga    1631
Trp Thr His Arg Ser Ala Thr Leu Thr Asn Thr Ile Asp Pro Glu Arg
        450                 455                 460 att aat caa ata cct tta gtg aaa gga ttt aga gtt tgg ggg ggc acc    1679
Ile Asn Gln Ile Pro Leu Val Lys Gly Phe Arg Val Trp Gly Gly Thr
465                 470                 475 tct gtc att aca gga cca gga ttt aca gga ggg gat atc ctt cga aga    1727
Ser Val Ile Thr Gly Pro Gly Phe Thr Gly Gly Asp Ile Leu Arg Arg
480             485                 490                 495 aat acc ttt ggt gat ttt gta tct cta caa gtc aat att aat tca cca    1775
Asn Thr Phe Gly Asp Phe Val Ser Leu Gln Val Asn Ile Asn Ser Pro
                500                 505                 510 att acc caa aga tac cgt tta aga ttt cgt tac gct tcc agt agg gat    1823
Ile Thr Gln Arg Tyr Arg Leu Arg Phe Arg Tyr Ala Ser Ser Arg Asp
            515                 520                 525 gca cga gtt ata gta tta aca gga gcg gca tcc aca gga gtg gga ggc    1871
Ala Arg Val Ile Val Leu Thr Gly Ala Ala Ser Thr Gly Val Gly Gly
        530                 535                 540 caa gtt agt gta aat atg cct ctt cag aaa act atg gaa ata ggg gag    1919
Gln Val Ser Val Asn Met Pro Leu Gln Lys Thr Met Glu Ile Gly Glu
545                 550                 555 aac tta aca tct aga aca ttt aga tat acc gat ttt agt aat cct ttt    1967
Asn Leu Thr Ser Arg Thr Phe Arg Tyr Thr Asp Phe Ser Asn Pro Phe
560             565                 570                 575 tca ttt aga gct aat cca gat ata att ggg ata agt gaa caa cct cta    2015
Ser Phe Arg Ala Asn Pro Asp Ile Ile Gly Ile Ser Glu Gln Pro Leu
                580                 585                 590 ttt ggt gca ggt tct att agt agc ggt gaa ctt tat ata gat aaa att    2063
Phe Gly Ala Gly Ser Ile Ser Ser Gly Glu Leu Tyr Ile Asp Lys Ile
            595                 600                 605 gaa att att cta gca gat gca aca ttt gaa gca gaa tct gat tta gaa    2111
Glu Ile Ile Leu Ala Asp Ala Thr Phe Glu Ala Glu Ser Asp Leu Glu
        610                 615                 620 aga gca caa aag gcg gtg aat gcc ctg ttt act tct tcc aat caa atc    2159
Arg Ala Gln Lys Ala Val Asn Ala Leu Phe Thr Ser Ser Asn Gln Ile
625                 630                 635
```

-continued

| | | |
|---|---|---|
| ggg tta aaa acc gat gtg acg gat tat cat att gat caa gta tcc aat<br>Gly Leu Lys Thr Asp Val Thr Asp Tyr His Ile Asp Gln Val Ser Asn<br>640                     645                       650                      655 | 2207 |
| tta gtg gat tgt tta tca gat gaa ttt tgt ctg gat gaa aag cga gaa<br>Leu Val Asp Cys Leu Ser Asp Glu Phe Cys Leu Asp Glu Lys Arg Glu<br>                   660                       665                       670 | 2255 |
| ttg tcc gag aaa gtc aaa cat gcg aag cga ctc agt gat gag cgg aat<br>Leu Ser Glu Lys Val Lys His Ala Lys Arg Leu Ser Asp Glu Arg Asn<br>               675                       680                       685 | 2303 |
| tta ctt caa gat cca aac ttc aga ggg atc aat aga caa cca gac cgt<br>Leu Leu Gln Asp Pro Asn Phe Arg Gly Ile Asn Arg Gln Pro Asp Arg<br>690                     695                       700 | 2351 |
| ggc tgg aga gga agt aca gat att acc atc caa gga gga gat gac gta<br>Gly Trp Arg Gly Ser Thr Asp Ile Thr Ile Gln Gly Gly Asp Asp Val<br>     705                     710                       715 | 2399 |
| ttc aaa gag aat tac gtc aca cta ccg ggt acc gtt gat gag tgc tat<br>Phe Lys Glu Asn Tyr Val Thr Leu Pro Gly Thr Val Asp Glu Cys Tyr<br>720                     725                       730                       735 | 2447 |
| cca acg tat tta tat cag aaa ata gat gag tcg aaa tta aaa gct tat<br>Pro Thr Tyr Leu Tyr Gln Lys Ile Asp Glu Ser Lys Leu Lys Ala Tyr<br>                   740                       745                       750 | 2495 |
| acc cgt tat gaa tta aga ggg tat atc gaa gat agt caa gac tta gaa<br>Thr Arg Tyr Glu Leu Arg Gly Tyr Ile Glu Asp Ser Gln Asp Leu Glu<br>               755                       760                       765 | 2543 |
| atc tat ttg atc cgt tac aat gca aaa cac gaa ata gta aat gtg cca<br>Ile Tyr Leu Ile Arg Tyr Asn Ala Lys His Glu Ile Val Asn Val Pro<br>         770                     775                       780 | 2591 |
| ggc acg ggt tcc tta tgg ccg ctt tca gcc caa agt cca atc gga aag<br>Gly Thr Gly Ser Leu Trp Pro Leu Ser Ala Gln Ser Pro Ile Gly Lys<br>785                     790                       795 | 2639 |
| tgt gga gaa ccg aat cga tgc gcg cca cac ctt gaa tgg aat cct gat<br>Cys Gly Glu Pro Asn Arg Cys Ala Pro His Leu Glu Trp Asn Pro Asp<br>800                     805                       810                       815 | 2687 |
| cta gat tgt tcc tgc aga gac ggg gaa aaa tgt gca cat cat tcc cat<br>Leu Asp Cys Ser Cys Arg Asp Gly Glu Lys Cys Ala His His Ser His<br>                   820                       825                       830 | 2735 |
| cat ttc acc ttg gat att gat gtt gga tgt aca gac tta aat gag gac<br>His Phe Thr Leu Asp Ile Asp Val Gly Cys Thr Asp Leu Asn Glu Asp<br>               835                       840                       845 | 2783 |
| tta ggt gta tgg gtg ata ttc aag att aag acg caa gat ggc cat gca<br>Leu Gly Val Trp Val Ile Phe Lys Ile Lys Thr Gln Asp Gly His Ala<br>     850                     855                       860 | 2831 |
| aga cta ggg aat cta gag ttt ctc gaa gag aaa cca tta tta ggg gaa<br>Arg Leu Gly Asn Leu Glu Phe Leu Glu Glu Lys Pro Leu Leu Gly Glu<br>865                     870                       875 | 2879 |
| gca cta gct cgt gtg aaa aga gcg gag aag aag tgg aga gac aaa cga<br>Ala Leu Ala Arg Val Lys Arg Ala Glu Lys Lys Trp Arg Asp Lys Arg<br>880                     885                       890                       895 | 2927 |
| gag aaa ctg cag ttg gaa aca aat att gtt tat aaa gag gca aaa gaa<br>Glu Lys Leu Gln Leu Glu Thr Asn Ile Val Tyr Lys Glu Ala Lys Glu<br>               900                       905                       910 | 2975 |
| tct gta gat gct tta ttt gta aac tct caa tat gat aga tta caa gtg<br>Ser Val Asp Ala Leu Phe Val Asn Ser Gln Tyr Asp Arg Leu Gln Val<br>               915                       920                       925 | 3023 |
| gat acg aac atc gcg atg att cat gcg gca gat aaa cgc gtt cat aga<br>Asp Thr Asn Ile Ala Met Ile His Ala Ala Asp Lys Arg Val His Arg<br>         930                     935                       940 | 3071 |
| atc cgg gaa gcg tat ctg cca gag ttg tct gtg att cca ggt gtc aat<br>Ile Arg Glu Ala Tyr Leu Pro Glu Leu Ser Val Ile Pro Gly Val Asn<br>945                     950                       955 | 3119 |

```
gcg gcc att ttc gaa gaa tta gag gga cgt att ttt aca gcg tat tcc      3167
Ala Ala Ile Phe Glu Glu Leu Glu Gly Arg Ile Phe Thr Ala Tyr Ser
960             965                 970                 975 tta tat gat gcg aga aat gtc att aaa aat ggc gat ttc aat aat ggc      3215
Leu Tyr Asp Ala Arg Asn Val Ile Lys Asn Gly Asp Phe Asn Asn Gly
            980                 985                 990 tta tta tgc tgg aac gtg aaa ggt cat gta gat gta gaa gag caa aac      3263
Leu Leu Cys Trp Asn Val Lys Gly His Val Asp Val Glu Glu Gln Asn
        995                 1000                1005 aac cac cgt tcg gtc ctt gtt atc cca gaa tgg gag gca gaa gtg          3308
Asn His Arg Ser Val Leu Val Ile Pro Glu Trp Glu Ala Glu Val
    1010                1015                1020 tca caa gag gtt cgt gtc tgt cca ggt cgt ggc tat atc ctt cgt          3353
Ser Gln Glu Val Arg Val Cys Pro Gly Arg Gly Tyr Ile Leu Arg
    1025                1030                1035 gtc aca gca tat aaa gag gga tat gga gag ggc tgc gta acg atc          3398
Val Thr Ala Tyr Lys Glu Gly Tyr Gly Glu Gly Cys Val Thr Ile
    1040                1045                1050 cat gag atc gaa gac aat aca gac gaa ctg aaa ttc agc aac tgt          3443
His Glu Ile Glu Asp Asn Thr Asp Glu Leu Lys Phe Ser Asn Cys
    1055                1060                1065 gta gaa gag gaa gta tat cca aac aac aca gta acg tgt aat aat          3488
Val Glu Glu Glu Val Tyr Pro Asn Asn Thr Val Thr Cys Asn Asn
    1070                1075                1080 tat act ggg act caa gaa gaa tat gag ggt acg tac act tct cgt          3533
Tyr Thr Gly Thr Gln Glu Glu Tyr Glu Gly Thr Tyr Thr Ser Arg
    1085                1090                1095 aat caa gga tat gac gaa gcc tat ggt aat aac cct tcc gta cca          3578
Asn Gln Gly Tyr Asp Glu Ala Tyr Gly Asn Asn Pro Ser Val Pro
    1100                1105                1110 gct gat tac gct tca gtc tat gaa gaa aaa tcg tat aca gat gga          3623
Ala Asp Tyr Ala Ser Val Tyr Glu Glu Lys Ser Tyr Thr Asp Gly
    1115                1120                1125 cga aga gag aat cct tgt gaa tct aac aga ggc tat ggg gat tac          3668
Arg Arg Glu Asn Pro Cys Glu Ser Asn Arg Gly Tyr Gly Asp Tyr
    1130                1135                1140 aca cca cta ccg gct ggt tat gta aca aag gat tta gag tac ttc          3713
Thr Pro Leu Pro Ala Gly Tyr Val Thr Lys Asp Leu Glu Tyr Phe
    1145                1150                1155 cca gag acc gat aag gta tgg att gag atc gga gaa aca gaa gga          3758
Pro Glu Thr Asp Lys Val Trp Ile Glu Ile Gly Glu Thr Glu Gly
    1160                1165                1170 aca ttc atc gtg gat agc gtg gaa tta ctc ctt atg gag gaa taa          3803
Thr Phe Ile Val Asp Ser Val Glu Leu Leu Leu Met Glu Glu
    1175                1180                1185 gatacgttat aaaatgtaac gtatgcaaat aaagaatgat tactgaccta tattaacaga   3863
taaataagaa aatttttata cgaataaaaa acggacatca ctcttaagag aatgatgtcc   3923

<210> SEQ ID NO 8
<211> LENGTH: 1186
<212> TYPE: PRT
<213> ORGANISM: Bacillus thuringiensis

<400> SEQUENCE: 8

Asn Asn Gln Asn Gln Cys Ile Pro Tyr Asn Cys Leu Ser Asn Pro Glu
1               5                   10                  15

Glu Val Leu Leu Asp Gly Glu Arg Ile Ser Thr Gly Asn Ser Ser Ile
            20                  25                  30
```

-continued

```
Asp Ile Ser Leu Ser Leu Val Gln Phe Met Val Ser Asn Phe Val Pro
         35                  40                  45
Gly Gly Gly Phe Leu Val Gly Leu Ile Asp Phe Val Trp Gly Ile Val
 50                  55                  60
Gly Pro Ser Gln Trp Asp Ala Phe Leu Val Gln Ile Glu Gln Leu Ile
 65                  70                  75                  80
Asn Glu Arg Ile Ala Glu Phe Ala Arg Asn Ala Ala Ile Ala Asn Leu
                 85                  90                  95
Glu Gly Leu Glu Asn Asn Leu Asn Ile Tyr Val Glu Ala Phe Lys Glu
                100                 105                 110
Trp Glu Glu Asp Pro Asn Asn Pro Glu Thr Arg Thr Arg Val Ile Asp
                115                 120                 125
Arg Phe Arg Ile Leu Asp Gly Leu Leu Glu Arg Asp Ile Pro Ser Phe
130                 135                 140
Arg Ile Ser Gly Phe Glu Val Pro Leu Leu Ser Val Tyr Ala Gln Ala
145                 150                 155                 160
Ala Asn Leu His Leu Ala Ile Leu Arg Asp Ser Val Ile Phe Gly Glu
                165                 170                 175
Arg Trp Gly Leu Thr Thr Ile Asn Val Asn Glu Asn Tyr Asn Arg Leu
                180                 185                 190
Ile Arg His Ile Asp Glu Tyr Ala Asp His Cys Ala Asn Thr Tyr Asn
                195                 200                 205
Arg Gly Leu Asn Asn Leu Pro Lys Ser Thr Tyr Gln Asp Trp Ile Thr
210                 215                 220
Tyr Asn Arg Leu Arg Arg Asp Leu Thr Leu Thr Val Leu Asp Ile Ala
225                 230                 235                 240
Ala Phe Phe Pro Asn Tyr Asp Asn Arg Arg Tyr Pro Ile Gln Pro Val
                245                 250                 255
Gly Gln Leu Thr Arg Glu Val Tyr Thr Asp Pro Leu Ile Asn Phe Asn
                260                 265                 270
Pro Gln Leu Gln Ser Val Ala Gln Leu Pro Thr Phe Asn Val Met Glu
                275                 280                 285
Ser Ser Ala Ile Arg Asn Pro His Leu Phe Asp Ile Leu Asn Asn Leu
290                 295                 300
Thr Ile Phe Thr Asp Trp Phe Ser Val Gly Arg Asn Phe Tyr Trp Gly
305                 310                 315                 320
Gly His Arg Val Ile Ser Ser Leu Ile Gly Gly Gly Asn Ile Thr Ser
                325                 330                 335
Pro Ile Tyr Gly Arg Glu Ala Asn Gln Glu Pro Pro Arg Ser Phe Thr
                340                 345                 350
Phe Asn Gly Pro Val Phe Arg Thr Leu Ser Asn Pro Thr Leu Arg Leu
                355                 360                 365
Leu Gln Gln Pro Trp Pro Ala Pro Pro Phe Asn Leu Arg Gly Val Glu
370                 375                 380
Gly Val Glu Phe Ser Thr Pro Thr Asn Ser Phe Thr Tyr Arg Gly Arg
385                 390                 395                 400
Gly Thr Val Asp Ser Leu Thr Glu Leu Pro Pro Glu Asp Asn Ser Val
                405                 410                 415
Pro Pro Arg Glu Gly Tyr Ser His Arg Leu Cys His Ala Thr Phe Val
                420                 425                 430
Gln Arg Ser Gly Thr Pro Phe Leu Thr Thr Gly Val Val Phe Ser Trp
                435                 440                 445
```

-continued

```
Thr His Arg Ser Ala Thr Leu Thr Asn Thr Ile Asp Pro Glu Arg Ile
    450                 455                 460

Asn Gln Ile Pro Leu Val Lys Gly Phe Arg Val Trp Gly Gly Thr Ser
465                 470                 475                 480

Val Ile Thr Gly Pro Gly Phe Thr Gly Gly Asp Ile Leu Arg Arg Asn
                485                 490                 495

Thr Phe Gly Asp Phe Val Ser Leu Gln Val Asn Ile Asn Ser Pro Ile
                500                 505                 510

Thr Gln Arg Tyr Arg Leu Arg Phe Arg Tyr Ala Ser Ser Arg Asp Ala
            515                 520                 525

Arg Val Ile Val Leu Thr Gly Ala Ala Ser Thr Gly Val Gly Gly Gln
    530                 535                 540

Val Ser Val Asn Met Pro Leu Gln Lys Thr Met Glu Ile Gly Glu Asn
545                 550                 555                 560

Leu Thr Ser Arg Thr Phe Arg Tyr Thr Asp Phe Ser Asn Pro Phe Ser
                565                 570                 575

Phe Arg Ala Asn Pro Asp Ile Ile Gly Ile Ser Glu Gln Pro Leu Phe
                580                 585                 590

Gly Ala Gly Ser Ile Ser Ser Gly Glu Leu Tyr Ile Asp Lys Ile Glu
            595                 600                 605

Ile Ile Leu Ala Asp Ala Thr Phe Glu Ala Glu Ser Asp Leu Glu Arg
    610                 615                 620

Ala Gln Lys Ala Val Asn Ala Leu Phe Thr Ser Ser Asn Gln Ile Gly
625                 630                 635                 640

Leu Lys Thr Asp Val Thr Asp Tyr His Ile Asp Gln Val Ser Asn Leu
                645                 650                 655

Val Asp Cys Leu Ser Asp Glu Phe Cys Leu Asp Glu Lys Arg Glu Leu
                660                 665                 670

Ser Glu Lys Val Lys His Ala Lys Arg Leu Ser Asp Glu Arg Asn Leu
            675                 680                 685

Leu Gln Asp Pro Asn Phe Arg Gly Ile Asn Arg Gln Pro Asp Arg Gly
    690                 695                 700

Trp Arg Gly Ser Thr Asp Ile Thr Ile Gln Gly Gly Asp Asp Val Phe
705                 710                 715                 720

Lys Glu Asn Tyr Val Thr Leu Pro Gly Thr Val Asp Glu Cys Tyr Pro
                725                 730                 735

Thr Tyr Leu Tyr Gln Lys Ile Asp Glu Ser Lys Leu Lys Ala Tyr Thr
                740                 745                 750

Arg Tyr Glu Leu Arg Gly Tyr Ile Glu Asp Ser Gln Asp Leu Glu Ile
            755                 760                 765

Tyr Leu Ile Arg Tyr Asn Ala Lys His Glu Ile Val Asn Val Pro Gly
    770                 775                 780

Thr Gly Ser Leu Trp Pro Leu Ser Ala Gln Ser Pro Ile Gly Lys Cys
785                 790                 795                 800

Gly Glu Pro Asn Arg Cys Ala Pro His Leu Glu Trp Asn Pro Asp Leu
                805                 810                 815

Asp Cys Ser Cys Arg Asp Gly Glu Lys Cys Ala His His Ser His His
                820                 825                 830

Phe Thr Leu Asp Ile Asp Val Gly Cys Thr Asp Leu Asn Glu Asp Leu
            835                 840                 845

Gly Val Trp Val Ile Phe Lys Ile Lys Thr Gln Asp Gly His Ala Arg
    850                 855                 860
```

-continued

```
Leu Gly Asn Leu Glu Phe Leu Glu Glu Lys Pro Leu Leu Gly Glu Ala
865                 870                 875                 880

Leu Ala Arg Val Lys Arg Ala Glu Lys Lys Trp Arg Asp Lys Arg Glu
                885                 890                 895

Lys Leu Gln Leu Glu Thr Asn Ile Val Tyr Lys Glu Ala Lys Glu Ser
            900                 905                 910

Val Asp Ala Leu Phe Val Asn Ser Gln Tyr Asp Arg Leu Gln Val Asp
        915                 920                 925

Thr Asn Ile Ala Met Ile His Ala Ala Asp Lys Arg Val His Arg Ile
    930                 935                 940

Arg Glu Ala Tyr Leu Pro Glu Leu Ser Val Ile Pro Gly Val Asn Ala
945                 950                 955                 960

Ala Ile Phe Glu Glu Leu Glu Gly Arg Ile Phe Thr Ala Tyr Ser Leu
                965                 970                 975

Tyr Asp Ala Arg Asn Val Ile Lys Asn Gly Asp Phe Asn Asn Gly Leu
            980                 985                 990

Leu Cys Trp Asn Val Lys Gly His  Val Asp Val Glu Glu  Gln Asn Asn
        995                 1000                1005

His Arg  Ser Val Leu Val Ile  Pro Glu Trp Glu Ala  Glu Val Ser
    1010                1015                1020

Gln Glu  Val Arg Val Cys Pro  Gly Arg Gly Tyr Ile  Leu Arg Val
    1025                1030                1035

Thr Ala  Tyr Lys Glu Gly Tyr  Gly Glu Gly Cys Val  Thr Ile His
    1040                1045                1050

Glu Ile  Glu Asp Asn Thr Asp  Glu Leu Lys Phe Ser  Asn Cys Val
    1055                1060                1065

Glu Glu  Glu Val Tyr Pro Asn  Asn Thr Val Thr Cys  Asn Asn Tyr
    1070                1075                1080

Thr Gly  Thr Gln Glu Glu Tyr  Glu Gly Thr Tyr Thr  Ser Arg Asn
    1085                1090                1095

Gln Gly  Tyr Asp Glu Ala Tyr  Gly Asn Asn Pro Ser  Val Pro Ala
    1100                1105                1110

Asp Tyr  Ala Ser Val Tyr Glu  Glu Lys Ser Tyr Thr  Asp Gly Arg
    1115                1120                1125

Arg Glu  Asn Pro Cys Glu Ser  Asn Arg Gly Tyr Gly  Asp Tyr Thr
    1130                1135                1140

Pro Leu  Pro Ala Gly Tyr Val  Thr Lys Asp Leu Glu  Tyr Phe Pro
    1145                1150                1155

Glu Thr  Asp Lys Val Trp Ile  Glu Ile Gly Glu Thr  Glu Gly Thr
    1160                1165                1170

Phe Ile  Val Asp Ser Val Glu  Leu Leu Leu Met Glu  Glu
    1175                1180                1185

<210> SEQ ID NO 9
<211> LENGTH: 3687
<212> TYPE: DNA
<213> ORGANISM: Bacillus thuringiensis
<220> FEATURE:
<221> NAME/KEY: CDS
<222> LOCATION: (1)..(3687)

<400> SEQUENCE: 9 ttg act tca aat agg aaa aat gag aat gaa att ata aat gct gta tcg       48
Leu Thr Ser Asn Arg Lys Asn Glu Asn Glu Ile Ile Asn Ala Val Ser
1               5                   10                  15
```

-continued

| | | |
|---|---|---|
| aat cat tcc gca caa atg gat cta tta cca gat gct cgt att gag gat<br>Asn His Ser Ala Gln Met Asp Leu Leu Pro Asp Ala Arg Ile Glu Asp<br>20              25                  30 | | 96 |
| agc ttg tgt ata gcc gag ggg aac aat att gat cca ttt gtt agc gca<br>Ser Leu Cys Ile Ala Glu Gly Asn Asn Ile Asp Pro Phe Val Ser Ala<br>    35              40                  45 | | 144 |
| tca aca gtc caa acg ggt att aac ata gct ggt aga ata cta ggc gta<br>Ser Thr Val Gln Thr Gly Ile Asn Ile Ala Gly Arg Ile Leu Gly Val<br>50              55                  60 | | 192 |
| ttg ggc gta ccg ttt gct gga caa cta gct agt ttt tat agt ttt ctt<br>Leu Gly Val Pro Phe Ala Gly Gln Leu Ala Ser Phe Tyr Ser Phe Leu<br>65              70                  75              80 | | 240 |
| gtt ggt gaa tta tgg ccc cgc ggc aga gat cag tgg gaa att ttc cta<br>Val Gly Glu Leu Trp Pro Arg Gly Arg Asp Gln Trp Glu Ile Phe Leu<br>                85                  90                  95 | | 288 |
| gaa cat gtc gaa caa ctt ata aat caa caa ata aca gaa aat gct agg<br>Glu His Val Glu Gln Leu Ile Asn Gln Gln Ile Thr Glu Asn Ala Arg<br>    100                 105                 110 | | 336 |
| aat acg gct ctt gct cga tta caa ggt tta gga gat tcc ttc aga gcc<br>Asn Thr Ala Leu Ala Arg Leu Gln Gly Leu Gly Asp Ser Phe Arg Ala<br>115                 120                 125 | | 384 |
| tat caa cag tca ctt gaa gat tgg cta gaa aac cgt gat gat gca aga<br>Tyr Gln Gln Ser Leu Glu Asp Trp Leu Glu Asn Arg Asp Asp Ala Arg<br>130                 135                 140 | | 432 |
| acg aga agt gtt ctt cat acc caa tat ata gct tta gaa ctt gat ttt<br>Thr Arg Ser Val Leu His Thr Gln Tyr Ile Ala Leu Glu Leu Asp Phe<br>145                 150                 155                 160 | | 480 |
| ctt aat gcg atg ccg ctt ttc gca att aga aac caa gaa gtt cca tta<br>Leu Asn Ala Met Pro Leu Phe Ala Ile Arg Asn Gln Glu Val Pro Leu<br>                165                 170                 175 | | 528 |
| ttg atg gta tat gct caa gct gca aat tta cac cta tta tta ttg aga<br>Leu Met Val Tyr Ala Gln Ala Ala Asn Leu His Leu Leu Leu Leu Arg<br>            180                 185                 190 | | 576 |
| gat gcc tct ctt ttt ggt agt gaa ttt ggg ctt aca tcg cag gaa att<br>Asp Ala Ser Leu Phe Gly Ser Glu Phe Gly Leu Thr Ser Gln Glu Ile<br>        195                 200                 205 | | 624 |
| caa cgc tat tat gag cgc caa gtg gaa cga acg aga gat tat tcc gac<br>Gln Arg Tyr Tyr Glu Arg Gln Val Glu Arg Thr Arg Asp Tyr Ser Asp<br>210                 215                 220 | | 672 |
| tat tgc gta gaa tgg tat aat aca ggt cta aat agc ttg aga ggg aca<br>Tyr Cys Val Glu Trp Tyr Asn Thr Gly Leu Asn Ser Leu Arg Gly Thr<br>225                 230                 235                 240 | | 720 |
| aat gcc gca agt tgg gta cgg tat aat caa ttc cgt aga gat cta acg<br>Asn Ala Ala Ser Trp Val Arg Tyr Asn Gln Phe Arg Arg Asp Leu Thr<br>                245                 250                 255 | | 768 |
| tta gga gta tta gat cta gtg gca cta ttc cca agc tat gac act cgc<br>Leu Gly Val Leu Asp Leu Val Ala Leu Phe Pro Ser Tyr Asp Thr Arg<br>            260                 265                 270 | | 816 |
| act tat cca ata aat acg agt gct cag tta aca aga gaa gtt tat aca<br>Thr Tyr Pro Ile Asn Thr Ser Ala Gln Leu Thr Arg Glu Val Tyr Thr<br>        275                 280                 285 | | 864 |
| gac gca att gga gca aca ggg gta aat atg gca agt atg aat tgg tat<br>Asp Ala Ile Gly Ala Thr Gly Val Asn Met Ala Ser Met Asn Trp Tyr<br>290                 295                 300 | | 912 |
| aat aat aat gca cct tcg ttc tct gcc ata gag gct gcg gct atc cga<br>Asn Asn Asn Ala Pro Ser Phe Ser Ala Ile Glu Ala Ala Ala Ile Arg<br>305                 310                 315                 320 | | 960 |
| agc ccg cat cta ctt gat ttt cta gaa caa ctt aca att ttt agc gct<br>Ser Pro His Leu Leu Asp Phe Leu Glu Gln Leu Thr Ile Phe Ser Ala<br>                325                 330                 335 | | 1008 |

```
tca tca cga tgg agt aat act agg cat atg act tat tgg cgg ggg cac    1056
Ser Ser Arg Trp Ser Asn Thr Arg His Met Thr Tyr Trp Arg Gly His
            340                 345                 350 acg att caa tct cgg cca ata gga ggc gga tta aat acc tca acg cat    1104
Thr Ile Gln Ser Arg Pro Ile Gly Gly Gly Leu Asn Thr Ser Thr His
    355                 360                 365 ggg gct acc aat act tct att aat cct gta aca tta cgg ttc gca tct    1152
Gly Ala Thr Asn Thr Ser Ile Asn Pro Val Thr Leu Arg Phe Ala Ser
370                 375                 380 cga gac gtt tat agg act gaa tca tat gca gga gtg ctt cta tgg gga    1200
Arg Asp Val Tyr Arg Thr Glu Ser Tyr Ala Gly Val Leu Leu Trp Gly
385                 390                 395                 400 att tac ctt gaa cct att cat ggt gtc cct act gtt agg ttt aat ttt    1248
Ile Tyr Leu Glu Pro Ile His Gly Val Pro Thr Val Arg Phe Asn Phe
        405                 410                 415 acg aac cct cag aat att tct gat aga ggt acc gct aac tat agt caa    1296
Thr Asn Pro Gln Asn Ile Ser Asp Arg Gly Thr Ala Asn Tyr Ser Gln
                420                 425                 430 cct tat gag tca cct ggg ctt caa tta aaa gat tca gaa act gaa tta    1344
Pro Tyr Glu Ser Pro Gly Leu Gln Leu Lys Asp Ser Glu Thr Glu Leu
            435                 440                 445 cca cca gaa aca aca gaa cga cca aat tat gaa tct tac agt cac agg    1392
Pro Pro Glu Thr Thr Glu Arg Pro Asn Tyr Glu Ser Tyr Ser His Arg
450                 455                 460 tta tct cat ata ggt ata att tta caa tcc agg gtg aat gta ccg gta    1440
Leu Ser His Ile Gly Ile Ile Leu Gln Ser Arg Val Asn Val Pro Val
465                 470                 475                 480 tat tct tgg acg cat cgt agt gca gat cgt acg aat acg att gga cca    1488
Tyr Ser Trp Thr His Arg Ser Ala Asp Arg Thr Asn Thr Ile Gly Pro
            485                 490                 495 aat aga atc acc caa atc cca atg gta aaa gca tcc gaa ctt cct caa    1536
Asn Arg Ile Thr Gln Ile Pro Met Val Lys Ala Ser Glu Leu Pro Gln
        500                 505                 510 ggt acc act gtt gtt aga gga cca gga ttt act ggt ggg gat att ctt    1584
Gly Thr Thr Val Val Arg Gly Pro Gly Phe Thr Gly Gly Asp Ile Leu
                515                 520                 525 cga aga acg aat act ggt gga ttt gga ccg ata aga gta act gtt aac    1632
Arg Arg Thr Asn Thr Gly Gly Phe Gly Pro Ile Arg Val Thr Val Asn
530                 535                 540 gga cca tta aca caa aga tat cgt ata gga ttc cgc tat gct tca act    1680
Gly Pro Leu Thr Gln Arg Tyr Arg Ile Gly Phe Arg Tyr Ala Ser Thr
545                 550                 555                 560 gta gat ttt gat ttc ttt gta tca cgt gga ggt act act gta aat aat    1728
Val Asp Phe Asp Phe Phe Val Ser Arg Gly Gly Thr Thr Val Asn Asn
            565                 570                 575 ttt aga ttc cta cgt aca atg aac agt gga gac gaa cta aaa tac gga    1776
Phe Arg Phe Leu Arg Thr Met Asn Ser Gly Asp Glu Leu Lys Tyr Gly
        580                 585                 590 aat ttt gtg aga cgt gct ttt act aca cct ttt act ttt aca caa att    1824
Asn Phe Val Arg Arg Ala Phe Thr Thr Pro Phe Thr Phe Thr Gln Ile
                595                 600                 605 caa gat ata att cga acg tct att caa ggc ctt agt gga aat ggg gaa    1872
Gln Asp Ile Ile Arg Thr Ser Ile Gln Gly Leu Ser Gly Asn Gly Glu
610                 615                 620 gtg tat ata gat aaa att gaa att att cca gtt act gca acc ttc gaa    1920
Val Tyr Ile Asp Lys Ile Glu Ile Ile Pro Val Thr Ala Thr Phe Glu
625                 630                 635                 640 gca gaa tat gat tta gaa aga gcg caa gag gcg gtg aat gct ctg ttt    1968
Ala Glu Tyr Asp Leu Glu Arg Ala Gln Glu Ala Val Asn Ala Leu Phe
            645                 650                 655
```

```
                                          -continued
act aat acg aat cca aga aga ttg aaa aca gat gtg aca gat tat cat        2016
Thr Asn Thr Asn Pro Arg Arg Leu Lys Thr Asp Val Thr Asp Tyr His
            660                 665                 670 att gat caa gta tcc aat tta gtg gcg tgt tta tcg gat gaa ttc tgc        2064
Ile Asp Gln Val Ser Asn Leu Val Ala Cys Leu Ser Asp Glu Phe Cys
        675                 680                 685 ttg gat gaa aag aga gaa tta ctt gag aaa gtg aaa tat gcg aaa cga        2112
Leu Asp Glu Lys Arg Glu Leu Leu Glu Lys Val Lys Tyr Ala Lys Arg
    690                 695                 700 ctc agt gat gaa aga aac tta ctc caa gat cca aac ttc aca tcc atc        2160
Leu Ser Asp Glu Arg Asn Leu Leu Gln Asp Pro Asn Phe Thr Ser Ile
705                 710                 715                 720 aat aag caa cca gac ttc ata tct act aat gag caa tcg aat ttc aca        2208
Asn Lys Gln Pro Asp Phe Ile Ser Thr Asn Glu Gln Ser Asn Phe Thr
                725                 730                 735 tct atc cat gaa caa tct gaa cat gga tgg tgg gga agt gag aac att        2256
Ser Ile His Glu Gln Ser Glu His Gly Trp Trp Gly Ser Glu Asn Ile
            740                 745                 750 acc atc cag gaa gga aat gac gta ttt aaa gag aat tac gtc aca cta        2304
Thr Ile Gln Glu Gly Asn Asp Val Phe Lys Glu Asn Tyr Val Thr Leu
        755                 760                 765 ccg ggt act ttt aat gag tgt tat ccg acg tat tta tat caa aaa ata        2352
Pro Gly Thr Phe Asn Glu Cys Tyr Pro Thr Tyr Leu Tyr Gln Lys Ile
    770                 775                 780 ggg gag tcg gaa tta aaa gct tat act cgc tac caa tta aga ggt tat        2400
Gly Glu Ser Glu Leu Lys Ala Tyr Thr Arg Tyr Gln Leu Arg Gly Tyr
785                 790                 795                 800 att gaa gat agt caa gat tta gag ata tat ttg att cgt tat aat gcg        2448
Ile Glu Asp Ser Gln Asp Leu Glu Ile Tyr Leu Ile Arg Tyr Asn Ala
                805                 810                 815 aaa cat gaa aca ttg gat gtt cca ggt acc gag tcc cta tgg ccg ctt        2496
Lys His Glu Thr Leu Asp Val Pro Gly Thr Glu Ser Leu Trp Pro Leu
            820                 825                 830 tca gtt gaa agc cca atc gga agg tgc gga gaa ccg aat cga tgc gca        2544
Ser Val Glu Ser Pro Ile Gly Arg Cys Gly Glu Pro Asn Arg Cys Ala
        835                 840                 845 cca cat ttt gaa tgg aat cct gat cta gat tgt tcc tgc aga gat gga        2592
Pro His Phe Glu Trp Asn Pro Asp Leu Asp Cys Ser Cys Arg Asp Gly
    850                 855                 860 gaa aaa tgt gcg cat cat tcc cat cat ttc tct ttg gat att gat gtt        2640
Glu Lys Cys Ala His His Ser His His Phe Ser Leu Asp Ile Asp Val
865                 870                 875                 880 gga tgc aca gac ttg cat gag aat cta ggc gtg tgg gtg gta ttc aag        2688
Gly Cys Thr Asp Leu His Glu Asn Leu Gly Val Trp Val Val Phe Lys
                885                 890                 895 att aag acg cag gaa ggt cat gca aga cta ggg aat ctg gaa ttt att        2736
Ile Lys Thr Gln Glu Gly His Ala Arg Leu Gly Asn Leu Glu Phe Ile
            900                 905                 910 gaa gag aaa cca tta tta gga gaa gca ctg tct cgt gtg aag agg gca        2784
Glu Glu Lys Pro Leu Leu Gly Glu Ala Leu Ser Arg Val Lys Arg Ala
        915                 920                 925 gag aaa aaa tgg aga gac aaa cgt gaa aaa cta caa ttg gaa aca aaa        2832
Glu Lys Lys Trp Arg Asp Lys Arg Glu Lys Leu Gln Leu Glu Thr Lys
    930                 935                 940 cga gta tat aca gag gca aaa gaa gct gtg gat gct tta ttc gta gat        2880
Arg Val Tyr Thr Glu Ala Lys Glu Ala Val Asp Ala Leu Phe Val Asp
945                 950                 955                 960 tct caa tat gat aga tta caa gcg gat aca aac atc ggc atg att cat        2928
Ser Gln Tyr Asp Arg Leu Gln Ala Asp Thr Asn Ile Gly Met Ile His
                965                 970                 975
```

```
gcg gca gat aaa ctt gtt cat cga att cga gag gcg tat ctt tca gaa    2976
Ala Ala Asp Lys Leu Val His Arg Ile Arg Glu Ala Tyr Leu Ser Glu
            980                 985                 990 tta cct gtt atc cca ggt gta aat gcg gaa att ttt gaa gaa tta gaa    3024
Leu Pro Val Ile Pro Gly Val Asn Ala Glu Ile Phe Glu Glu Leu Glu
        995                 1000                1005 ggt cac att atc act gca atc tcc tta tac gat gcg aga aat gtc        3069
Gly His Ile Ile Thr Ala Ile Ser Leu Tyr Asp Ala Arg Asn Val
    1010                1015                1020 gtt aaa aat ggt gat ttt aat aat gga tta aca tgt tgg aat gta        3114
Val Lys Asn Gly Asp Phe Asn Asn Gly Leu Thr Cys Trp Asn Val
    1025                1030                1035 aaa ggg cat gta gat gta caa cag agc cat cat cgt tct gac ctt        3159
Lys Gly His Val Asp Val Gln Gln Ser His His Arg Ser Asp Leu
    1040                1045                1050 gtt atc cca gaa tgg gaa gca gaa gtg tca caa gca gtt cgc gtc        3204
Val Ile Pro Glu Trp Glu Ala Glu Val Ser Gln Ala Val Arg Val
    1055                1060                1065 tgt ccg ggg tgt ggc tat atc ctt cgt gtc aca gcg tac aaa gag        3249
Cys Pro Gly Cys Gly Tyr Ile Leu Arg Val Thr Ala Tyr Lys Glu
    1070                1075                1080 gga tat gga gag ggc tgc gta acg atc cat gaa atc gag aac aat        3294
Gly Tyr Gly Glu Gly Cys Val Thr Ile His Glu Ile Glu Asn Asn
    1085                1090                1095 aca gac gaa cta aaa ttt aaa aac cgt gaa gaa gag gaa gtg tat        3339
Thr Asp Glu Leu Lys Phe Lys Asn Arg Glu Glu Glu Glu Val Tyr
    1100                1105                1110 cca acg gat aca gga acg tgt aat gat tat act gca cac caa ggt        3384
Pro Thr Asp Thr Gly Thr Cys Asn Asp Tyr Thr Ala His Gln Gly
    1115                1120                1125 aca gct gga tgc gca gat gca tgt aat tcc cgt aat gct gga tat        3429
Thr Ala Gly Cys Ala Asp Ala Cys Asn Ser Arg Asn Ala Gly Tyr
    1130                1135                1140 gag gat gca tat gaa gtt gat act aca gca tct gtt aat tac aaa        3474
Glu Asp Ala Tyr Glu Val Asp Thr Thr Ala Ser Val Asn Tyr Lys
    1145                1150                1155 ccg act tat gaa gaa gaa acg tat aca gat gta aga aga gat aat        3519
Pro Thr Tyr Glu Glu Glu Thr Tyr Thr Asp Val Arg Arg Asp Asn
    1160                1165                1170 cat tgt gaa tat gac aga ggg tat gtc aat tat cca cca gta cca        3564
His Cys Glu Tyr Asp Arg Gly Tyr Val Asn Tyr Pro Pro Val Pro
    1175                1180                1185 gct ggt tat gtg aca aaa gaa tta gaa tac ttc cca gaa aca gat        3609
Ala Gly Tyr Val Thr Lys Glu Leu Glu Tyr Phe Pro Glu Thr Asp
    1190                1195                1200 aca gta tgg att gag att gga gaa acg gaa gga aag ttt att gta        3654
Thr Val Trp Ile Glu Ile Gly Glu Thr Glu Gly Lys Phe Ile Val
    1205                1210                1215 gat agc gtg gaa tta ctc ctc atg gaa gaa tag                        3687
Asp Ser Val Glu Leu Leu Leu Met Glu Glu
    1220                1225

<210> SEQ ID NO 10
<211> LENGTH: 1228
<212> TYPE: PRT
<213> ORGANISM: Bacillus thuringiensis

<400> SEQUENCE: 10

Leu Thr Ser Asn Arg Lys Asn Glu Asn Glu Ile Ile Asn Ala Val Ser
1               5                   10                  15
```

```
Asn His Ser Ala Gln Met Asp Leu Leu Pro Asp Ala Arg Ile Glu Asp
             20                  25                  30

Ser Leu Cys Ile Ala Glu Gly Asn Asn Ile Asp Pro Phe Val Ser Ala
         35                  40                  45

Ser Thr Val Gln Thr Gly Ile Asn Ile Ala Gly Arg Ile Leu Gly Val
     50                  55                  60

Leu Gly Val Pro Phe Ala Gly Gln Leu Ala Ser Phe Tyr Ser Phe Leu
 65                  70                  75                  80

Val Gly Glu Leu Trp Pro Arg Gly Arg Asp Gln Trp Glu Ile Phe Leu
                 85                  90                  95

Glu His Val Glu Gln Leu Ile Asn Gln Gln Ile Thr Glu Asn Ala Arg
                100                 105                 110

Asn Thr Ala Leu Ala Arg Leu Gln Gly Leu Gly Asp Ser Phe Arg Ala
             115                 120                 125

Tyr Gln Gln Ser Leu Glu Asp Trp Leu Glu Asn Arg Asp Asp Ala Arg
130                 135                 140

Thr Arg Ser Val Leu His Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
                180                 185                 190

Asp Ala Ser Leu Phe Gly Ser Glu Phe Gly Leu Thr Ser Gln Glu Ile
             195                 200                 205

Gln Arg Tyr Tyr Glu Arg Gln Val Glu Arg Thr Arg Asp Tyr Ser Asp
210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
             260                 265                 270

Thr Tyr Pro Ile Asn Thr Ser Ala Gln Leu Thr Arg Glu Val Tyr Thr
         275                 280                 285

Asp Ala Ile Gly Ala Thr Gly Val Asn Met Ala Ser Met Asn Trp Tyr
290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
             325                 330                 335

Ser Ser Arg Trp Ser Asn Thr Arg His Met Thr Tyr Trp Arg Gly His
             340                 345                 350

Thr Ile Gln Ser Arg Pro Ile Gly Gly Gly Leu Asn Thr Ser Thr His
         355                 360                 365

Gly Ala Thr Asn Thr Ser Ile Asn Pro Val Thr Leu Arg Phe Ala Ser
370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
             420                 425                 430
```

-continued

```
Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Val Ser Arg Gly Thr Thr Val Asn Asn
                565                 570                 575

Phe Arg Phe Leu Arg Thr Met Asn Ser Gly Asp Glu Leu Lys Tyr Gly
                580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
        610                 615                 620

Val Tyr Ile Asp Lys Ile Glu Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asp Tyr His
            660                 665                 670

Ile Asp Gln Val Ser Asn Leu Val Ala Cys Leu Ser Asp Glu Phe Cys
        675                 680                 685

Leu Asp Glu Lys Arg Glu Leu Leu Glu Lys Val Lys Tyr Ala Lys Arg
    690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
            740                 745                 750

Thr Ile Gln Glu Gly Asn Asp Val Phe Lys Glu Asn Tyr Val Thr Leu
        755                 760                 765

Pro Gly Thr Phe Asn Glu Cys Tyr Pro Thr Tyr Leu Tyr Gln Lys Ile
    770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
            820                 825                 830

Ser Val Glu Ser Pro Ile Gly Arg Cys Gly Glu Pro Asn Arg Cys Ala
        835                 840                 845
```

-continued

```
Pro His Phe Glu Trp Asn Pro Asp Leu Asp Cys Ser Cys Arg Asp Gly
    850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Val Phe Lys
                    885                 890                 895

Ile Lys Thr Gln Glu Gly His Ala Arg Leu Gly Asn Leu Glu Phe Ile
                900                 905                 910

Glu Glu Lys Pro Leu Leu Gly Glu Ala Leu Ser Arg Val Lys Arg Ala
                915                 920                 925

Glu Lys Lys Trp Arg Asp Lys Arg Glu Lys Leu Gln Leu Glu Thr Lys
            930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                    965                 970                 975

Ala Ala Asp Lys Leu Val His Arg Ile Arg Glu Ala Tyr Leu Ser Glu
                980                 985                 990

Leu Pro Val Ile Pro Gly Val Asn Ala Glu Ile Phe Glu Glu Leu Glu
                995                1000                1005

Gly His Ile Ile Thr Ala Ile Ser Leu Tyr Asp Ala Arg Asn Val
                1010                1015                1020

Val Lys Asn Gly Asp Phe Asn Asn Gly Leu Thr Cys Trp Asn Val
    1025                1030                1035

Lys Gly His Val Asp Val Gln Gln Ser His His Arg Ser Asp Leu
    1040                1045                1050

Val Ile Pro Glu Trp Glu Ala Glu Val Ser Gln Ala Val Arg Val
    1055                1060                1065

Cys Pro Gly Cys Gly Tyr Ile Leu Arg Val Thr Ala Tyr Lys Glu
    1070                1075                1080

Gly Tyr Gly Glu Gly Cys Val Thr Ile His Glu Ile Glu Asn Asn
    1085                1090                1095

Thr Asp Glu Leu Lys Phe Lys Asn Arg Glu Glu Glu Val Tyr
    1100                1105                1110

Pro Thr Asp Thr Gly Thr Cys Asn Asp Tyr Thr Ala His Gln Gly
    1115                1120                1125

Thr Ala Gly Cys Ala Asp Ala Cys Asn Ser Arg Asn Ala Gly Tyr
    1130                1135                1140

Glu Asp Ala Tyr Glu Val Asp Thr Thr Ala Ser Val Asn Tyr Lys
    1145                1150                1155

Pro Thr Tyr Glu Glu Glu Thr Tyr Thr Asp Val Arg Arg Asp Asn
    1160                1165                1170

His Cys Glu Tyr Asp Arg Gly Tyr Val Asn Tyr Pro Pro Val Pro
    1175                1180                1185

Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Ile Val
    1205                1210                1215

Asp Ser Val Glu Leu Leu Leu Met Glu Glu
    1220                1225
```